US011530247B2

(12) United States Patent
Foster et al.

(10) Patent No.: US 11,530,247 B2
(45) Date of Patent: Dec. 20, 2022

(54) SINGLE-CHAIN TNF RECEPTOR 2 AGONIST FUSION PROTEINS

(71) Applicant: Relinia, Inc., Euless, TX (US)

(72) Inventors: David C Foster, Euless, TX (US); Lutz B Giebel, San Mateo, CA (US); Leonard G Presta, San Francisco, CA (US)

(73) Assignee: RELINIA, INC., Euless, TX (US)

( * ) Notice: Subject to any disclaimer, the term of this patent is extended or adjusted under 35 U.S.C. 154(b) by 113 days.

(21) Appl. No.: 16/618,233

(22) PCT Filed: Jun. 5, 2018

(86) PCT No.: PCT/US2018/036139

§ 371 (c)(1),
(2) Date: Nov. 29, 2019

(87) PCT Pub. No.: WO2018/226750

PCT Pub. Date: Dec. 13, 2018

(65) Prior Publication Data

US 2020/0369739 A1 Nov. 26, 2020

Related U.S. Application Data

(60) Provisional application No. 62/515,643, filed on Jun. 6, 2017.

(51) Int. Cl.
*C07K 16/46* (2006.01)
*C07K 14/525* (2006.01)
*C07K 19/00* (2006.01)
*A61K 39/00* (2006.01)
*A61P 29/00* (2006.01)
*A61K 38/00* (2006.01)

(52) U.S. Cl.
CPC ............ *C07K 14/525* (2013.01); *A61P 29/00* (2018.01); *A61K 38/00* (2013.01); *A61K 39/00* (2013.01); *C07K 16/46* (2013.01); *C07K 19/00* (2013.01); *C07K 2319/02* (2013.01); *C07K 2319/30* (2013.01); *C07K 2319/50* (2013.01); *C07K 2319/70* (2013.01)

(58) Field of Classification Search
None
See application file for complete search history.

(56) References Cited

U.S. PATENT DOCUMENTS 8,450,460 B2 5/2013 Hill et al.
2005/0265962 A1 12/2005 Desjarlais et al.
2015/0056159 A1 2/2015 Kontermann et al.

FOREIGN PATENT DOCUMENTS

WO WO 2010/010051 A1 1/2010
WO WO-2015148708 A1 * 10/2015 ................ A61P 3/00
WO WO 2016/070156 A2 5/2016
WO WO 2016/156291 A1 10/2016
WO WO 2017/040312 A1 3/2017

OTHER PUBLICATIONS

Liu et al. Pharmacokinetics of IgG1 monoclonal antibodies produced in humanized Pichia pastoris with specific glycoforms: A comparative study with CHO produced materials. Biologicals 39:205-210 (2011). (Year: 2011).*

He et el, "A TNFR2-Agonist Facilitates High Purity Expansion of Low Purity Treg Cells,"PLoS ONE, May 25, 2016, vol. 11, Iss. 5, E01563311, pp. 1-17.

Madsen et al. "Oligodendroglial TNFR2 Mediates Membrane TNF Dependent Repair in Experimental Autoimmune Encephalomyelitis by Promoting Oligodendrocyte Differentiation and Remyelination," Journal of Neuroscience, May 4, 2016, vol. 36, No. 18, pp. 5128-5413.

Seifert et al. "The IgM CH2 Domain as Covalently Linked Homodimerization Module for the Generation of Fusion Proteins with Dual Specificity," Protein Engineering, Design & Selection, Sep. 17, 2012, vol. 25, No. 10, pp. 603-612.

Oganesyan Vaheh et al., "Structural characterization of a human Fc fragment engineered fore lack of effector functions", Acta Crystallographica Section D Biological Crystallography, vol. 64, No. 6, Jun. 1, 2008, pp. 700-704.

Boschert et al., "Single chain TNF derivatives with individually mutated receptor binding sites reveal differential stoichiometry of ligand receptor complex formation for TNFR1 and TNFR2", Cellular Signalling 22 (2010) 1088-1096.

Chopra et al., "Exogenous TNFR2 activation protects from acute GvHD via host T reg cell expansion", J. Exp. Med. Aug. 15, 2016, 2016, 1-20.

Dong et al. "Essential protective role of tumor necrosis factor receptor 2 in neurodegeneration", PNAS, vol. 113, No. 43, Oct. 25, 2016, pp. 12304-12309.

Faustman and Davis, "TNF receptor 2 and disease: autoimmunity and regenerative medicine", Frontiers in Immunology, Dec. 2013, vol. 4, Article 478, pp. 1-8.

Faustman and David, "TNF receptor 2 pathway: drug target for autoimmune diseases", Nature Reviews, Jun. 2010, vol. 9, pp. 482-493.

Fischer et al., "A TNF Receptor 2 Selective Agonist Rescues Human Neurons from Oxidative Stress-Induced Cell Death", PLoS ONE Nov. 2011, vol. 6, Issue 11, pp. 1-11.

Fischer et al., "Astrocyte-Specific Activation of TNFR2 Promotes Oligodendrocyte Maturation by Secretion of Leukemia Inhibitory Factor", GLIA 2014;62:272-283.

(Continued)

*Primary Examiner* — Elizabeth C. Kemmerer
*Assistant Examiner* — Regina M DeBerry
(74) *Attorney, Agent, or Firm* — Goodwin Procter LLP

(57) ABSTRACT

This invention provides for a fusion protein between a single chain TNFR2 Selective Agonist protein (scTNFR2 Selective Agonist) and a dimerization domain, such as an IgGFc protein. The single chain TNFR2 Selective Agonist moiety provides a therapeutic activity by selectively activating the TNFR2 form of the TNF-α receptor, thus selectively stimulating Tregs and/or increasing myelin deposition.

20 Claims, 15 Drawing Sheets

Specification includes a Sequence Listing.

(56) References Cited

OTHER PUBLICATIONS

Fischer et al., "Novel strategies to mimic transmembrane tumor necrosis factor-dependent activation of tumor necrosis factor receptor 2", Scientific Reports, Jul. 26, 2017, 7:6607, 1-13.
Fischer et al., "Selective Activation of Tumor Necrosis Factor Receptor II Induces Antiinflammatory Responses and Alleviates Experimental Arthritis", Arthritis & Rheumatology, vol. 70, No. 5, May 2018, 722-735.
Fischer et al., "Targeting sTNF/TNFR1 Signaling as a New Therapeutic Strategy", Antibodies 2015, 4, 48-70.
Gao et al., "Opposing Functions of Microglial and Macrophagic TNFR2 in the Pathogenesis of Experimental Autoimmune Encephalomyelitis", Cell Reports Jan. 3, 2017 18, 198-212.
Hutt et al., "Superior Properties of Fc-comprising scTRAIL Fusion Proteins", Mol Cancer Ther; 16(12) Dec. 2017, 2792-2802.
Loetscher et al., "Human Tumor Necrosis Factor a (TNF'a) Mutants with Exclusive Specificity for the 55-kDa or 75-kDTaN F' Receptors", J. Biol. Chem., vol. 268, No. 36, Issue of Dec. 15, 1993, pp. 26360-26367.
Krippner-Heidenreich et al., "Single-Chain TNF, a TNF Derivative with Enhanced Stability and Antitumoral Activity", J Immunol 2008; 180:8176-8183.
Okubo et al., "Homogeneous Expansion of Human T-Regulatory Cells via Tumor Necrosis Factor Receptor 2", Scientific Reports, Nov. 2013, 3 : 3153, 1-11.
Okubo et al., "Treg activation defect in type 1 diabetes: correction with TNFR2 agonism", Clinical & Translational Immunology (2016) 5, e56, 1-9.

* cited by examiner

Figure 1C
Figure 1D
Figure 1E
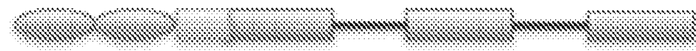
Figure 1F
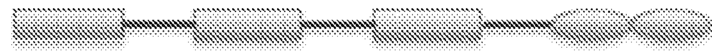
Figure 1G

MSTESMIRDVELAEEALPKKTGGPQGSRRCLFLSLFSFLIVAGATTLFCLLHFGVI*GPQR*
*EEFPRDLSLISPLAQA*V*RSSSRTPSDK*PVAHVVANPQAEGQLQWLNRRANALLANGVELR
DNQLVVPSEGLYLIYSQVLFKGQGCPSTHVLLTHTISRIAVSYQTKVNLLSAIKSPCQRE
TPEGAEAKPWYEPIYLGGVFQLEKGDRLSAEINRPDYLDFAESGQVYFGIIAL

Figure 2

*VRSSSRTPSDK*PVAHVVANPQAEGQLQWLNRRANALLANGVELR
DNQLVVPSEGLYLIYSQVLFKGQGCPSTHVLLTHTISRIAVSYQTKVNLLSAIKSPCQRE
TPEGAEAKPWYEPIYLGGVFQLEKGDRLSAEINRPDYLDFAESGQVYFGIIAL

Figure 3

PVAHVVANPQAEGQLQWLNRRANALLANGVELR
DNQLVVPSEGLYLIYSQVLFKGQGCPSTHVLLTHTISRIAVSYQTKVNLLSAIKSPCQRE
TPEGAEAKPWYEPIYLGGVFQLEKGDRLSAEINRPDYLNFRESGQVYFGIIAL

Figure 4

VRSS SRTPSDK

Figure 5

Human IgG1 Fc fusions with FcgR & C1Q knock-out
trimeric TNF at Fc N-terminus

Version 1
v1g1 EPKSCDKTHTCPPCPAPELLGGPSVFLFPPKPKDTLMISRTPEVTCVVVDVSHEDPEVKFNWYVDGVEVHNA
v1g1 KTKPREEQYNSTYRVVSVLTVLHQDWLNGKEYKCKVSNKALPAPIEKTISKAKGQPREPQVYTLPPSRDELT
v1g1 KNQVSLTCLVKGFYPSDIAVEWESNGQPENNYKTTPPVLDSDGSFFLYSKLTVDKSRWQQGNVFSCSVMHEA
v1g1 LHNHYTQKSLSLSPGK
C => S
L234A L235A P331S
v1g1 EPKSSDKTHTCPPCPAPEAAGGPSVFLFPPKPKDTLMISRTPEVTCVVVDVSHEDPEVKFNWYVDGVEVHNA
v1g1 KTKPREEQYNSTYRVVSVLTVLHQDWLNGKEYKCKVSNKALPASIEKTISKAKGQPREPQVYTLPPSRDELT
v1g1 KNQVSLTCLVKGFYPSDIAVEWESNGQPENNYKTTPPVLDSDGSFFLYSKLTVDKSRWQQGNVFSCSVMHEA
v1g1 LHNHYTQKSLSLSPGK Version 2 with GGGGS between Fc and trimeric TNF
v2g1 GGGGSEPKSCDKTHTCPPCPAPELLGGPSVFLFPPKPKDTLMISRTPEVTCVVVDVSHEDPEVKFNWYVDGVEVHNA
v2g1 KTKPREEQYNSTYRVVSVLTVLHQDWLNGKEYKCKVSNKALPAPIEKTISKAKGQPREPQVYTLPPSRDELT
v2g1 KNQVSLTCLVKGFYPSDIAVEWESNGQPENNYKTTPPVLDSDGSFFLYSKLTVDKSRWQQGNVFSCSVMHEA
v2g1 LHNHYTQKSLSLSPGK
C => S
L234A L235A P331S
v2g1 GGGGSEPKSSDKTHTCPPCPAPEAAGGPSVFLFPPKPKDTLMISRTPEVTCVVVDVSHEDPEVKFNWYVDGVEVHNA
v2g1 KTKPREEQYNSTYRVVSVLTVLHQDWLNGKEYKCKVSNKALPASIEKTISKAKGQPREPQVYTLPPSRDELT
v2g1 KNQVSLTCLVKGFYPSDIAVEWESNGQPENNYKTTPPVLDSDGSFFLYSKLTVDKSRWQQGNVFSCSVMHEA
v2g1 LHNHYTQKSLSLSPGK

FIG. 6A

Human IgG1 Fc fusions with FcgR & C1Q knock-out
trimeric TNF at Fc C-terminus

Version 3

```
v3g1 EPKSCDKTHTCPPCPAPELLGGPSVFLFPPKPKDTLMISRTPEVTCVVVDVSHEDPEVKFNWYVDGVEVHNA
v3g1 KTKPREEQYNSTYRVVSVLTVLHQDWLNGKEYKCKVSNKALPAPIEKTISKAKGQPREPQVYTLPPSRDELT
v3g1 KNQVSLTCLVKGFYPSDIAVEWESNGQPENNYKTTPPVLDSDGSFFLYSKLTVDKSRWQQGNVFSCSVMHEA
v3g1 LHNHYTQKSLSLSP(GGGGS) n=1-5
C => S
L234A L235A P331S
v3g1 EPKSSDKTHTCPPCPAPEAAGGPSVFLFPPKPKDTLMISRTPEVTCVVVDVSHEDPEVKFNWYVDGVEVHNA
v3g1 KTKPREEQYNSTYRVVSVLTVLHQDWLNGKEYKCKVSNKALPASIEKTISKAKGQPREPQVYTLPPSRDELT
v3g1 KNQVSLTCLVKGFYPSDIAVEWESNGQPENNYKTTPPVLDSDGSFFLYSKLTVDKSRWQQGNVFSCSVMHEA
v3g1 LHNHYTQKSLSLSP(GGGGS) n=1-5
```

FIG. 6B

```
Human IgG4 Fc fusions
trimeric TNF at Fc N-terminus

Version 1
v1g4    ESKYGPPCPSCPAPEFLGGPSVFLFPPKPKDTLMISRTPEVTCVVVDVSQEDPEVQFNWYVDGVEVHNA
v1g4 KTKPREEQFNSTYRVVSVLTVLHQDWLNGKEYKCKVSNKGLPSSIEKTISKAKGQPREPQVYTLPPSQEEMT
v1g4 KNQVSLTCLVKGFYPSDIAVEWESNGQPENNYKTTPPVLDSDGSFFLYSRLTVDKSRWQEGNVFSCSVMHEA
v1g4 LHNHYTQKSLSLSLGK
S => P
v1g4    ESKYGPPCPPCPAPEFLGGPSVFLFPPKPKDTLMISRTPEVTCVVVDVSQEDPEVQFNWYVDGVEVHNA
v1g4 KTKPREEQFNSTYRVVSVLTVLHQDWLNGKEYKCKVSNKGLPSSIEKTISKAKGQPREPQVYTLPPSQEEMT
v1g4 KNQVSLTCLVKGFYPSDIAVEWESNGQPENNYKTTPPVLDSDGSFFLYSRLTVDKSRWQEGNVFSCSVMHEA
v1g4 LHNHYTQKSLSLSLGK


Version 2 with GGGGS between Fc and trimeric TNF
v2g4 GGGGSESKYGPPCPSCPAPEFLGGPSVFLFPPKPKDTLMISRTPEVTCVVVDVSQEDPEVQFNWYVDGVEVHNA
v2g4 KTKPREEQFNSTYRVVSVLTVLHQDWLNGKEYKCKVSNKGLPSSIEKTISKAKGQPREPQVYTLPPSQEEMT
v2g4 KNQVSLTCLVKGFYPSDIAVEWESNGQPENNYKTTPPVLDSDGSFFLYSRLTVDKSRWQEGNVFSCSVMHEA
v2g4 LHNHYTQKSLSLSLGK
S => P
v2g4 GGGGSESKYGPPCPPCPAPEFLGGPSVFLFPPKPKDTLMISRTPEVTCVVVDVSQEDPEVQFNWYVDGVEVHNA
v2g4 KTKPREEQFNSTYRVVSVLTVLHQDWLNGKEYKCKVSNKGLPSSIEKTISKAKGQPREPQVYTLPPSQEEMT
v2g4 KNQVSLTCLVKGFYPSDIAVEWESNGQPENNYKTTPPVLDSDGSFFLYSRLTVDKSRWQEGNVFSCSVMHEA
v2g4 LHNHYTQKSLSLSLGK
```

FIG. 7A

Human IgG4 Fc fusions
trimeric TNF at Fc C-terminus

Version 3

```
v3g4    ESKYGPPCPSCPAPEFLGGPSVFLFPPKPKDTLMISRTPEVTCVVVDVSQEDPEVQFNWYVDGVEVHNA
v3g4 KTKPREEQFNSTYRVVSVLTVLHQDWLNGKEYKCKVSNKGLPSSIEKTISKAKGQPREPQVYTLPPSQEEMT
v3g4 KNQVSLTCLVKGFYPSDIAVEWESNGQPENNYKTTPPVLDSDGSFFLYSRLTVDKSRWQEGNVFSCSVMHEA
v3g4 LHNHYTQKSLSLSL(GGGGS) n=1-5
S => P
v3g4    ESKYGPPCPPCPAPEFLGGPSVFLFPPKPKDTLMISRTPEVTCVVVDVSQEDPEVQFNWYVDGVEVHNA
v3g4 KTKPREEQFNSTYRVVSVLTVLHQDWLNGKEYKCKVSNKGLPSSIEKTISKAKGQPREPQVYTLPPSQEEMT
v3g4 KNQVSLTCLVKGFYPSDIAVEWESNGQPENNYKTTPPVLDSDGSFFLYSRLTVDKSRWQEGNVFSCSVMHEA
v3g4 LHNHYTQKSLSLSL(GGGGS) n=1-5
```

FIG. 7B

```
Human IgG2 Fc fusions with C1q knock-out
trimeric TNF at Fc N-terminus

Version 1
v1g2    ERKCCVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPAPIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSPGK
C => S
P331S
v1g2    ERKSSVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPASIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSPGK


Version 2  with GGGGS between Fc and trimeric TNF
v1g2 GGGGSERKCCVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPAPIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSPGK
C => S
P331S
v1g2 GGGGSERKSSVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPASIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSPGK
```

FIG. 8A

```
Human IgG2 Fc fusions
trimeric TNF at Fc C-terminus

Version 3
v1g2    ERKCCVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPAPIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSP(GGGGS) n=1-5
C => S
P331S
v1g2    ERKSSVECPPCPAPPVAGPSVFLFPPKPKDTLMISRTPEVTCVVVDVSHEDPEVQFNWYVDGVEVHNA
v1g2 KTKPREEQFNSTFRVVSVLTVVHQDWLNGKEYKCKVSNKGLPASIEKTISKTKGQPREPQVYTLPPSREEM
v1g2 TKNQVSLTCLVKGFYPSDIAVEWESNGQPENNYKTTPPMLDSDGSFFLYSKLTVDKSRWQQGNVFSCSVMH
v1g2 EALHNHYTQKSLSLSP(GGGGS) n=1-5
```

FIG. 8B

```
v3g1 EPKSSDKTHTCPPCPAPEAAGGPSVFLFPPKPKDTLMISRTPEVTCVVVDVSHEDPEVKFNWYVDGVEVHNA
v3g1 KTKPREEQYNSTYRVVSVLTVLHQDWLNGKEYKCKVSNKALPASIEKTISKAKGQPREPQVYTLPPSRDELT
v3g1 KNQVSLTCLVKGFYPSDIAVEWESNGQPENNYKTTPPVLDSDGSFFLYSKLTVDKSRWQQGNVFSCSVMHEA
v3g1 LHNHYTQKSLSLSP(ELQLEESSAEAQDGELDG)
```

FIG. 9

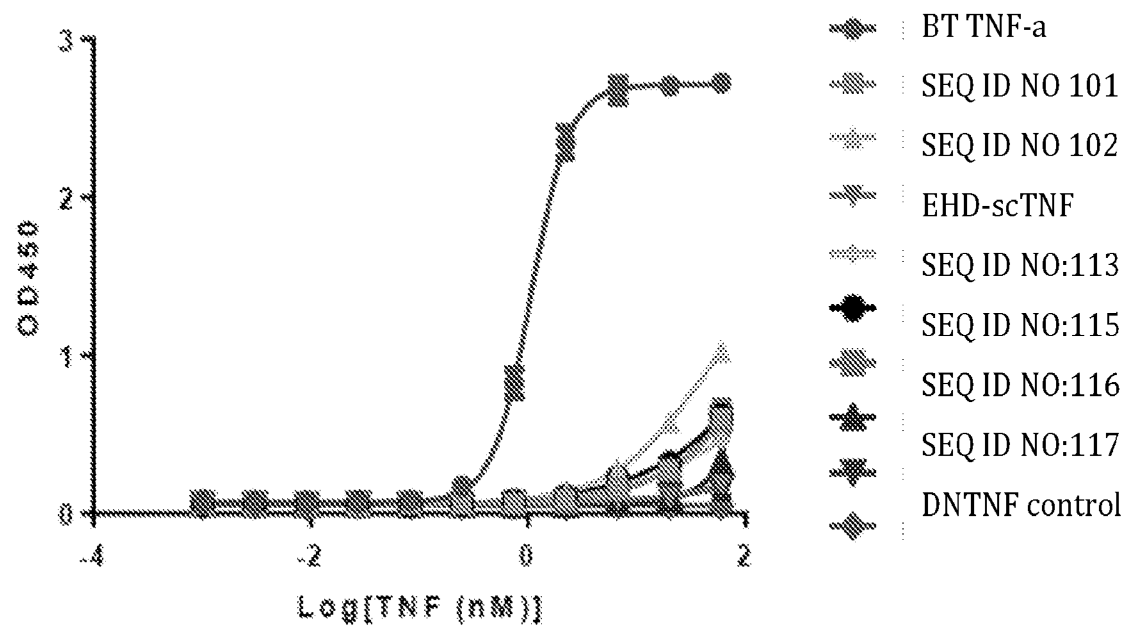
Figure 11A Binding of TNF Variants to immobilized TNFR1
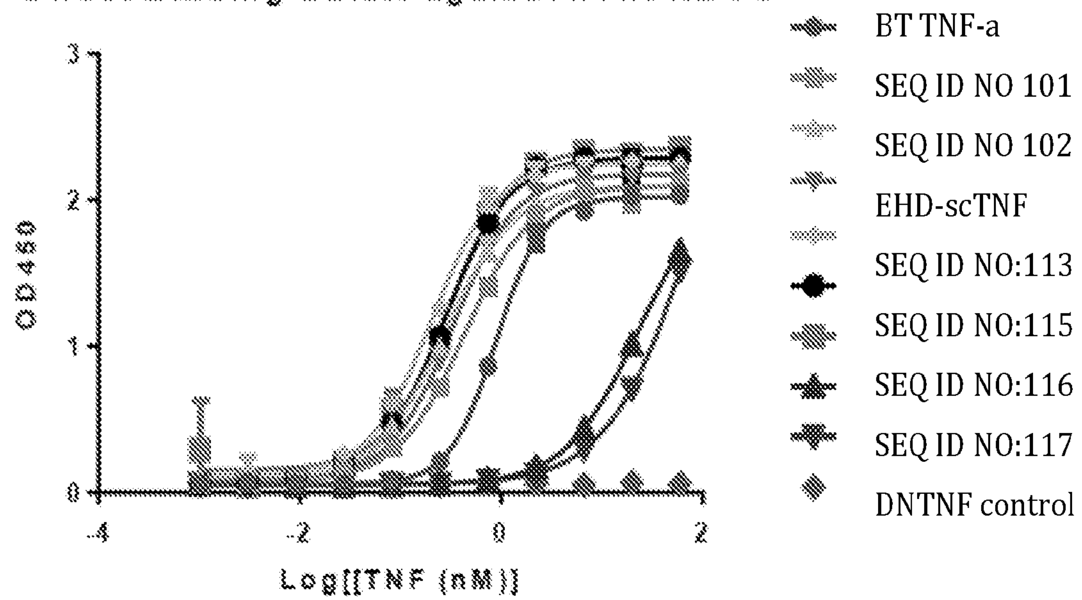
Figure 11B Binding of TNF Variants to immobilized TNFR2

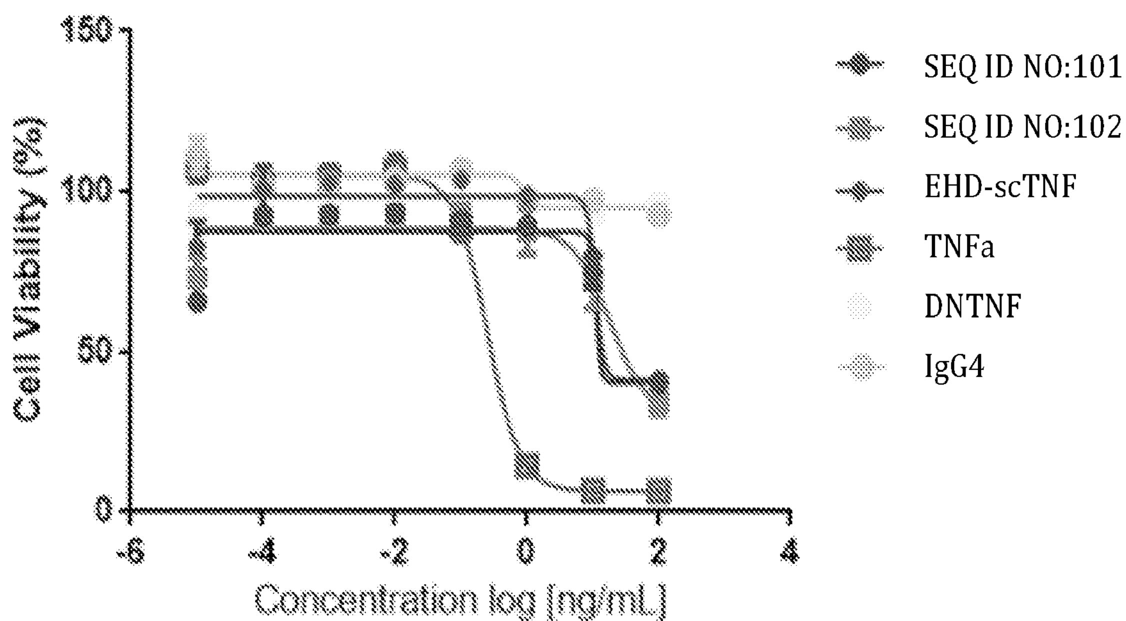
Figure 12a Kym-1 Cell Viability assay in the presence of TNF variants
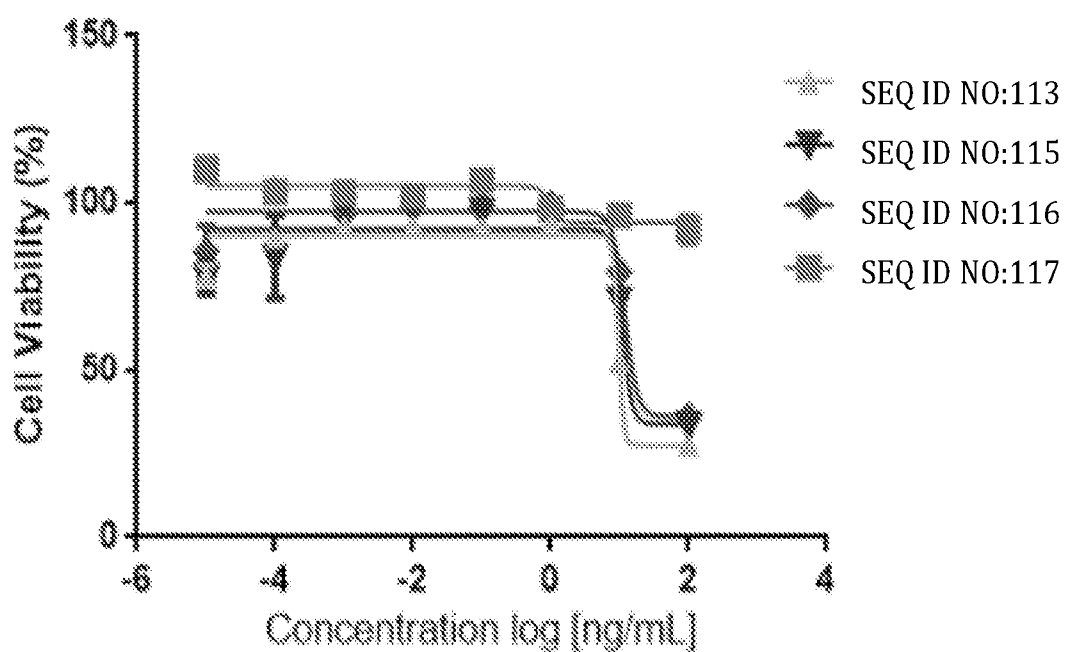
Figure 12b Kym-1 Cell Viability assay in the presence of TNF variants.

SINGLE-CHAIN TNF RECEPTOR 2 AGONIST FUSION PROTEINS

This application claims the benefit of U.S. provisional application No. 62/515,643, filed Jun. 6, 2017, and entitled SINGLE-CHAIN TNF RECEPTOR 2 AGONIST FUSION PROTEINS, which application is incorporated herein by reference.

STATEMENT REGARDING FEDERALLY FUNDED RESEARCH

None

REFERENCE TO SEQUENCE LISTING

A listing of the sequences follows the specification and is expressly included in or incorporated herein by reference.

BACKGROUND

I. Field of the Invention

The present invention relates generally to the fields of TNF Receptor 2 agonist molecules and uses thereof.

II. Description of Related Art

Tumor necrosis factor-α (TNF-α) is a cytokine that is responsible for diverse biological effects such as inflammation and immune modulation. It is a target of a variety of therapeutic agents including antibodies such as Humira and Remicade.

SUMMARY

In one embodiment the present disclosure provides a fusion protein comprising a first TNF homology domain (THD) comprising D143N/A145R mutations, wherein the THD has at least 95% identity to SEQ ID NO: 3; a second THD comprising D143N/A145R mutations, wherein the THD has at least 95% identity to SEQ ID NO: 3; a third THD comprising D143N/A145R mutations, wherein the THD has at least 95% identity to SEQ ID NO: 3; an immunoglobulin Fc domain; and a first linker peptide covalently linking the first and second THDs and a second linker covalently linking the second and third THDs.

In some embodiments the linkers in the fusion protein are composed of from 1-31 or 2-15 or 3-10 amino acids and in some embodiments include at least some stalk region from TNF-α.

In some embodiments the Fc in the fusion protein is covalently linked to the N-terminus of the N-terminal THD or the C-terminus of the C-terminal THD.

In some embodiments the Fc is covalently linked to the THD by a linker, although in some embodiments the Fc and THD are directly connected.

In some embodiments the TNFR2 agonist-Fc fusion protein selectively activates TNFR2 over TNFR1, and in some embodiments upon administration to a subject, this fusion protein selectively activates a TNFR2 in the subject over TNFR1 in the subject. In some embodiments the TNFR2 agonist-Fc fusion protein preferentially activates T regulatory cells in the subject relative to conventional T cells in the subject. In some embodiments the TNFR2 agonist-Fc fusion protein increases myelination in a subject compared to control administration.

In some embodiments the present disclosure provides a nucleic acid encoding a fusion protein as described above.

In some embodiments the present disclosure provides a method of increasing myelin deposition in a patient in need thereof comprising administering a fusion protein as described herein to said patient.

In some embodiments the present disclosure provides method of treating demyelinating disease in a patient in need thereof comprising administering a fusion protein as described herein to said patient. In some embodiments the demyelinating disease is optic neuritis or multiple sclerosis.

In some embodiments the present disclosure provides a method of treating pain in a patient in need thereof comprising administering a fusion protein as described herein to said patient.

It is contemplated that any embodiment of a method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1 Configurations of scTNFR2 agonist fusion proteins. FIG. 1C shows a scTNFR2 agonist fusion protein comprising N-terminal Fc, linker 1, stalk sequence variation, THD, linker 2, stalk sequence variation, THD, linker 2, stalk sequence, THD. FIG. 1D shows a scTNFR2 agonist fusion protein comprising N-terminal Fc, linker 1, THD, linker 2, THD, linker 2, THD. FIG. 1E shows a scTNFR2 agonist fusion protein comprising N-terminal Fc, linker 1, stalk sequence, THD, linker 2, THD, linker 2, THD. FIG. 1F shows a scTNFR2 agonist fusion protein comprising N-terminal Fc, stalk sequence, THD, linker 2, THD, linker 2, THD. FIG. 1G shows a scTNFR2 agonist fusion protein comprising N-terminal THD, linker 2, THD, linker 2, THD, linker 1, Fc.

FIG. 2 Depicts sequence of wild type TNF-α. (SEQ ID NO:1) Bold indicates ADAM17 cleavage site between A and V. Italics indicate stalk region (amino acids 57-87). Underline indicates THD (amino acids 88-233). Arrows indicate amino acids to be mutated to form TNFR2 agonist.

FIG. 3 Depicts sequence of mature, soluble TNF-α. (SEQ ID NO:2)

FIG. 4 Depicts the TNF homology domain (THD) containing D143N/A145R mutations. (SEQ ID NO:3)

FIG. 5 Depicts the sequence from the ADAM17 cleavage site in the stalk region to the C-terminus of the stalk region. (SEQ ID NO:4)

FIG. 6A Version 1—Depicts Human IgG1 Fc sequence (SEQ ID NO:5) with FcγR and C1q knockout (SEQ ID NO:6). The C-terminus of the scTNFR2 agonist can be fused directly to Fc N-terminus. Version 2—Depicts Human IgG1 Fc sequence like Version 1 with the exception that linker GGGGS (SEQ ID NO: 25) is placed between the N-terminus of the Fc and C-terminus of the scTNFR2 agonist. (SEQ ID NO:7 and SEQ ID NO:8)

FIG. 6B Version 3—Depicts Human IgG1 Fc sequence with FcγR and C1Q knockout. The scTNFR2 agonist is at the Fc C-terminus contains a spacer of $(GGGGS)_n$, wherein n=1=5 (SEQ ID NO: 44). (SEQ ID NO:9 and SEQ ID NO:10)

FIG. 7A Version 1—Depicts Human IgG4 Fc sequence. (SEQ ID NO:11) and a variant containing Ser to Pro mutation (SEQ ID NO:12) The C-terminus of the scTNFR2 agonist can be fused directly to Fc-N-terminus. Version 2—Depicts Human IgG4 Fc sequence like Version 1 with the exception that linker GGGGS (SEQ ID NO: 25) is placed between the N-terminus of the Fc and C-terminus of the scTNFR2 agonist. (SEQ ID NO:13 and SEQ ID NO:14)

FIG. 7B Version 3—Depicts Human IgG4 Fc sequence. The scTNFR2 agonist is at the Fc C-terminus which contains a spacer of $(GGGGS)_n$, wherein n=1=5 (SEQ ID NO: 44). (SEQ ID NO:15 and SEQ ID NO: 16)

FIG. 8A Version 1—Depicts Human IgG2 Fc sequence (SEQ ID NO:17) with C1q knockout (SEQ ID NO:18). The C-terminus of the scTNFR2 agonist can be fused directly to Fc-N-terminus. Version 2—Depicts Human IgG2 Fc sequence like Version 1 with the exception that linker GGGGS (SEQ ID NO: 25) is placed between the N-terminus of the Fc and C-terminus of the scTNFR2 agonist. (SEQ ID NO:19 and SEQ ID NO:20)

FIG. 8B Version 3—Depicts Human IgG2 Fc sequence with C1Q knockout. The scTNFR2 agonist is at the Fc C-terminus contains a spacer of $(GGGGS)_n$, wherein n=1=5 (SEQ ID NO: 44). (SEQ ID NO:21 and SEQ ID NO:22)

FIG. 9 Depicts human IgG sequence including a C-terminal extension (SEQ ID NO:40).

FIG. 10—FIG. 10*a* Electrophoregram of SEQ ID NO:101 under non-reducing conditions.

FIG. 11—FIG. 11A Binding of TNF Variants to immobilized TNFR1. FIG. 11B Binding of TNF Variants to immobilized TNFR2

FIG. 12—FIG. 12*a* Kym-1 Cell Viability assay in the presence of TNF variants. FIG. 12*b* Kym-1 Cell Viability assay in the presende of TNF variants.

DESCRIPTION

Figures 1A, 1B:
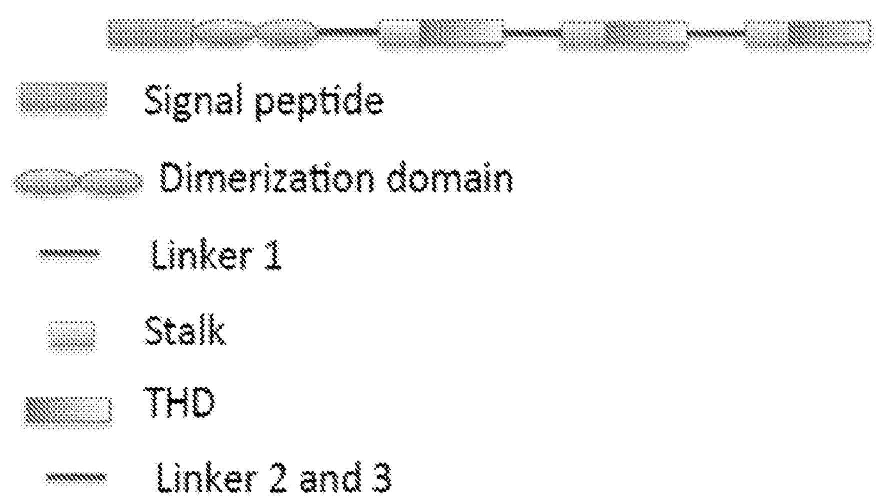
FIG. 1A shows domains of scTNFR2 agonist fusion proteins.
FIG. 1B shows a scTNFR2 agonist fusion protein comprising N-terminal Fc, linker 1, stalk sequence, THD, linker 2, stalk sequence, THD, linker 2, stalk sequence THD.
Figure 10:
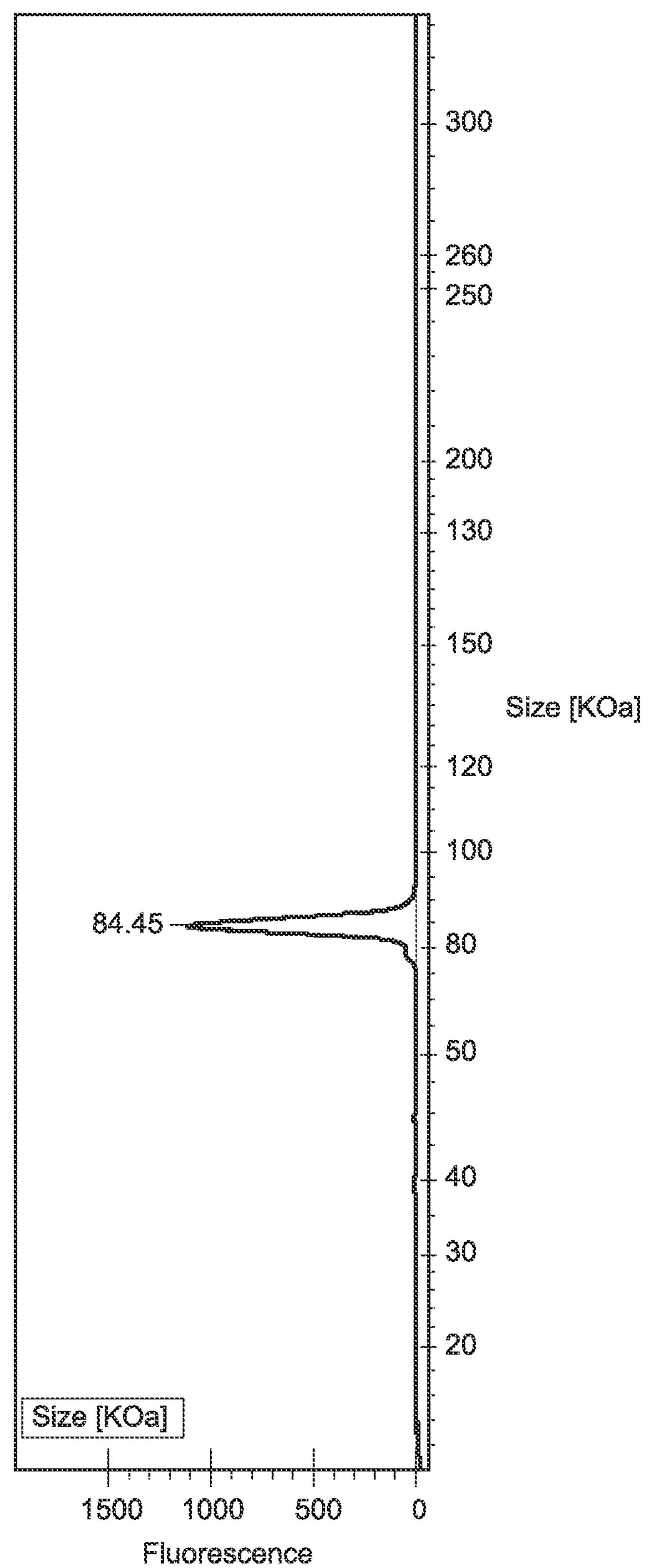
Figure 10B:
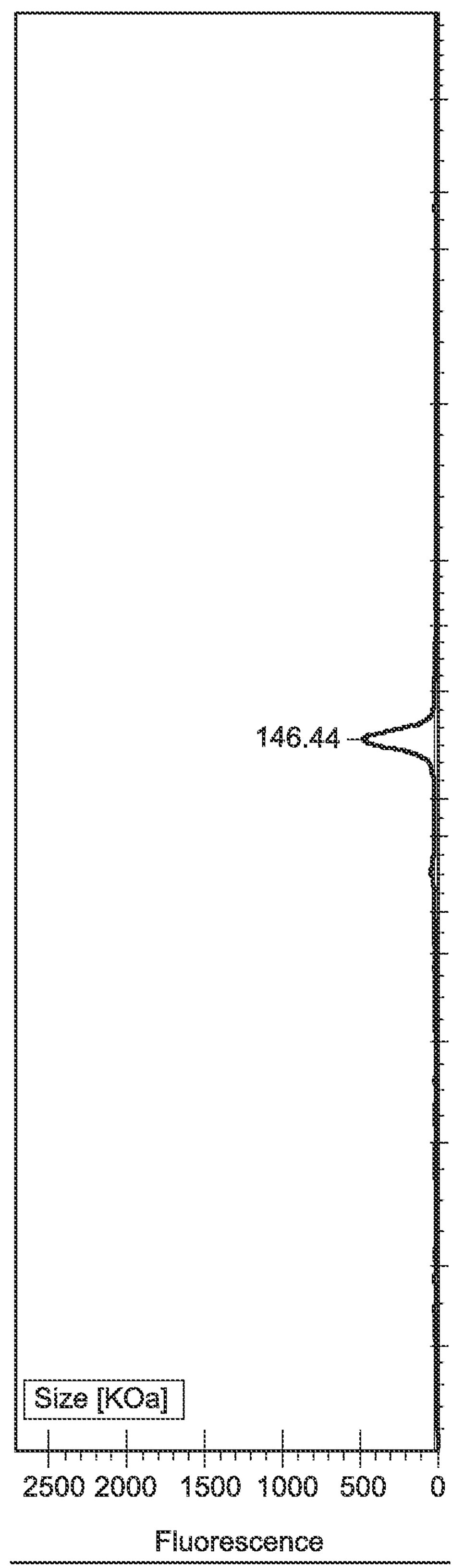
FIG. 10*b* Electrophoregram of SEQ ID NO:101 under non-reducing conditions.

TNF-α is found in both soluble forms and transmembrane forms as a homotrimer. The transmembrane precursor is cleaved, resulting in soluble form. The soluble and transmembrane form signal through two distinct receptors, TNFR1 and TNFR2, resulting in distinct biological effects. Soluble TNF-α (sTNF-α) signaling through TNFR1 is thought to mediate inflammation while transmembrane TNF-α (tmTNF-α) signaling through TNFR2 is thought to modulate immune response, stimulation of regulatory T-cells (Tregs) and myelin regulation.

While current products and methods of inhibiting TNF-α are effective and account for a significant therapeutic market, the current therapies are not without deleterious side effects. These range from immunosuppression to demyelination of neurons. For instance, therapeutics that are effective immunomodulators in the periphery are contraindicated for treatment of neuroinflammatory disorders. Currently marketed TNF-α inhibitors are labeled with a BLACK BOX WARNING specifically warning against treatment of neurological diseases because they cause demyelination resulting in worsening of the condition. These current TNF-α inhibitors block signaling by both soluble and tmTNF-α, resulting in the beneficial anti-inflammatory effects but also leading to deleterious side effects. Accordingly, there is a significant need for the development of molecules that stimulate signaling through the TNFR2 but not TNFR1.

Accordingly, the present disclosure provides novel TNFR2 agonist molecules. These find use as improved compositions and methods for treating disorders such as, but not limited to pain, nerve injury and/or demyelinating diseases such as, but not limited to multiple sclerosis and optic neuritis.

Definitions

"At least a percent (eg. 97%) sequence identify to Sequence ID No. X" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci USA 67:22264-2268, 1990) modified as in Karlin and Altschul, Proc. Natl. Acad. Sci USA 90:5873-5877, 1993 is incorporated into the NBLAST and XBLAST programs of Altschul et al. (Altschul, et al. J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL world-wide web address of: "ncbi.nlm.nih.gov" for these programs. In a specific embodiment, percent identity is calculated using BLAST2 with default parameters as provided by the NCBI.

"N-terminus" refers to the end of a peptide or polypeptide that bears an amino group in contrast to the carboxyl end bearing a carboxyl acid group.

"C-terminus" refers to the end of a peptide or polypeptide that bears a carboxylic acid group in contrast to the amino terminus bearing an amino group.

"C-terminal IgG Fc protein moiety" refers to a portion of a fusion protein that derives from two identical protein fragments, each having a hinge region, a second constant domain, and a third constant domains of the IgG molecule's two heavy chains, and consisting of the carboxy-terminal heavy chains disulphide bonded to each other through the hinge region. It is functionally defined as that part of the IgG molecule that interacts with the complement protein C1q and the IgG-Fc receptors (FcγR), mediating Complement-dependent cytotoxicity (CDC) and antibody-dependent cellular cytotoxicity (ADCC) effector functions. The sequence can be modified to decrease effector functions, to increase circulating half-life, and to eliminate glycosylation sites.

Single-Chain TNF-α Variants

The single chain TNF-α variant fusion proteins described herein are generally composed of contiguous amino acids having the following domain structure:

DD-L1-THD-L2-THD-L3-THD or THD-L2-THD-L3-THD-L1-DD, where DD is a dimerization domain as described herein. L1, L2 and L3 are linkers that may be the same or different and THD is a TNF-a homology domain as defined herein. In preferred embodiments the fusion protein is encoded by contiguous nucleotides and expressed as a single contiguous polypeptide.

"N-terminal human TNF-α variant protein moiety" or "N-terminal scTNFR2 Agonist (scTNFR2)" refers to an N-terminal domain of a fusion protein that is derived from a wild type TNF-α protein structurally and functionally defined herein and that is composed of three THDs.

"C-terminal human TNF-α variant protein moiety" or "C-terminal scTNFR2 Agonist (scTNFR2)" refers to a C-terminal domain of a fusion protein that is derived from a wild type TNF-α protein structurally and functionally defines above.

Tregs

"Tregs" or "Treg cells" refer to Regulatory T cells. Regulatory T cells are a class of T cells that suppress the activity of other immune cells, and are defined using flow cytometry by the cell marker phenotype CD4+CD25+FOXP3+. Because FOXP3 is an intracellular protein and requires cell fixation and permeablization for staining, the cell surface phenotype CD4+CD25+CD127− can be used for defining live Tregs. Tregs also include various Treg subclasses, such as tTregs (thymus-derived) and pTregs (peripherally-derived, differentiated from naive T cells in the periphery).

Peptide Linkers

"Peptide linker" is defined as an amino acid sequence located between the two proteins comprising a fusion protein, such that the linker peptide sequence is not derived from either partner protein. Peptide linkers are incorporated into fusion proteins as spacers in order to promote proper protein folding and stability of the component protein moieties, to improve protein expression, or to enable better bioactivity of the two fusion partners (Chen, et al., 2013, Adv Drug Deliv Rev. 65(10):1357-69). Peptide linkers can be divided into the categories of unstructured flexible peptides or rigid structured peptides.

Fc Fusion Proteins

An "Fc fusion protein" is a protein made by recombinant DNA technology in which the translational reading frame of the Fc domain of a mammalian IgG protein is fused to that of another protein ("Fc fusion partner") to produce a novel single recombinant polypeptide. Fc fusion proteins are typically produced as disulfide-linked dimers, joined together by disulfide bonds located in the hinge region.

Functional Activation

"Bioactivity" refers to the measurement of biological activity in a quantitative cell-based in vitro assay.

"Functional activation of Treg cells" is defined a TNF-α-mediated response in Tregs. Assay readouts for functional activation of Treg cells includes stimulation of pSTAT5, Treg cell proliferation, and stimulation of the levels of Treg effector proteins.

Design and Construction

There are multiple options for the design and construction of an Fc fusion protein, and the choices among these design options are presented below to permit the generation of a molecule with the desired biological activity and pharmaceutical characteristics. Key design options are: (1) the nature of the TNF-α Selective Agonist, (2) the choice of the dimerization domain protein moiety, i.e. Fc, (3) the configuration of fusion partners in the fusion protein, and (4) the amino acid sequence at the junction between the dimerization domain and the fusion partner protein as well as between the three THDs.

General Methods

In general, preparation of the fusion proteins of the invention can be accomplished by procedures disclosed herein and by recognized recombinant DNA techniques involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, culturing of the host. Additionally, the fusion molecules can be isolated and purified using chaotropic agents and well known electrophoretic, centrifugation and chromatographic methods. See generally, Sambrook et al., Molecular Cloning: A Laboratory Manual (2nd ed. (1989); and Ausubel et al., Current Protocols in Molecular Biology, John Wiley & Sons, New York (1989) for disclosure relating to these methods.

The genes encoding the fusion proteins of this invention involve restriction enzyme digestion and ligation as the basic steps employed to yield DNA encoding the desired fusions. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art (λ.ZAP and pBLUESCRIPT SK-1, Stratagene, LaJolla, Calif., pET, Novagen Inc., Madison, Wis.—cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

Site-directed mutagenesis is typically used to introduce specific mutations into the genes encoding the fusion proteins of this invention by methods known in the art. See, for example, U.S. Patent Application Publication 2004/0171154; Storici et al., 2001, Nature Biotechnology 19: 773-776; Kren et al., 1998, Nat. Med. 4: 285-290; and Calissano and Macino, 1996, Fungal Genet. Newslett. 43: 15-16. Any site-directed mutagenesis procedure can be used in the present invention. There are many commercial kits available that can be used to prepare the variants of this invention.

Various promoters (transcriptional initiation regulatory region) may be used according to the invention. The selection of the appropriate promoter is dependent upon the proposed expression host. Promoters from heterologous sources may be used as long as they are functional in the chosen host.

Various signal sequences may be used to facilitate expression of the proteins described herein. Signal sequence are selected or designed for efficient secretion and processing in the expression host may also be used. A signal sequence, which is homologous to the TCR coding sequence or the mouse IL-2 coding sequence may be used for mammalian cells. Other suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

The expression cassette(s) are joined to appropriate vectors compatible with the host that is being employed. The vector must be able to accommodate the DNA sequence coding for the fusion proteins to be expressed. Suitable host cells include eukaryotic and prokaryotic cells, preferably those cells that can be easily transformed and exhibit rapid growth in culture medium. Specifically preferred hosts cells include prokaryotes such as *E. coli, Bacillus subtillus*, etc. and eukaryotes such as animal cells and yeast strains, e.g., *S. cerevisiae*. Mammalian cells are generally preferred, particularly HEK, J558, NSO, SP2-O or CHO. Other suitable hosts include, e.g., insect cells such as Sf9. Conventional culturing conditions are employed. See Sambrook, supra. Stable transformed or transfected cell lines can then be selected. In vitro transcription-translation systems can also be employed as an expression system.

Nucleic acid encoding a desired fusion protein can be introduced into a host cell by standard techniques for transfecting cells. The term “transfecting” or “transfection” is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Alternatively, one can use synthetic gene construction for all or part of the construction of the proteins described herein. This entails in vitro synthesis of a designed polynucleotide molecule to encode a polypeptide molecule of interest. Gene synthesis can be performed utilizing a number of techniques, such as the multiplex microchip-based technology described by Tian, et. al., (Tian, et. al., Nature 432:1050-1054) and similar technologies wherein oligonucleotides are synthesized and assembled upon photo-programmable microfluidic chips.

The fusion proteins of this invention are isolated from harvested host cells or from the culture medium. Standard protein purification techniques are used to isolate the proteins of interest from the medium or from the harvested cells. In particular, the purification techniques can be used to express and purify a desired fusion protein on a large-scale (i.e. in at least milligram quantities) from a variety of approaches including roller bottles, spinner flasks, tissue culture plates, bioreactor, or a fermentor.

The TNFR2 Selective Agonist Moiety and Fusion Proteins

In one embodiment the molecules described herein are single-chain, trimeric TNF-α molecules. By “single-chain” is meant that a single polypeptide comprises 3 THDs as described herein.

The single chain TNF-α variant fusion proteins described herein are generally composed of contiguous amino acids having the following domain structure: DD-L1-THD-L2-THD-L3-THD or THD-L2-THD-L3-THD-L1-DD, where DD is a dimerization domain as described herein. L1, L2 and L3 are linkers that may be the same or different and THD is a TNF-a homology domain as defined herein. In preferred embodiments the fusion protein is encoded by contiguous nucleotides and expressed as a single contiguous polypeptide.

Full length human TNF-α has the sequence as set forth in FIG. 2 (SEQ ID NO:1). It is a type 2 transmembrane protein that is cleaved by the protease ADAM17 to produce the cleaved, soluble TNF-α and uncleaved transmembrane TNF-α. Both soluble and transmembrane molecules signal through cognate receptors. Soluble TNF-a signals primarily through TNFR1, while transmembrane TNF-α signals primarily through TNFR2. The cleaved, soluble TNF-α has the sequence shown in SEQ ID NO:2. C-terminal to the cleavage site is a domain that forms the TNF-homology domain (THD), which is a sequence and structurally similar domain found in members of the TNF superfamily, that makes up the receptor binding domain of the molecule. Of note, a region N-terminal to the THD domain and including the ADAM17 cleavage site is a domain of the molecule referred to as the “stalk region”. This stalk region does not appear to be found in the receptor-binding portion of the molecule. Accordingly, domains of TNF-α include from N- to C-terminus: N-terminal intracellular domain, a transmembrane domain, stalk region, ADAM17 cleavage site within the stalk region and THD domain. The transmembrane domain terminates at amino acid 56. The stalk region is defined as amino acids 57-87 of the full-length sequence. The ADAM17 cleavage site is found between amino acids 76/77. The THD domain begins at amino acid 88 and extends to amino acid 233. This is summarized in FIG. 2.

Mutations in the THD have been identified that abrogate binding to TNFR1 and result in a molecule that agonizes TNFR2. The mutations are D143N and A145R, wherein the numbering is based on the sequence of soluble TNF-α. This corresponds to D219N and A221R wherein the numbering is based on the full length TNF-α sequence. That is, at these positions, the native sequences of D and A are mutated to an N and R, respectively. These mutations will be referred to as TNFR2 agonist sequences herein.

Accordingly, the present disclosure provides single-chain TNFR2 agonists (scTNFR2) comprising a first, second and third THD domain comprising the TNFR2 agonist sequences. In some embodiments all three of the THD domains of the scTNFR2 agonist comprise the TNFR2 agonist sequences. Sequence of the THD domain comprising the TNFR2 agonist sequences is found in SEQ ID NO:3.

The variants of this invention optionally include conservatively substituted variants that apply to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations, which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

With regard to conservative substitution of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a conservatively modified variant where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:

1) Alanine (A), Glycine (G);
2) Serine (5), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).

Dimerization Domains

One design choice is the nature of the dimerization domains of the fusion protein. Without being bound by theory, it is thought that dimerization enhances signaling by the TNFR2 agonist and also may improve half-life of the fusion protein. There are many different dimerization domains, such as Fc fusion proteins derived from other dimerizing molecules, such as IgE heavy chain domain 2 (EHD2) and IgM heavy chain domain 2 (MHD2).

Fc Protein Moiety

The main therapeutic applications of Fc fusion proteins are (1) endowing the fusion partner protein with immunoglobulin Fc effector functions; or (2) increasing the circulating half-life of the fusion partner protein (Czajkowsky, et al., 2012, EMBO Mol Med. 4:1015-28). The primary effector functions of IgG proteins are Complement-Dependent Cytotoxicity (CDC) and Antibody-Dependent Cellular Cytotoxicity (ADCC), functions mediated by Fc binding to complement protein C1q and to IgG-Fc receptors (FcγR), respectively. These effector functions are important when the therapeutic protein is used to direct or enhance the immune response to a particular antigen target or cell. The fusion protein of this invention is designed solely to increase the circulating half-life of the TNFR2 Selective Agonist moiety, and effector functions are not needed and can even be toxic, and thus in some embodiments not desired. For instance, a scTNFR2 agonist-Fc fusion protein with an effector function-competent Fc can potentially kill the Treg cells that the fusion protein of this invention is seeking to activate and expand, exactly the opposite of the therapeutic goal for autoimmune diseases. There are four human IgG subclasses that differ in effector functions (CDC, ADCC), circulating half-life, and stability (Salfeld, J. G., 2007, Nature Biotechnology 25:1369-72). IgG1 possesses Fc effector functions, is the most abundant IgG subclass, and is the most commonly used subclass in US FDA-approved therapeutic proteins. IgG2 is deficient in Fc effector functions, but is subject to dimerization with other IgG2 molecules, and is also subject to instability due to scrambling of disulfide bonds in the hinge region. IgG3 possesses Fc effector functions, and has an extremely long, rigid hinge region. IgG4 is deficient in Fc effector functions, has a shorter circulating half-life than the other subclasses, and the IgG4 dimer is biochemically unstable due to only a single disulfide bond in the hinge region leading to the exchange of H chains between different IgG4 molecules. A skilled artisan would recognize that Fc protein moieties from IgG2 and IgG4 do not possess effector functions and can be used in this invention. The skilled artisan would also recognize that Fc sequence modifications have been described in the art that such that the hinge region of IgG2 Fc can be modified to prevent aggregation, or that the hinge region of IgG4 Fc can be modified to stabilize dimers. It will be appreciated by those of ordinary skill in the art that the IgG described in the sequences of the fusion constructs disclosed herein may be changed. That is, where an IgG1 sequence is disclosed, this can be exchanged with an IgG2 or IgG4 and the like.

Alternatively, effector function-deficient variants of IgG1 have been generated. One such variant has an amino acid substitution at position N297, the location of an N-linked glycosylation site. Substitution of this asparagine residue removes the glycosylation site and significantly reduces ADCC and CDC activity (Tao, M. H., et al., 1989, J Immunol. 143:2595-2601). This variant is used as an exemplary case in the invention herein. Another effector function deficient IgG1 variant is IgG1 (L234F/L235E/P331S) (Oganesyan, et al., 2008, Acta Crystallogr D Biol Crystallogr. 64:700-4), which mutates amino acids in the C1q and FcγR binding sites, and one skilled in the art would consider using these or similar Fc variants to generate effector-deficient and stable scTNFR2 agonist-Fc fusion proteins. Other mutations at these sites, such as L234A and L235A can also be used in the fusion protein described herein. Exemplary IgG sequences and variants are shown in FIGS. 6-8 and in SEQ ID NOs:5-22.

A skilled artisan would also recognize that forms of Fc protein moieties engineered to be stable monomers rather than dimers (Dumont, J. A., et., al., 2006, BioDrugs 20:151-60; Liu Z, et al., J Biol Chem. 2015 20; 290:7535-62) can also be combined with the TNFR2 selective agonist of this invention. In addition, a skilled artisan would recognize that a functionally monomeric heterodimer composed of a TNFR2 agonist-Fc H chain polypeptide combined with an Fc H chain polypeptide and assembled using bispecific antibody technology (Zhu Z, et al., 1997 Protein Sci. 6:781-8) can also be combined with the TNFR2 Selective Agonist of this invention. In addition, a skilled artisan will recognize that Fc variants that lack some or all of the hinge region can be used with this invention.

Fc fusion proteins can be made in two configurations, indicated here as X-Fc, where X, the scTNFR2 agonist fusion partner protein, is at the N-terminus and Fc is at the C-terminus, and Fc-X, where the Fc is at the N-terminus, and the scTNFR2 agonist fusion partner protein is at the C-terminus (FIG. 1). There are examples in the literature showing that different fusion partners can have distinct preferences for N- or C-terminal Fc fusions. For instance, FGF21 has been shown to have a strong preference for the Fc-X configuration. Fc-FGF21 has receptor-activating bioactivity essentially the same as FGF21 itself, while FGF21-Fc has 1000-fold reduced bioactivity (Hecht, et al., 2012, PLoS One. 7(11):e49345). A number of IL2 agonist Fc fusion proteins have been made for various applications, and these have been reported to have good IL-2 bioactivity when directly fused to Fc in both the Fc-X (Gillies, et al., 1992, Proc Natl Acad Sci, 89:1428-32; Bell, et al., 2015, J Autoimmun. 56:66-80) and X-Fc (Zheng, X. X., et al., 1999, J Immunol. 163:4041-8) configurations. Gavin, et al. (US 20140286898 A1) describes Fc fusion proteins containing IL-2 and certain IL-2 variants in the in the Fc-X configuration that have bioactivity similar to that of the free IL-2 cytokine, but in contrast to the results of Zheng et al, (Zheng, X. X., et al., 1999, J Immunol. 1999, 163:4041-8) found that IL-2 variant fusion proteins in the X-Fc configuration have reduced or no bioactivity. Thus, whether an N-terminal dimerization domain or a C-terminal dimerization within any given fusion protein is preferred is unpredictable.

EHD2

A recently described dimerization domain may also find use in connection with the scTNFR2 agonist described herein. This polypeptide was used to form dimers of other molecules in WO 2013/156148, which is expressly incorporated herein by reference. The EHD2 sequence is (SEQ ID NO: 23)

```
DFTPPTVKILQSSCDGGGHFPPTIQLLCLVSGYTPGTINITWLEDGQVMD

VDLSTASTTQEGELASTQSELTLSQKHWLSDRTYTCQVTYQGHTFEDSTK

KCADSN.
```

MHD2

Another recently described dimerization domain may also find use in connection with the scTNFR2 agonist described herein. This polypeptide was used to form dimers of other molecules in WO 2013/156148. The MHD2 sequence is (SEQ ID NO: 24)

```
AELPPKVSVFVPPRDGFFGNPRKSKLICQATGFSPRQIQVSWLREGKQV

GSGVTTDQVQAEAKESGPTTYKVTSTLTIKESDWLGQSMFTCRVDHRGLT

FQQNASSMCVPD.
```

Linker

The amino acid sequence at the junction between the Fc and the fusion partner protein can be either (1) a direct fusion of the two protein sequences or (2) a fusion with an intervening linker peptide. Of the 10 Fc fusion proteins that are presently approved by the US FDA for clinical use (TABLE I), 8 are direct fusions of the fusion partner protein with Fc, while 2 possess linker peptides, so many Fc fusion proteins can be functional without linker peptides. Linker peptides are included as spacers between the two protein moieties. Linker peptides can promote proper protein folding and stability of the component protein moieties, improve protein expression, and enable better bioactivity of the component protein moieties (Chen, et al., 2013, Adv Drug Deliv Rev. 65:1357-69). Peptide linkers used in many fusion proteins are designed to be unstructured flexible peptides. A study of the length, sequence, and conformation of linkers peptides between independent structural domains in natural proteins has provided a theoretical basis for the design of flexible peptide linkers (Argos, 1990, J Mol Biol. 211:943-58). Argos provided the guidance that long flexible linker peptides be composed of small nonpolar residues like Glycine and small polar resides like Serine and Threonine, with multiple Glycine residues enabling a highly flexible conformation and Serine or Threonine providing polar surface area to limit hydrophobic interaction within the peptide or with the component fusion protein moieties. Many peptide linkers described in the literature are rich in glycine and serine, such as repeats of the sequence GGGGS (SEQ ID NO:25), although an artisan skilled in the art will recognize that other sequences following the general recommendations of Argos (Argos, 1990, J Mol Biol. 20; 211(4):943-58) can also be used. In some embodiments polypeptide sequences from one of the fusion partners may be used as a linker. For instance, N- or C-terminal extensions from TNF-α or a dimerization domain, such as Fc, could be used all or part of the linker between the fusion partners. In some embodiments the C-terminal extension from human IgG finds use as a linker and is shown as: ELQLEESSAEAQDGELDG (SEQ ID NO:41) or a variant of this also finds use as a linker: ELQLEESSAEAQGG (SEQ ID NO:42).

TABLE I

US FDA-approved Fc fusion proteins and their characteristics

| DRUG | Fc Isotype | Fusion Partner | N vs C fusion | Linker Peptide | Half-life (days) |
|---|---|---|---|---|---|
| Romiplostim | G1 | TPO-R peptide | C | Y | 3.5 |
| Etanercept | G1 | P75 TNFa-R | N | N | 4.3 |
| Alefacept | G1 | LFA3 | N | N | 10.1 |
| Rilonacept | G1 | IL1-R | N | N | 8.6 |
| Abatacept | G1 | CTLA4 | N | N | 16.7 |
| Belatacept | G1 | CTLA4 (mut) | N | N | 9.8 |
| Aflibercept | G1 | VEGF R1 + R2 | N | N | n/a |
| Dulaglutide | G4 (mut) | GLP1 | N | Y | 3.7 |
| Eloctate | G1 | FVIII | N | N | 0.8 |
| Alprolix | G1 | FIX | N | N | 3.6 |

In some embodiments, particularly when the fusion protein is in the DD-X configuration, the dimerization domain (DD), i.e. Fc, is directly linked to the N-terminus of the single-chain THD, i.e. TNFR2 agonist.

In some embodiments, particularly when the fusion protein is in the DD-X configuration, the linker between the N-terminus of the first THD domain of the scTNFR2 agonist is sequence from TNF-α itself. That is, sequences from the native TNF-α stalk region are used as a linker between the THD domain of the TNFR2 agonist and the C-terminus of the Fc domain. The linker between the THD domain of the TNFR2 agonist and the C-terminus of the Fc domain contains from 1 to 31 amino acids or contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids. The stalk region contains the sequences shown below and the linker using contiguous amino acids from this region may include from 1 to 31 contiguous amino acids of this sequence. The sequence from the first amino acid of the stalk region to last amino acid prior to the THD domain includes: GPQREEF-PRDLSLISPLAQAVRSSSRTPSDK (SEQ ID NO:26). In some embodiments sequences comprising at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 contiguous sequences from the stalk region can be used as a linker between the N-terminus of the scTNF agonist and dimerization domain.

In some embodiments, other linkers, such as combinations of Gly and Ser find use as linkers. In some embodiments linkers using $(GGGGS)_n$, where n=1-5 (SEQ ID NO: 44) find use as linkers between the dimerization domain, i.e. Fc and first THD of the scTNFR2 agonist. In some embodiments, combinations of the stalk region sequences and Gly/Ser amino acids find use as the linker.

In some embodiments a linker peptide of 5, 10, 15, or 20 amino acids will have a maximum fully extended length of 17.5 Å, 35 Å, 52.5 Å, or 70 Å, respectively. The maximal end-to-end length of the peptide linker can also be a guide for defining the characteristics of a peptide linker in this invention. The goal of a linker peptide within the current invention is to enable attainment of an appropriate conformation and orientation of the individual fusion protein moieties to allow the engagement of the TNFR2 Selective Agonist moiety with its cognate receptor and allow the binding of the Fc moiety to the FcRn to enable fusion protein recycling and a prolonged circulating half-life. Since the factors influencing these interactions are difficult to predict, the requirement for and the proper length of a linker peptide must be empirically tested and determined. Many Fc fusion proteins do not require linker peptides, as evidenced by the 8 out of 10 US FDA-approved Fc fusion proteins lacking such peptides listed in Table I. In contrast, Dulaglutide, a fusion of GLP-1 and Fc, contains a 15 residue peptide linker which has a strong influence on bioactivity (Glaesner, U.S. Pat. No. 7,452,966 B2).

In the context of the single-chain TNFR2 agonist, other linkers may be found between the THD domains. That is, a linker may be found between the first and second and then the second third THD domain of the TNFR2 agonist. The linkers may be the same or may be different. In some embodiments the linkers may be any linker outlined herein including GGGGS (SEQ ID NO: 25) linkers. In some embodiments the linker may comprise multiple units of the GGGGS (SEQ ID NO: 25) sequence as described as $(GGGGS)_n$, wherein n=1, 2, 3, 4, 5, 6, 7, 8, 9 or 10 (SEQ ID NO: 45). In some embodiments, sequences from the stalk region find use as linkers between the THDs. In addition, in some embodiments, combinations of Gly/Ser amino acids as well as contiguous amino acids from the stalk region find use as linkers between THDs. Linker between the first and second THDs may be the same or different from the linker between the second and third THD but generally both linkers will be comprised of $(GGGGS)_n$, wherein n=1, 2, 3, 4, 5, 6, 7, 8, 9 or 10 (SEQ ID NO: 45) and/or contiguous sequences from the stalk region.

In other embodiments, particularly in the X-DD configuration, a linker may be placed between the C-terminus of the third THD domain and the N-terminus of dimerization domain, i.e. Fc domain. Again this can be Gly/Ser linkers as described herein and may comprise $(GGGGS)_n$, where n=1-5 (SEQ ID NO: 44).

Fusion Proteins

Accordingly, the present disclosure provides scTNFR2 fusion proteins comprising a dimerization domain, three THD's each comprising the D143N/A145R mutations to confer selectivity for TNFR2, and a linker between each of the THDs. In some embodiments the dimerization domain is at the N-terminus of the scTNFR2 agonist domain, while in other embodiments the dimerization domain as at the C-terminus of the molecule.

Fusion proteins disclosed herein comprise the following formulas: DD-L1-THD-L2-THD-L3-THD or THD-L2-THD-L3-THD-L1-DD, where DD is a dimerization domain as described herein. Dimerization domains are selected from IgG1, IgG2 an IgG4 Fc domains lacking effector function. In one embodiment the Fc is from IgG2 and lacking effector function. In one embodiment the Fc is from IgG4. In one embodiment the dimerization domain is EHD2 or MHD2. Then the dimerization domain is at the N-terminus of the scTNFR2 agonist protein, the linker (L1) is preferably $(GGGGS)_n$ where n=1-5(SEQ ID NO: 44), although in some embodiments the L1 linker comprises some or all of the stalk region from TNF-α. All fusion proteins of the invention disclosed herein contain THD with the TNFR2 agonist selective sequences D143N/A145R and are referred to below as THD. Linkers (L2 and L3) between the first and second, and second and third THD may also be constructed from GGGGS (SEQ ID NO: 25), G/S linkers or from some or all of the stalk region. When the dimerization domain is at the C-terminus of the scTNFR2 agonist protein there may not be a linker, or the linker may comprise $(GGGGS)_n$ where n=1-5 (SEQ ID NO: 44). Preferred configurations of fusion proteins include:

DD-L1-THD-L2-THD-L3-THD, wherein DD is the IgG4 Fc with mutation(s) eliminating effector function, L1, L2 and L3 are GGGGS (SEQ ID NO: 25);

DD-L1-THD-L2-THD-L3-THD, wherein DD is the IgG4 Fc with mutation(s) eliminating effector function, L1 is GGGGSGGGGS (SEQ ID NO:27), L2 and L3 are both GGGGs (SEQ ID NO: 25);

DD-L1-THD-L2-THD-L3-THD, wherein DD is the IgG1 Fc with mutation(s) eliminating effector function, L1 is VRSSSRTPSDK (SEQ ID NO: 4), L2 and L3 are both GGGGS (SEQ ID NO: 25);

DD-L1-THD-L2-THD-L3-THD, wherein DD is the IgG1 Fc with mutation(s) eliminating effector function, L1 is VRSSSRTPSDK (SEQ ID NO:4), L2 and L3 are both SSRTPSDK (SEQ ID NO: 28);

DD-L1-THD-L2-THD-L3-THD, wherein DD is the IgG1 Fc with mutation(s) eliminating effector function, L1 is GPQREEFPRDLSLISPLAQAVRSSSRTPSDK (SEQ ID NO: 26), L2 and L3 are both GGGGS (SEQ ID NO: 25);

DD-L1-THD-L2-THD-L3-THD, wherein DD is the IgG1 Fc with mutation(s) eliminating effector function, L1 is GPQREEFPRDLSLISPLAQAVRSSSRTPSDK (SEQ ID NO: 26), L2 and L3 are both SSRTPSDK (SEQ ID NO:28);

DD-L1-THD-L2-THD-L3-THD, wherein DD is the IgG1 Fc with mutation(s) eliminating effector function, L1 is GPQREEFPRDLSLISPLAQAVRSSSRTPSDK (SEQ ID NO: 26), L2 and L3 are both VRSSSRTPSDK (SEQ ID NO: 4);

DD-L1-THD-L2-THD-L3-THD, wherein DD is the IgG1 Fc with mutation(s) eliminating effector function, L1 is GGGGSVRSSSRTPSDK (SEQ ID NO:29), L2 and L3 are both VRSSSRTPSDK (SEQ ID NO: 4);

DD-L1-THD-L2-THD-L3-THD, wherein DD is the IgG1 Fc with mutation(s) eliminating effector function, L1 is GGGGSVRSSSRTPSDK (SEQ ID NO: 29), L2 and L3 are both GGGGSSSRTPSDK (SEQ ID NO:30);

DD-L1-THD-L2-THD-L3-THD, wherein DD is the IgG1 Fc with mutations eliminating effector function, L1, L2 and L3 are GGGGS (SEQ ID NO: 25);

DD-L1-THD-L2-THD-L3-THD, wherein DD is the IgG1 Fc with mutations eliminating effector function, L1 is GGGGSGGGGS (SEQ ID NO:27), L2 and L3 are both GGGGs (SEQ ID NO: 25);

DD-L1-THD-L2-THD-L3-THD, wherein DD is the IgG1 Fc with mutations eliminating effector function, L1 is VRSSSRTPSDK (SEQ ID NO: 4), L2 and L3 are both GGGGS (SEQ ID NO: 25);

DD-L1-THD-L2-THD-L3-THD, wherein DD is the IgG1 Fc with mutations eliminating effector function, L1 is VRSSSRTPSDK (SEQ ID NO:4), L2 and L3 are both SSRTPSDK (SEQ ID NO: 28);

DD-L1-THD-L2-THD-L3-THD, wherein DD is the IgG1 Fc with mutations eliminating effector function, L1 is GPQREEFPRDLSLISPLAQAVRSSSRTPSDK (SEQ ID NO: 26), L2 and L3 are both GGGGS (SEQ ID NO: 25);

DD-L1-THD-L2-THD-L3-THD, wherein DD is the IgG1 Fc with mutations eliminating effector function, L1 is GPQREEFPRDLSLISPLAQAVRSSSRTPSDK (SEQ ID NO: 26), L2 and L3 are both SSRTPSDK (SEQ ID NO:28);

DD-L1-THD-L2-THD-L3-THD, wherein DD is the IgG1 Fc with mutations eliminating effector function, L1 is GPQREEFPRDLSLISPLAQAVRSSSRTPSDK (SEQ ID NO: 26), L2 and L3 are both VRSSSRTPSDK (SEQ ID NO: 4);

DD-L1-THD-L2-THD-L3-THD, wherein DD is the IgG1 Fc with mutations eliminating effector function, L1 is GGGGSVRSSSRTPSDK (SEQ ID NO:29), L2 and L3 are both VRSSSRTPSDK (SEQ ID NO: 4);

DD-L1-THD-L2-THD-L3-THD, wherein DD is the IgG1 Fc with mutations eliminating effector function, L1 is GGGGSVRSSSRTPSDK (SEQ ID NO: 29), L2 and L3 are both GGGGSSSRTPSDK (SEQ ID NO:30);

DD-L1-THD-L2-THD-L3-THD, wherein DD is the IgG4 Fc, L1, L2 and L3 are GGGGS (SEQ ID NO: 25);

DD-L1-THD-L2-THD-L3-THD, wherein DD is the IgG4 Fc, L1 is GGGGSGGGGS (SEQ ID NO: 27), L2 and L3 are both GGGGs (SEQ ID NO: 25);

DD-L1-THD-L2-THD-L3-THD, wherein DD is the IgG4 Fc, L1 is VRSSSRTPSDK (SEQ ID NO: 4), L2 and L3 are both GGGGS (SEQ ID NO: 25);

DD-L1-THD-L2-THD-L3-THD, wherein DD is the IgG4 Fc, L1 is VRSSSRTPSDK (SEQ ID NO: 4), L2 and L3 are both SSRTPSDK (SEQ ID NO: 28);

DD-L1-THD-L2-THD-L3-THD, wherein DD is the IgG4 Fc, L1 is GPQREEFPRDLSLISPLAQAVRSSSRTPSDK (SEQ ID NO: 26), L2 and L3 are both GGGGS (SEQ ID NO: 25);

DD-L1-THD-L2-THD-L3-THD, wherein DD is the IgG4 Fc, L1 is GPQREEFPRDLSLISPLAQAVRSSSRTPSDK (SEQ ID NO: 26), L2 and L3 are both SSRTPSDK (SEQ ID NO: 28);

DD-L1-THD-L2-THD-L3-THD, wherein DD is the IgG4 Fc, L1 is GPQREEFPRDLSLISPLAQAVRSSSRTPSDK (SEQ ID NO: 26), L2 and L3 are both VRSSSRTPSDK (SEQ ID NO: 4);

DD-L1-THD-L2-THD-L3-THD, wherein DD is the, L1 is GGGGSVRSSSRTPSDK (SEQ ID NO: 29), L2 and L3 are both VRSSSRTPSDK (SEQ ID NO: 4);

DD-L1-THD-L2-THD-L3-THD, wherein DD is the IgG4 Fc, L1 is GGGGSVRSSSRTPSDK (SEQ ID NO: 29), L2 and L3 are both GGGGSSSRTPSDK (SEQ ID NO: 30);

THD-L2-THD-L3-THD-L1-DD, wherein DD is the IgG1 Fc with mutations eliminating effector function, L1, L2 and L3 are GGGGS (SEQ ID NO: 25);

THD-L2-THD-L3-THD-L1-DD, wherein DD is the IgG1 Fc with mutations eliminating effector function, L1 is GGGGS (SEQ ID NO: 25) and L2 and L3 are SSRTPSDK (SEQ ID NO: 28);

THD-L2-THD-L3-THD-DD, wherein DD is the IgG1 Fc with mutations eliminating effector function, L2 and L3 are GGGGS (SEQ ID NO: 25) and scTNFR2 agonist domain is fused directly to DD;

THD-L2-THD-L3-THD-DD, wherein DD is the IgG1 Fc with mutations eliminating effector function, L2 and L3 are SSRTPSDK (SEQ ID NO: 28) and scTNFR2 agonist domain is fused directly to DD;

THD-L2-THD-L3-THD-DD, wherein DD is the IgG1 Fc with mutations eliminating effector function, L2 and L3 are GGGGSSSRTPSDK (SEQ ID NO: 30) and scTNFR2 agonist domain is fused directly to DD;

THD-L2-THD-L3-THD-DD, wherein DD is the IgG1 Fc with mutations eliminating effector function, L2 and L3 are VRSSSRTPSDK (SEQ ID NO: 4) and scTNFR2 agonist domain is fused directly to DD;

THD-L2-THD-L3-THD-L1-DD, wherein DD is the IgG4 Fc, L1, L2 and L3 are GGGGS (SEQ ID NO: 25);

THD-L2-THD-L3-THD-L1-DD, wherein DD is the IgG4 Fc, L1 is GGGGS (SEQ ID NO: 25) and L2 and L3 are SSRTPSDK (SEQ ID NO: 28);

THD-L2-THD-L3-THD-DD, wherein DD is the IgG4 Fc, L2 and L3 are GGGGS (SEQ ID NO: 25) and scTNFR2 agonist domain is fused directly to DD;

THD-L2-THD-L3-THD-DD, wherein DD is the IgG4 Fc, L2 and L3 are SSRTPSDK (SEQ ID NO: 28) and scTNFR2 agonist domain is fused directly to DD;

THD-L2-THD-L3-THD-DD, wherein DD is the IgG4, L2 and L3 are GGGGSSSRTPSDK (SEQ ID NO: 30) and scTNFR2 agonist domain is fused directly to DD;

THD-L2-THD-L3-THD-DD, wherein DD is the IgG4 Fc, L2 and L3 are VRSSSRTPSDK (SEQ ID NO: 4) and scTNFR2 agonist domain is fused directly to DD;

THD-L2-THD-L3-THD-L1-DD, wherein DD is the IgG4 Fc with mutation(s) eliminating effector function, L1, L2 and L3 are GGGGS (SEQ ID NO: 25);

THD-L2-THD-L3-THD-L1-DD, wherein DD is the IgG4 Fc with mutation(s) eliminating effector function, L1 is GGGGS (SEQ ID NO: 25) and L2 and L3 are SSRTPSDK;

THD-L2-THD-L3-THD-DD, wherein DD is the IgG4 Fc with mutation(s) eliminating effector function, L2 and L3 are GGGGS (SEQ ID NO: 25) and scTNFR2 agonist domain is fused directly to DD;

THD-L2-THD-L3-THD-DD, wherein DD is the IgG4 Fc with mutations eliminating effector function, L2 and L3 are SSRTPSDK (SEQ ID NO: 28) and scTNFR2 agonist domain is fused directly to DD;

THD-L2-THD-L3-THD-DD, wherein DD is the IgG4 Fc with mutations eliminating effector function, L2 and L3 are GGGGSSSRTPSDK (SEQ ID NO: 30) and scTNFR2 agonist domain is fused directly to DD;

THD-L2-THD-L3-THD-DD, wherein DD is the IgG4 Fc with mutations eliminating effector function, L2 and L3 are VRSSSRTPSDK (SEQ ID NO: 4) and scTNFR2 agonist domain is fused directly to DD.

In some embodiments, the Fc-scTNFR2 agonist fusion protein comprises the sequence as shown in SEQ ID NO:31, 32, 34, or 35. In some embodiments the Fc-scTNFR2 agonist fusion protein comprises the sequence as shown in SEQ ID NOs: 101, 102, 103, 104, 105, 106, 107, 108, 109, 110, 111, 112, 118, 119 or 120. In some embodiments the scTNFR2 agonist fusion protein comprises a protein having at least 80% or 85% or 90% or 95% or 96% or 97% or 98% or 99% identity with SEQ ID NO:31, 32, 34 or 35 or SEQ IS NOs: 101, 102, 103, 104, 105, 106, 107, 108, 109, 110, 111, 112, 118, 119 or 120. In some embodiments, the present disclosure provides a nucleic acid encoding a protein as set forth in SEQ ID NO:31, 32, 34, or 35 or a protein having at least 80% or 85% or 90% or 95% or 96% or 97% or 98% or 99% identity with SEQ ID NO:31, 32, 34 or 35 or SEQ ID NOs 101, 102, 103, 104, 105, 106, 107, 108, 109, 110, 111, 112, 118, 119 or 120. In some embodiments the nucleic acid comprises a nucleic acid sequence having at least 80% or 85% or 90% or 95% or 96% or 97% or 98% or 99% identity with SEQ ID NO:36, 37, 38 or 39. In some embodiments the nucleic acid comprises the sequence shown in SEQ ID NO: 36, 27, 28 or 39.

Bioassays

Robust and quantitative bioassays are necessary for the characterization of the biological activity of candidate proteins. These assays should measure the activation of the TNFR2 receptor, measure the downstream functional consequences of activation in Tregs, and measure therapeutically-relevant outcomes and functions of the activated Tregs. These assays can be used the measure the therapeutic activity and potency of scTNFR2 Selective Agonist molecules, and can also be used for measurement of the pharmacodynamics of an scTNFR2 Selective Agonist in animals or in humans. One assay measures the TNF-α mediated caspase activity. In cells lacking TNFR1 or when TNFR1 cannot signal, this is a measure of TNFR2 activation. Another assay for functional activation measures TNFR2 agonist stimulated proliferation of Treg cells. One of ordinary skill in the art will recognize that Treg proliferation can be measured by tritiated thymidine incorporation into purified Treg cells, by an increase in Treg cell numbers in a mixed population of cells measured by flow cytometry and the frequencies of CD4+CD25+FOXP3+ or the CD4+CD25+CD127-marker phenotypes, by increased expression in Treg cells of proliferation-associated cell cycle proteins, such as Ki-67, or by measurement of the cell division-associated dilution of a vital fluorescent dye such as carboxyfluorescein succinimidyl ester (CFSE) by flow cytometry in Treg cells. Accordingly, in some embodiments the present disclosure provides methods of stimulating or expanding Tregs. In some embodiments the fusion proteins of described herein stimulate the expansion of Tregs more potently that EHD2-TNFR2 agonist (disclosed in Dong et al. PNAS 2016).

Other assays include the Kym-1 cell viability assay disclosed in the examples. In some embodiments the disclosure provides Fc-TNFR2 agonist fusion proteins that reduce viability of Kym-1 cells following culture as described herein. In some embodiments the Fc-TNFR2 agonists reduce the viability of Kym-1 cells more than EHD2-TNFR2 agonist (disclosed in Dong et al. PNAS 2016).

Formulation

Pharmaceutical compositions of the fusion proteins of the present invention are defined as formulated for parenteral (particularly intravenous or subcutaneous) delivery according to conventional methods. In general, pharmaceutical formulations will include fusion proteins of the present invention in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in Remington: The Science and Practice of Pharmacy, Gennaro, ed., Mack Publishing Co., Easton, Pa., 19.sup.th ed., 1995.

As an illustration, pharmaceutical formulations may be supplied as a kit comprising a container that comprises fusion proteins of the present invention. Therapeutic proteins can be provided in the form of an injectable solution for single or multiple doses, as a sterile powder that will be reconstituted before injection, or as a prefilled syringe. Such a kit may further comprise written information on indications and usage of the pharmaceutical composition. Moreover, such information may include a statement that the fusion proteins of the present invention is contraindicated in patients with known hypersensitivity to fusion proteins of the present invention.

The scTNFR2 selective agonist fusion proteins of this invention can be incorporated into compositions, including pharmaceutical compositions. Such compositions typically include the protein and a pharmaceutically acceptable carrier. As used herein, the term "pharmaceutically acceptable carrier" includes, but is not limited to, saline, solvents, dispersion media, coatings, antibacterial and antifungal agents isotonic and absorption delaying agents, and the like, compatible with pharmaceutical administration. Supplementary active compounds (e.g., antibiotics) can also be incorporated into the compositions.

A pharmaceutical composition is formulated to be compatible with its intended route of administration. The scTNFR2 selective agonist fusion proteins of the invention is likely that to be administered through a parenteral route. Examples of parenteral routes of administration include, for example, intravenous, intradermal, and subcutaneous. Solutions or suspensions used for parenteral application can include the following components: a sterile diluent such as water for injection, saline solution, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The maintenance of the required particle size in the case of dispersion may be facilitated by the use of surfactants, e.g., Polysorbate or Tween. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, the scTNFR2 selective agonist fusion protein is prepared with carriers that will protect the scTNFR2 selective agonist fusion protein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques.

The pharmaceutical compositions can be included in a container, pack, or dispenser together with instructions for administration.

Administration

Fusion proteins of the present invention will preferably be administered by the parenteral route. The subcutaneous route is the preferred route, but intravenous, intramuscular, and subdermal administration can also be used. For subcutaneous or intramuscular routes, depots and depot formulations can be used. For certain diseases specialized routes of administration can be used. For instance, for eye diseases, such as but not limited to optic neuritis, intraocular injection can be used. Fusion proteins can be used in a concentration of about 0.1 to 10 mcg/ml of total volume, although concentrations in the range of 0.01 mcg/ml to 100 mcg/ml may be used. In some embodiments peripheral administration is used to treat neurological disorders. In some embodiments intrathecal administration is used, which can deliver the fusion proteins into the spinal fluid which can bypass the blood brain barrier.

Determination of dose is within the level of ordinary skill in the art. Dosing is daily or weekly over the period of treatment, or may be at another intermittent frequency. Intravenous administration will be by bolus injection or infusion over a typical period of one to several hours. Sustained release formulations can also be employed. In general, a therapeutically effective amount of fusion proteins of the present invention is an amount sufficient to produce a clinically significant change in the treated condition, such as a clinically significant change in circulating Treg cells, a clinically significant change in Treg cells present within a diseased tissue, or a clinically significant change in a disease symptom.

The data obtained from the cell culture assays and animal studies can be used in formulating a range of dosage for use in humans. The dosage of such compounds lies preferably within a range of circulating concentrations that include the half maximal effective concentration ($EC_{50}$; i.e., the concentration of the test compound which achieves a half-maximal stimulation of Treg cells) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $EC_{50}$ as determined in cell culture. Such information can be used to more accurately determine useful doses in humans. Levels in plasma may be measured, for example, by enzyme-linked immunosorbent assays.

As defined herein, a therapeutically effective amount of a scTNFR2 selective agonist fusion protein (i.e., an effective dosage) depends on the polypeptide selected and the dose frequency. For instance, single dose amounts in the range of approximately 0.01 to 50 mg/kg of patient body weight can be administered; in some embodiments, about 0.05 to 10 mg/kg, or 0.1 to 25 mg/kg of patient body weight can be administered; in some embodiments about 0.5 to 10 mg/kg of patient body weight can be administered. In some embodiments about 0.1 mg/kg, 0.5 mg/kg, 1 mg/kg, 2.5 mg/kg, 5 mg/kg, 7.5 mg/kg, 10 mg/kg, or 20 mg/kg or 40 mg/kg or 50 mg/kg of patient body can be administered. In some embodiments, for instance when intraocular administration is used, the concentration per patient body weight is in appropriate measure to use. Rather, a total of 0.5 mg, or 1 mg or 1.5 mg or 2 mg or 2.5 mg or 3 mg or 3.5 mg or 4 mg or 5 mg of fusion protein are administered in each eye. The compositions can be administered from one time per day to one or more times per week, or one or more times per month; including once every other day, or twice a week or twice a month. The skilled artisan will appreciate that certain factors may influence the dosage and timing required to effectively treat a subject, including but not limited to the severity of the disease or disorder, previous treatments, the general health and/or age of the subject, the level of Treg cells present in the patient, and other diseases present. Moreover, treatment of a subject with a therapeutically effective amount of the TNFR2 selective agonist fusion protein of the invention is likely to be a series of treatments.

Diseases

Some of the diseases that can benefit from the therapy of this invention have been noted. However, the role of Treg cells in autoimmune diseases is a very active area of research, and additional diseases will likely be identified as treatable by this invention. Autoimmune diseases are defined as human diseases in which the immune system attacks its own proteins, cells, and tissues. A comprehensive listing and review of autoimmune diseases can be found in The Autoimmune Diseases (Rose and Mackay, 2014, Academic Press).

As disclosed herein, even when administered peripherally, scTNFR2 agonist proteins may be used to treat neurological disorders, particularly those characterized by elevated TNF-α. In one embodiment the scTNFR2 molecules disclosed herein find use in treating neurological disorders, e.g., by reducing inflammation in the brain, protecting myelination of neurons and/or promoting remyelination of neurons. Accordingly, neurological disorders particularly amenable to the methods disclosed herein include art-recognized inflammatory neurodegenerative diseases, which may result in the destruction of myelin or may include other neurological disorders not necessarily characterized by myelin destruction but are characterized by elevated levels of TNF-α L.

In one embodiment, neurodegenerative diseases are a group of diseases typified by deterioration of neurons and/or their myelin sheath. This destruction of neurons eventually leads to dysfunction and disabilities. Often inflammation, thought to be mediated by microglial cells, is found to be a component of neurodegenerative diseases and adds to the pathogenesis of the neurodegeneration. Collectively, these diseases comprise the art-recognized neurodegenerative diseases. Neuroinflammation may occur years prior to any considerable loss of neurons in some neurodegenerative disorders. For example, 70% of dopaminergic neurons are lost from the substantia nigra before patients begin to manifest the clinical signs of Parkinson's disease, see, e.g., Factor and Weiner (2008) Parkinson's Disease: Diagnosis and Clinical Management. Many different types of immune cells, including macrophages, neutrophils, T cells, astrocytes, and microglia, can contributed to the pathology of immune-related diseases, like Multiple Sclerosis (M.S.), Parkinson's disease, Huntington's disease, dementia (including but not exclusively diseases like Alzheimer's disease, frontotemporal dementia, trauma related dementia (punch drunk), HIV-associated and Lewy Body dementia), amyotrophic lateral sclerosis (ALS), prion diseases, etc. More specifically, in MS the injury to myelin is mediated by an inflammatory response and M.S. Pathogenesis is exacerbated when leukocytes infiltrate the CNS.

Accordingly, neurodegenerative diseases include but are not limited to: multiple sclerosis (MS), Optic Neuritis, Parkinson's disease, amyloidosis (e.g., Alzheimer's disease), amyotrophic lateral sclerosis (ALS), HIV-associated dementia, stroke/cerebral ischemia, head trauma, spinal cord injury, Huntington's disease, migraine, cerebral amyloid angiopathy, AIDS, age-related cognitive decline; mild cognitive impairment and prion diseases in a mammal, and preferably in a human.

Multiple sclerosis (MS) is a chronic inflammatory neurodegenerative disease of the central nervous system (CNS) that affects approximately 1,100,000 people all over the world, in particular affects young adults. MS is characterized pathologically by demyelination of neural tissue, which results clinically in one of many forms of the disease, ranging from benign to chronic-progressive patterns of the disease state. More specifically, five main forms of multiple sclerosis have been described: 1) benign multiple sclerosis; 2) relapsing-remitting multiple sclerosis (RRMS); 3) secondary progressive multiple sclerosis (SPMS); 4) primary progressive multiple sclerosis (PPMS); and 5) progressive-relapsing multiple sclerosis (PRMS). Chronic progressive multiple sclerosis is a term used to collectively refer to SPMS, PPMS, and PRMS. The relapsing forms of multiple sclerosis are SPMS with superimposed relapses, RRMS and PRMS.

Throughout the course of the disease there is a progressive destruction of the myelin sheath surrounding axons. Since intact myelin is essential in the preservation of axonal integrity systematic destruction eventually leads, clinically, to various neurological dysfunctions including numbness and pain, problems with coordination and balance, blindness, and general cognitive impairment.

Parkinson's disease, another inflammatory neurodegenerative disease, is characterized by movement disorders, including muscle rigidity and slow physical movements.

Amyloidosis develops when certain proteins have altered structure and tend to bind to each building up in particular tissue and blocking the normal tissue functioning. These altered structured proteins are called amyloids. Often amyloidoses is split into two categories: primary or secondary. Primary amyloidoses occur from an illness with improper immune cell function. Secondary amyloidoses usually arise from a complication of some other chronic infectious or inflammatory diseases. Examples of such include Alzheimer's disease and rheumatoid arthritis. The underlying problem in secondary amyloidosis is inflammation.

Alzheimer's disease is another type of inflammatory neurodegenerative disease. It is exemplified by the increasing impairment of learning and memory, although the disease may manifest itself in other ways indicating altered cognitive ability. Throughout the disease the progressive loss of neurons and synapses in the cerebral cortex leads to gross atrophy of the neural tissue. Although the cause of Alzheimer's is unknown, many believe that inflammation plays an important role and clinical studies have shown that inflammation considerably contributes to the pathogenesis of the disease.

Amyotrophic lateral sclerosis is another debilitating neurological disorder. In ALS a link between inflammation and the disease has been suggested.

In one embodiment, the neurological disorder is any disorder characterized by elevated TNF-α, and can include disorders such as stroke, depression, post-traumatic stress syndrome and traumatic brain injury.

In some embodiments, the disorders that can be treated by the scTNFR2 fusion proteins described herein include demyelinating disorders, such as but not limited to multiple sclerosis (MS), including primary progressive or relapsing-remitting MS, or optic neuritis. Other disorders such as, but not limited to, pain, which may include neuropathic pain, may be treated with the TNFR2 agonists described herein.

Other Fusion Proteins

Because the purpose of the Fc protein moiety in this invention is solely to increase circulating half-life, one skilled in the art will recognize that the scTNFR2 selective agonist moiety could be fused to the N-terminus of other proteins to achieve the same goal of increasing molecular size and reducing the rate of renal clearance, using the structure-activity relationships discovered in this invention. The scTNFR2 selective agonist could be fused to the N-terminus of serum albumin (Sleep. D., et al., 2013, Biochim Biophys Acta.1830:5526-34), which both increases the hydrodynamic radius of the fusion protein relative to the TNFR2 moiety and is also recycled by the FcRN. A skilled artisan would also recognize that the scTNFR2 selective agonist moiety of this invention could also be fused to the N-terminus of recombinant non-immunogenic amino acid polymers. Two examples of non-immunogenic amino acid polymers developed for this purpose are XTEN polymers, chains of A, E, G, P, S, and T amino acids (Schellenberger, V., et. al., 2009, Nat Biotechnol. 27:1186-90)), and PAS polymers, chains of P, A, and S amino acid residues (Schlapschy, M., et. al., 2007, Protein Eng Des Scl. 20:273-84).

Combination Treatments

Treatments that currently are available for MS include glatiramer acetate, interferonβ, natalizumab, and mitoxanthrone. In general, these drugs suppress the immune system in a nonspecific fashion and only marginally limit the overall progression of disease. (Lubetzki et al. (2005), Curr. Opin. Neurol. 18:237-244). Thus, there exists a need for developing therapeutic strategies to better treat MS. As described herein, scTNFR2 find use in treating MS. These molecules find particular use when combined with currently available MS therapies as known in the art and as described herein. For instance, scTNFR2 agonists may be combined in a therapeutic regimen with glatiramer acetate, interferon-β, natalizumab, and mitoxanthron or other molecules, such as bardoxolone methyl or variants thereof.

As another example, in the treatment of Alzheimer's Disease (AD), a scTNFR2 agonist protein may be administered to an individual in combination therapy with one or more additional therapeutic agents for the treatment of AD. Suitable additional therapeutic agents include, but are not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept is generally administered at 50 mg orally per day for 6 weeks, and, if well tolerated by the individual, at 10 mg per day thereafter.

In one embodiment, treatment of the scTNFR2 agonist in a therapeutic regimen in combination with the co-therapies as described herein results in synergistic efficacy as compared to either of the treatments alone. By "synergistic" is meant that efficacy is more than the result of additive efficacy of the two treatments alone.

In one embodiment treatment of the scTNFR2 agonist in a therapeutic regimen includes the combination of steroidal anti-inflammatory molecules, such as but not limited to dexamethasone and the like or non-steroidal anti-inflammatory molecules.

In addition, the scTNFR2 agonist may be formulated alone as a topical therapy or used in combination with or treated in a regimen with corticosteroids for treatment of autoimmune skin disorders such as psoriasis, eczema and burns (including sunburn). For instance, bath solutions and moisturizers, mineral oil and petroleum jelly which may help soothe the affected skin and reduce the dryness which accompanies the build-up of skin on psoriatic plaques may be used formulated with or in a therapeutic regimen with scTNFR2 agonist as described herein. In addition, medicated creams and ointments applied directly to psoriatic plaques can help reduce inflammation, remove built-up scale, reduce skin turn over, and clear affected skin of plaques. Ointment and creams containing coal, tar, dithranol (anthralin), corticosteroids like desoximetasone (Topicort), fluocinonide, vitamin D3 analogs (for example, calcipotriol), and retinoids find use when combined with scTNFR2 agonist for topical application to the skin for treatment of autoimmune skin disorders.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation and Characterization of TNFR2 Selective Agonist

Example 1 Expression of TNFR2 Agonist Molecules

TNFR2-selective TNF variants, which are composed of a covalently stabilized human TNFR2-selective (D143N/

A145R) single-chain TNF (scTNF$_{R2}$) were fused to Fc dimerization domains resulting in a protein that is, with respect to TNF domains, hexameric (Fc-scTNF$_{R2}$). The purity of the recombinant proteins was confirmed by SDS/PAGE and immunoblot analysis. Under reducing conditions, the TNF variants exhibited an appropriate molecular mass. Under nonreducing conditions the expected dimer was observed. The oligomerization state of Fc-scTNFR2 was further characterized by capillary electrophoresis. Fc-scTNFR2 elutes as a single major peak, indicating high purity. An exemplary electropherogram is shown in FIG. 1 for SEQ ID NO:101.

Each gene sequence was cloned into a high expression mammalian vector. Each completed construct was sequence confirmed before proceeding to DNA scale up. Each DNA expression construct was scaled up to the appropriate amount for transfection. The plasmid DNA was run on agarose gel for quality assessment and sequence confirmed before proceeding to transfection. Suspension HEK293 cells were seeded in a shake flask and were expanded using serum-free chemically defined medium. On the day of transfection, the expanded cells were seeded into a new flask with fresh medium. Each DNA construct was transiently transfected into HEK293 cells using standard methods. The cells were maintained as a batch-fed culture until the end of the production run. The conditioned media from the transient production run was harvested and clarified by centrifugation and filtration. The supernatant was loaded over a Protein A column pre-equilibrated with binding buffer. Washing buffer was passed through the column until the OD280 value (NanoDrop, Thermo Scientific) was measured to be zero. The target protein was eluted with a low pH buffer, fractions were collected, and the OD280 value of each fraction was recorded. Fractions containing the target protein were pooled and filtered through a 0.2 μm membrane filter. The protein concentration was calculated from the OD280 value and the calculated extinction coefficient. CE-SDS analysis of the target protein was performed using LabChip GXII (Perkin Elmer).

Example 2 TNFR2 Binding

TNF receptor selectivity of Fc-scTNFR2 is analyzed by binding studies with immobilized huTNFR1-Fc and huTNFR2-Fc fusion proteins. Fc-scTNFR2 does not interact with huTNFR1, but the fusion protein efficiently binds to huTNFR2. In contrast, soluble human TNF (huTNF) efficiently binds to huTNFR1, whereas it less effectively with huTNFR2.

Wells were coated with 1 μg/mL hTNFR1-Fc or hTNFR2-Fc in PBS, 4° C. overnight then blocked with 3% milk in PBS, RT 1.5 hours. Primary incubation: TNF variant proteins, RT 1 hour (starting from 60 nM, 1:3 dilution). Primary detection antibody: 1 ug/mL TNF alpha monoclonal antibody (F6C5), RT 1 hour. Secondary detection antibody: HRP conjugated goat anti-mouse antibody (1:5000 dilution), RT 1 hour. Data shown in FIG. 2. Calculated binding affinity follows:

| TNF Variant | Kd (nM) |
|---|---|
| Binding to TNFR1 | |
| TNF-α | 1.12 |
| SEQ ID NO:101 | n/a |
| SEQ ID NO:102 | n/a |
| EHD-scTNFr2 | n/a |
| SEQ ID NO:113 | n/a |
| SEQ ID NO:114 | Did not express |
| SEQ ID NO:115 | n/a |
| SEQ ID NO:116 | n/a |
| SEQ ID NO:117 | n/a |
| IgG4 Control | n/a |
| Binding to TNFR2 | |
| TNF-α | 0.90 |
| SEQ ID NO:101 | 0.44 |
| SEQ ID NO:102 | 0.27 |
| EHD-scTNFr2 | 0.33 |
| SEQ ID NO:113 | 0.21 |
| SEQ ID NO:114 | Did not express |
| SEQ ID NO:115 | 0.28 |
| SEQ ID NO:116 | 0.30 |
| SEQ ID NO:117 | n/a |
| IgG4 Control | n/a |

Example 3 Cell Based TNFR2 Assay

Fc-scTNFR2 does not activate TNFR1-dependent cell death in L929, verifying that Fc-scTNFR2 had lost affinity for TNFR1 due to the mutations D143N/A145R. In contrast, Fc-scTNFR2 efficiently induced cell death in Kym-1 cells, which endogenously express both TNF receptors and are highly sensitive to endogenous TNF-induced TNFR1 mediated cytotoxicity. Thus, TNFR2 signaling can be measured as an increase in cell death in Kym-1 cells.

Kym-1 cells (1.5×104 cells/well) were grown in 96-well white opaque cell culture plates (Perkin Elmer) overnight. The cells were incubated with 8 concentrations of TNF muteins (100, 10, 1, 0.1, 0.01, 0.001, 0.0001 and 0.00001 ng/mL) in triplicates for 24 h at 37° C. and 5% CO2. Cell viability was analyzed at 24 h by Cell Titer Glo assay (Promega). SEQ ID NO:114 did not express and therefore could not be tested. SEQ ID NO:117 did not induce cell death under any concentrations consistent with its inability to bind TNFR2 as shown in Example 2.

The invention claimed is:

1. A fusion protein comprising SEQ ID NO: 31, SEQ ID NO:32, SEQ ID NO:34 or SEQ ID NO:35.

2. A fusion protein comprising a sequence selected from the group consisting of SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:115, SEQ ID NO:116, SEQ ID NO:118, SEQ ID NO:119 and SEQ ID NO:120.

3. A pharmaceutical composition comprising the fusion protein of claim 2.

4. The pharmaceutical composition of claim 3, wherein the fusion protein comprises the sequence of SEQ ID NO:107.

5. The pharmaceutical composition of claim 3, wherein the fusion protein comprises the sequence of SEQ ID NO:110.

6. The pharmaceutical composition of claim 3, wherein the fusion protein comprises the sequence of SEQ ID NO:113.

7. The pharmaceutical composition of claim 3, wherein the fusion protein comprises the sequence of SEQ ID NO:115.

8. The pharmaceutical composition of claim 3, wherein the fusion protein consists of the sequence of SEQ ID NO:107.

9. The pharmaceutical composition of claim 3, wherein the fusion protein consists of the sequence of SEQ ID NO:110.

10. The pharmaceutical composition of claim 3, wherein the fusion protein consists of the sequence of SEQ ID NO:113.

11. The pharmaceutical composition of claim 3, wherein the fusion protein consists of the sequence of SEQ ID NO:115.

12. A dimerized polypeptide comprising two fusion proteins according to claim 2.

13. The fusion protein according to claim 2, wherein the fusion protein comprises the sequence of SEQ ID NO: 107.

14. The fusion protein according to claim 2, wherein the fusion protein comprises the sequence of SEQ ID NO: 110.

15. The fusion protein according to claim 2, wherein the fusion protein comprises the sequence of SEQ ID NO: 113.

16. The fusion protein according to claim 2, wherein the fusion protein comprises the sequence of SEQ ID NO: 115.

17. The fusion protein according to claim 2, wherein the fusion protein consists of the sequence of SEQ ID NO: 107.

18. The fusion protein according to claim 2, wherein the fusion protein consists of the sequence of SEQ ID NO: 110.

19. The fusion protein according to claim 2, wherein the fusion protein consists of the sequence of SEQ ID NO: 113.

20. The fusion protein according to claim 2, wherein the fusion protein consists of the sequence of SEQ ID NO: 115.

* * * * *

SEQUENCE LISTING

```
<160> NUMBER OF SEQ ID NOS: 140

<210> SEQ ID NO 1
<211> LENGTH: 233
<212> TYPE: PRT
<213> ORGANISM: Homo sapiens
<220> FEATURE:
<221> NAME/KEY: misc_feature
<222> LOCATION: (1)..(233)
<223> OTHER INFORMATION: Full length TNF-alpha
```

<400> SEQUENCE: 1

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 2
<211> LENGTH: 157
<212> TYPE: PRT
<213> ORGANISM: Homo sapiens
<220> FEATURE:
<221> NAME/KEY: misc_feature
<222> LOCATION: (1)..(157)
<223> OTHER INFORMATION: Soluble TNF-alpha

<400> SEQUENCE: 2

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110
```

```
Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155


<210> SEQ ID NO 3
<211> LENGTH: 146
<212> TYPE: PRT
<213> ORGANISM: Homo sapiens
<220> FEATURE:
<221> NAME/KEY: misc_feature
<222> LOCATION: (1)..(146)
<223> OTHER INFORMATION: THD Domain with TNFR2 Agonist Sequences

<400> SEQUENCE: 3

Pro Val Ala His Val Val Ala Asn Pro Gln Ala Glu Gly Gln Leu Gln
1               5                   10                  15

Trp Leu Asn Arg Arg Ala Asn Ala Leu Leu Ala Asn Gly Val Glu Leu
            20                  25                  30

Arg Asp Asn Gln Leu Val Val Pro Ser Glu Gly Leu Tyr Leu Ile Tyr
        35                  40                  45

Ser Gln Val Leu Phe Lys Gly Gln Gly Cys Pro Ser Thr His Val Leu
    50                  55                  60

Leu Thr His Thr Ile Ser Arg Ile Ala Val Ser Tyr Gln Thr Lys Val
65                  70                  75                  80

Asn Leu Leu Ser Ala Ile Lys Ser Pro Cys Gln Arg Glu Thr Pro Glu
                85                  90                  95

Gly Ala Glu Ala Lys Pro Trp Tyr Glu Pro Ile Tyr Leu Gly Gly Val
            100                 105                 110

Phe Gln Leu Glu Lys Gly Asp Arg Leu Ser Ala Glu Ile Asn Arg Pro
        115                 120                 125

Asp Tyr Leu Asn Phe Arg Glu Ser Gly Gln Val Tyr Phe Gly Ile Ile
    130                 135                 140

Ala Leu
145


<210> SEQ ID NO 4
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Sequence from the ADAM17 cleavage site in the
      stalk region to the C-terminus of the stalk region

<400> SEQUENCE: 4

Val Arg Ser Ser Ser Arg Thr Pro Ser Asp Lys
1               5                   10


<210> SEQ ID NO 5
<211> LENGTH: 232
<212> TYPE: PRT
<213> ORGANISM: Homo sapiens
<220> FEATURE:
<221> NAME/KEY: misc_feature
<222> LOCATION: (1)..(232)
<223> OTHER INFORMATION: Human IgG1 Fc

<400> SEQUENCE: 5
```

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 6
<211> LENGTH: 232
<212> TYPE: PRT
<213> ORGANISM: Homo sapiens
<220> FEATURE:
<221> NAME/KEY: misc_feature
<222> LOCATION: (1)..(232)
<223> OTHER INFORMATION: Human IgG1 Fc with FcyR and C1q knockout

<400> SEQUENCE: 6

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 7
<211> LENGTH: 237
<212> TYPE: PRT
<213> ORGANISM: Homo sapiens
<220> FEATURE:
<221> NAME/KEY: misc_feature
<222> LOCATION: (1)..(237)
<223> OTHER INFORMATION: Human IgG1 Fc with N-terminal linker

<400> SEQUENCE: 7

Gly Gly Gly Gly Ser Glu Pro Lys Ser Cys Asp Lys Thr His Thr Cys
1               5                   10                  15

Pro Pro Cys Pro Ala Pro Glu Leu Leu Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
```

225 230 235

<210> SEQ ID NO 8
<211> LENGTH: 237
<212> TYPE: PRT
<213> ORGANISM: Homo sapiens
<220> FEATURE:
<221> NAME/KEY: misc_feature
<222> LOCATION: (1)..(237)
<223> OTHER INFORMATION: Human IgG1 Fc with FcyR and C1q knockout and linker

<400> SEQUENCE: 8

```
Gly Gly Gly Gly Ser Glu Pro Lys Ser Ser Asp Lys Thr His Thr Cys
1               5                   10                  15

Pro Pro Cys Pro Ala Pro Glu Ala Ala Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Ser Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235
```

<210> SEQ ID NO 9
<211> LENGTH: 255
<212> TYPE: PRT
<213> ORGANISM: Homo sapiens
<220> FEATURE:
<221> NAME/KEY: misc_feature
<222> LOCATION: (1)..(255)
<223> OTHER INFORMATION: Human IgG1 Fc with C-terminal linker
<220> FEATURE:
<221> NAME/KEY: misc_feature
<222> LOCATION: (231)..(255)
<223> OTHER INFORMATION: Gly Gly Gly Gly Ser is present at least one time and may repeat up to five times

<400> SEQUENCE: 9

```
Glu Pro Lys Ser Cys Asp Lys Thr His Thr Cys Pro Pro Cys Pro Ala
1               5                   10                  15
```

```
Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Gly Gly Gly Gly Ser
225                 230                 235                 240

Gly Gly Gly Gly Ser Gly Gly Gly Gly Ser Gly Gly Gly Gly Ser
                245                 250                 255


<210> SEQ ID NO 10
<211> LENGTH: 255
<212> TYPE: PRT
<213> ORGANISM: Homo sapiens
<220> FEATURE:
<221> NAME/KEY: misc_feature
<222> LOCATION: (1)..(255)
<223> OTHER INFORMATION: Human IgG1 Fc with FcyR and C1q knockout and
      C-terminal linker
<220> FEATURE:
<221> NAME/KEY: misc_feature
<222> LOCATION: (231)..(255)
<223> OTHER INFORMATION: Gly Gly Gly Gly Ser is present at least one
      time and may repeat up to five times

<400> SEQUENCE: 10

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

```
Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Gly Gly Gly Gly Ser
225                 230                 235                 240

Gly Gly Gly Gly Ser Gly Gly Gly Gly Ser Gly Gly Gly Gly Ser
                245                 250                 255


<210> SEQ ID NO 11
<211> LENGTH: 229
<212> TYPE: PRT
<213> ORGANISM: Homo sapiens
<220> FEATURE:
<221> NAME/KEY: misc_feature
<222> LOCATION: (1)..(229)
<223> OTHER INFORMATION: Human IgG4 Fc

<400> SEQUENCE: 11

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
```

```
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 12
<211> LENGTH: 229
<212> TYPE: PRT
<213> ORGANISM: Homo sapiens
<220> FEATURE:
<221> NAME/KEY: misc_feature
<222> LOCATION: (1)..(229)
<223> OTHER INFORMATION: Human IgG4 Fc with Ser to Pro mutation

<400> SEQUENCE: 12

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 13
<211> LENGTH: 234
<212> TYPE: PRT
<213> ORGANISM: Homo sapiens
<220> FEATURE:
<221> NAME/KEY: misc_feature
<222> LOCATION: (1)..(234)
<223> OTHER INFORMATION: Human IgG4 Fc with N-terminal linker

<400> SEQUENCE: 13
```

```
Gly Gly Gly Gly Ser Glu Ser Lys Tyr Gly Pro Pro Cys Pro Ser Cys
1               5                   10                  15

Pro Ala Pro Glu Phe Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser Gln Glu Asp Pro Glu Val Gln Phe Asn Trp
    50                  55                  60

Tyr Val Asp Gly Val Glu Val His Asn Ala Lys Thr Lys Pro Arg Glu
65                  70                  75                  80

Glu Gln Phe Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Gly Leu Pro Ser Ser Ile Glu Lys Thr Ile Ser Lys Ala Lys Gly
        115                 120                 125

Gln Pro Arg Glu Pro Gln Val Tyr Thr Leu Pro Pro Ser Gln Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Arg Leu Thr Val Asp Lys Ser Arg Trp Gln Glu Gly Asn
        195                 200                 205

Val Phe Ser Cys Ser Val Met His Glu Ala Leu His Asn His Tyr Thr
    210                 215                 220

Gln Lys Ser Leu Ser Leu Ser Leu Gly Lys
225                 230
```

<210> SEQ ID NO 14
<211> LENGTH: 234
<212> TYPE: PRT
<213> ORGANISM: Homo sapiens
<220> FEATURE:
<221> NAME/KEY: misc_feature
<222> LOCATION: (1)..(234)
<223> OTHER INFORMATION: Human IgG4 Fc with Ser to Pro Mutation and N-terminal linker

<400> SEQUENCE: 14

```
Gly Gly Gly Gly Ser Glu Ser Lys Tyr Gly Pro Pro Cys Pro Pro Cys
1               5                   10                  15

Pro Ala Pro Glu Phe Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser Gln Glu Asp Pro Glu Val Gln Phe Asn Trp
    50                  55                  60

Tyr Val Asp Gly Val Glu Val His Asn Ala Lys Thr Lys Pro Arg Glu
65                  70                  75                  80

Glu Gln Phe Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110
```

```
Lys Gly Leu Pro Ser Ser Ile Glu Lys Thr Ile Ser Lys Ala Lys Gly
        115                 120                 125

Gln Pro Arg Glu Pro Gln Val Tyr Thr Leu Pro Pro Ser Gln Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Arg Leu Thr Val Asp Lys Ser Arg Trp Gln Glu Gly Asn
        195                 200                 205

Val Phe Ser Cys Ser Val Met His Glu Ala Leu His Asn His Tyr Thr
    210                 215                 220

Gln Lys Ser Leu Ser Leu Ser Leu Gly Lys
225                 230


<210> SEQ ID NO 15
<211> LENGTH: 252
<212> TYPE: PRT
<213> ORGANISM: Homo sapiens
<220> FEATURE:
<221> NAME/KEY: misc_feature
<222> LOCATION: (1)..(252)
<223> OTHER INFORMATION: Human IgG4 Fc with C-terminal linker
<220> FEATURE:
<221> NAME/KEY: misc_feature
<222> LOCATION: (228)..(252)
<223> OTHER INFORMATION: Gly Gly Gly Gly Ser is present at least one
      time and may repeat up to five times

<400> SEQUENCE: 15

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
```

```
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Gly Ser Gly Gly Gly
225                 230                 235                 240

Gly Ser Gly Gly Gly Gly Ser Gly Gly Gly Gly Ser
                245                 250


<210> SEQ ID NO 16
<211> LENGTH: 252
<212> TYPE: PRT
<213> ORGANISM: Homo sapiens
<220> FEATURE:
<221> NAME/KEY: misc_feature
<222> LOCATION: (1)..(252)
<223> OTHER INFORMATION: Human IgG4 Fc with Ser to Pro Mutation and
      C-terminal linker
<220> FEATURE:
<221> NAME/KEY: misc_feature
<222> LOCATION: (228)..(252)
<223> OTHER INFORMATION: Gly Gly Gly Gly Ser is present at least one
      time and may repeat up to five times

<400> SEQUENCE: 16

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Gly Ser Gly Gly Gly
225                 230                 235                 240

Gly Ser Gly Gly Gly Gly Ser Gly Gly Gly Gly Ser
                245                 250


<210> SEQ ID NO 17
```

<211> LENGTH: 228
<212> TYPE: PRT
<213> ORGANISM: Homo sapiens
<220> FEATURE:
<221> NAME/KEY: misc_feature
<222> LOCATION: (1)..(228)
<223> OTHER INFORMATION: Human IgG2 Fc

<400> SEQUENCE: 17

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 18
<211> LENGTH: 228
<212> TYPE: PRT
<213> ORGANISM: Homo sapiens
<220> FEATURE:
<221> NAME/KEY: misc_feature
<222> LOCATION: (1)..(228)
<223> OTHER INFORMATION: Human IgG2 Fc with C1q knockout

<400> SEQUENCE: 18

```
Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60
```

```
Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Ser
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225


<210> SEQ ID NO 19
<211> LENGTH: 233
<212> TYPE: PRT
<213> ORGANISM: Homo sapiens
<220> FEATURE:
<221> NAME/KEY: misc_feature
<222> LOCATION: (1)..(233)
<223> OTHER INFORMATION: Human IgG2 Fc with N-terminal linker

<400> SEQUENCE: 19

Gly Gly Gly Gly Ser Glu Arg Lys Cys Cys Val Glu Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                85                  90                  95

Gln Asp Trp Leu Asn Gly Lys Glu Tyr Lys Cys Lys Val Ser Asn Lys
            100                 105                 110

Gly Leu Pro Ala Pro Ile Glu Lys Thr Ile Ser Lys Thr Lys Gly Gln
        115                 120                 125

Pro Arg Glu Pro Gln Val Tyr Thr Leu Pro Pro Ser Arg Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
```

```
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230


<210> SEQ ID NO 20
<211> LENGTH: 233
<212> TYPE: PRT
<213> ORGANISM: Homo sapiens
<220> FEATURE:
<221> NAME/KEY: misc_feature
<222> LOCATION: (1)..(233)
<223> OTHER INFORMATION: Human IgG2 Fc with C1q knockout and N-terminal
      linker

<400> SEQUENCE: 20

Gly Gly Gly Gly Ser Glu Arg Lys Ser Ser Val Glu Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                85                  90                  95

Gln Asp Trp Leu Asn Gly Lys Glu Tyr Lys Cys Lys Val Ser Asn Lys
            100                 105                 110

Gly Leu Pro Ala Ser Ile Glu Lys Thr Ile Ser Lys Thr Lys Gly Gln
        115                 120                 125

Pro Arg Glu Pro Gln Val Tyr Thr Leu Pro Pro Ser Arg Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230


<210> SEQ ID NO 21
<211> LENGTH: 251
<212> TYPE: PRT
<213> ORGANISM: Homo sapiens
<220> FEATURE:
<221> NAME/KEY: misc_feature
<222> LOCATION: (1)..(251)
<223> OTHER INFORMATION: Human IgG2 Fc with C-terminal linker
<220> FEATURE:
```

```
<221> NAME/KEY: misc_feature
<222> LOCATION: (227)..(251)
<223> OTHER INFORMATION: Gly Gly Gly Gly Ser is present at least one
      time and may repeat up to five times

<400> SEQUENCE: 21

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Gly Ser Gly Gly Gly Gly
225                 230                 235                 240

Ser Gly Gly Gly Gly Ser Gly Gly Gly Gly Ser
                245                 250


<210> SEQ ID NO 22
<211> LENGTH: 251
<212> TYPE: PRT
<213> ORGANISM: Homo sapiens
<220> FEATURE:
<221> NAME/KEY: misc_feature
<222> LOCATION: (1)..(251)
<223> OTHER INFORMATION: Human IgG2 Fc with C1q knockout and C-terminal
      linker
<220> FEATURE:
<221> NAME/KEY: misc_feature
<222> LOCATION: (227)..(251)
<223> OTHER INFORMATION: Gly Gly Gly Gly Ser is present at least one
      time and may repeat up to five times

<400> SEQUENCE: 22

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30
```

```
Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Ser
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Gly Gly Gly Ser Gly Gly Gly Gly Ser Gly Gly Gly Gly
225                 230                 235                 240

Ser Gly Gly Gly Gly Ser Gly Gly Gly Gly Ser
                245                 250


<210> SEQ ID NO 23
<211> LENGTH: 106
<212> TYPE: PRT
<213> ORGANISM: Artificial Sequence
<220> FEATURE:
<223> OTHER INFORMATION: Synthetic: EHD2 dimerization domain

<400> SEQUENCE: 23

Asp Phe Thr Pro Pro Thr Val Lys Ile Leu Gln Ser Ser Cys Asp Gly
1               5                   10                  15

Gly Gly His Phe Pro Pro Thr Ile Gln Leu Leu Cys Leu Val Ser Gly
            20                  25                  30

Tyr Thr Pro Gly Thr Ile Asn Ile Thr Trp Leu Glu Asp Gly Gln Val
        35                  40                  45

Met Asp Val Asp Leu Ser Thr Ala Ser Thr Thr Gln Glu Gly Glu Leu
    50                  55                  60

Ala Ser Thr Gln Ser Glu Leu Thr Leu Ser Gln Lys His Trp Leu Ser
65                  70                  75                  80

Asp Arg Thr Tyr Thr Cys Gln Val Thr Tyr Gln Gly His Thr Phe Glu
                85                  90                  95

Asp Ser Thr Lys Lys Cys Ala Asp Ser Asn
            100                 105


<210> SEQ ID NO 24
<211> LENGTH: 111
<212> TYPE: PRT
<213> ORGANISM: Artificial Sequence
<220> FEATURE:
```

<223> OTHER INFORMATION: Synthetic: MHD2 dimerization domain

<400> SEQUENCE: 24

```
Ala Glu Leu Pro Pro Lys Val Ser Val Phe Val Pro Pro Arg Asp Gly
1               5                   10                  15

Phe Phe Gly Asn Pro Arg Lys Ser Lys Leu Ile Cys Gln Ala Thr Gly
            20                  25                  30

Phe Ser Pro Arg Gln Ile Gln Val Ser Trp Leu Arg Glu Gly Lys Gln
        35                  40                  45

Val Gly Ser Gly Val Thr Thr Asp Gln Val Gln Ala Glu Ala Lys Glu
    50                  55                  60

Ser Gly Pro Thr Thr Tyr Lys Val Thr Ser Thr Leu Thr Ile Lys Glu
65                  70                  75                  80

Ser Asp Trp Leu Gly Gln Ser Met Phe Thr Cys Arg Val Asp His Arg
                85                  90                  95

Gly Leu Thr Phe Gln Gln Asn Ala Ser Ser Met Cys Val Pro Asp
            100                 105                 110
```

<210> SEQ ID NO 25
<211> LENGTH: 5
<212> TYPE: PRT
<213> ORGANISM: Artificial Sequence
<220> FEATURE:
<223> OTHER INFORMATION: Synthetic: linker

<400> SEQUENCE: 25

```
Gly Gly Gly Gly Ser
1               5
```

<210> SEQ ID NO 26
<211> LENGTH: 31
<212> TYPE: PRT
<213> ORGANISM: Artificial Sequence
<220> FEATURE:
<223> OTHER INFORMATION: Synthetic: TNF-a stalk region

<400> SEQUENCE: 26

```
Gly Pro Gln Arg Glu Glu Phe Pro Arg Asp Leu Ser Leu Ile Ser Pro
1               5                   10                  15

Leu Ala Gln Ala Val Arg Ser Ser Ser Arg Thr Pro Ser Asp Lys
            20                  25                  30
```

<210> SEQ ID NO 27
<211> LENGTH: 10
<212> TYPE: PRT
<213> ORGANISM: Artificial Sequence
<220> FEATURE:
<223> OTHER INFORMATION: Synthetic: linker

<400> SEQUENCE: 27

```
Gly Gly Gly Gly Ser Gly Gly Gly Gly Ser
1               5                   10
```

<210> SEQ ID NO 28
<211> LENGTH: 8
<212> TYPE: PRT
<213> ORGANISM: Artificial Sequence
<220> FEATURE:
<223> OTHER INFORMATION: Synthetic: stalk based linker

<400> SEQUENCE: 28

```
Ser Ser Arg Thr Pro Ser Asp Lys
1               5
```

<210> SEQ ID NO 29
<211> LENGTH: 16
<212> TYPE: PRT
<213> ORGANISM: Artificial Sequence
<220> FEATURE:
<223> OTHER INFORMATION: Synthetic: G/S Stalk based linker

<400> SEQUENCE: 29

Gly Gly Gly Gly Ser Val Arg Ser Ser Ser Arg Thr Pro Ser Asp Lys
1 5 10 15

<210> SEQ ID NO 30
<211> LENGTH: 13
<212> TYPE: PRT
<213> ORGANISM: Artificial Sequence
<220> FEATURE:
<223> OTHER INFORMATION: Synthetic: G/S Stalk based linker

<400> SEQUENCE: 30

Gly Gly Gly Gly Ser Ser Ser Arg Thr Pro Ser Asp Lys
1 5 10

<210> SEQ ID NO 31
<211> LENGTH: 700
<212> TYPE: PRT
<213> ORGANISM: Artificial Sequence
<220> FEATURE:
<223> OTHER INFORMATION: Synthetic: IgG1 Fc with mutations;GGGGS2; THDR2; stalk linker; THDR2; stalk linker; THDR2

<400> SEQUENCE: 31

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

-continued

```
Ser Leu Ser Leu Ser Pro Gly Gly Gly Gly Ser Gly Gly Gly Gly Ser
225                 230                 235                 240

Pro Val Ala His Val Val Ala Asn Pro Gln Ala Glu Gly Gln Leu Gln
                245                 250                 255

Trp Leu Asn Arg Arg Ala Asn Ala Leu Leu Ala Asn Gly Val Glu Leu
            260                 265                 270

Arg Asp Asn Gln Leu Val Val Pro Ser Glu Gly Leu Tyr Leu Ile Tyr
        275                 280                 285

Ser Gln Val Leu Phe Lys Gly Gln Gly Cys Pro Ser Thr His Val Leu
    290                 295                 300

Leu Thr His Thr Ile Ser Arg Ile Ala Val Ser Tyr Gln Thr Lys Val
305                 310                 315                 320

Asn Leu Leu Ser Ala Ile Lys Ser Pro Cys Gln Arg Glu Thr Pro Glu
                325                 330                 335

Gly Ala Glu Ala Lys Pro Trp Tyr Glu Pro Ile Tyr Leu Gly Gly Val
            340                 345                 350

Phe Gln Leu Glu Lys Gly Asp Arg Leu Ser Ala Glu Ile Asn Arg Pro
        355                 360                 365

Asp Tyr Leu Asn Phe Arg Glu Ser Gly Gln Val Tyr Phe Gly Ile Ile
    370                 375                 380

Ala Leu Val Arg Ser Ser Ser Arg Thr Pro Ser Asp Lys Pro Val Ala
385                 390                 395                 400

His Val Val Ala Asn Pro Gln Ala Glu Gly Gln Leu Gln Trp Leu Asn
                405                 410                 415

Arg Arg Ala Asn Ala Leu Leu Ala Asn Gly Val Glu Leu Arg Asp Asn
            420                 425                 430

Gln Leu Val Val Pro Ser Glu Gly Leu Tyr Leu Ile Tyr Ser Gln Val
        435                 440                 445

Leu Phe Lys Gly Gln Gly Cys Pro Ser Thr His Val Leu Leu Thr His
    450                 455                 460

Thr Ile Ser Arg Ile Ala Val Ser Tyr Gln Thr Lys Val Asn Leu Leu
465                 470                 475                 480

Ser Ala Ile Lys Ser Pro Cys Gln Arg Glu Thr Pro Glu Gly Ala Glu
                485                 490                 495

Ala Lys Pro Trp Tyr Glu Pro Ile Tyr Leu Gly Gly Val Phe Gln Leu
            500                 505                 510

Glu Lys Gly Asp Arg Leu Ser Ala Glu Ile Asn Arg Pro Asp Tyr Leu
        515                 520                 525

Asn Phe Arg Glu Ser Gly Gln Val Tyr Phe Gly Ile Ile Ala Leu Val
    530                 535                 540

Arg Ser Ser Ser Arg Thr Pro Ser Asp Lys Pro Val Ala His Val Val
545                 550                 555                 560

Ala Asn Pro Gln Ala Glu Gly Gln Leu Gln Trp Leu Asn Arg Arg Ala
                565                 570                 575

Asn Ala Leu Leu Ala Asn Gly Val Glu Leu Arg Asp Asn Gln Leu Val
            580                 585                 590

Val Pro Ser Glu Gly Leu Tyr Leu Ile Tyr Ser Gln Val Leu Phe Lys
        595                 600                 605

Gly Gln Gly Cys Pro Ser Thr His Val Leu Leu Thr His Thr Ile Ser
    610                 615                 620

Arg Ile Ala Val Ser Tyr Gln Thr Lys Val Asn Leu Leu Ser Ala Ile
625                 630                 635                 640
```

```
Lys Ser Pro Cys Gln Arg Glu Thr Pro Glu Gly Ala Glu Ala Lys Pro
                645                 650                 655

Trp Tyr Glu Pro Ile Tyr Leu Gly Gly Val Phe Gln Leu Glu Lys Gly
            660                 665                 670

Asp Arg Leu Ser Ala Glu Ile Asn Arg Pro Asp Tyr Leu Asn Phe Arg
        675                 680                 685

Glu Ser Gly Gln Val Tyr Phe Gly Ile Ile Ala Leu
    690                 695                 700


<210> SEQ ID NO 32
<211> LENGTH: 710
<212> TYPE: PRT
<213> ORGANISM: Artificial Sequence
<220> FEATURE:
<223> OTHER INFORMATION: Synthetic: IgG1 Fc with mutations; G/S stalk
      linker; THDR2; G/S short stalk linker; THDR2; G/S short stalk
      linker; THDR2

<400> SEQUENCE: 32

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Val Arg Ser Ser Ser
225                 230                 235                 240

Arg Thr Pro Ser Asp Lys Pro Val Ala His Val Val Ala Asn Pro Gln
                245                 250                 255

Ala Glu Gly Gln Leu Gln Trp Leu Asn Arg Arg Ala Asn Ala Leu Leu
            260                 265                 270

Ala Asn Gly Val Glu Leu Arg Asp Asn Gln Leu Val Val Pro Ser Glu
        275                 280                 285

Gly Leu Tyr Leu Ile Tyr Ser Gln Val Leu Phe Lys Gly Gln Gly Cys
```

```
    290                 295                 300

Pro Ser Thr His Val Leu Leu Thr His Thr Ile Ser Arg Ile Ala Val
305                 310                 315                 320

Ser Tyr Gln Thr Lys Val Asn Leu Leu Ser Ala Ile Lys Ser Pro Cys
                325                 330                 335

Gln Arg Glu Thr Pro Glu Gly Ala Glu Ala Lys Pro Trp Tyr Glu Pro
            340                 345                 350

Ile Tyr Leu Gly Gly Val Phe Gln Leu Glu Lys Gly Asp Arg Leu Ser
        355                 360                 365

Ala Glu Ile Asn Arg Pro Asp Tyr Leu Asn Phe Arg Glu Ser Gly Gln
    370                 375                 380

Val Tyr Phe Gly Ile Ile Ala Leu Gly Gly Gly Gly Ser Ser Ser Arg
385                 390                 395                 400

Thr Pro Ser Asp Lys Pro Val Ala His Val Val Ala Asn Pro Gln Ala
                405                 410                 415

Glu Gly Gln Leu Gln Trp Leu Asn Arg Arg Ala Asn Ala Leu Leu Ala
            420                 425                 430

Asn Gly Val Glu Leu Arg Asp Asn Gln Leu Val Val Pro Ser Glu Gly
        435                 440                 445

Leu Tyr Leu Ile Tyr Ser Gln Val Leu Phe Lys Gly Gln Gly Cys Pro
    450                 455                 460

Ser Thr His Val Leu Leu Thr His Thr Ile Ser Arg Ile Ala Val Ser
465                 470                 475                 480

Tyr Gln Thr Lys Val Asn Leu Leu Ser Ala Ile Lys Ser Pro Cys Gln
                485                 490                 495

Arg Glu Thr Pro Glu Gly Ala Glu Ala Lys Pro Trp Tyr Glu Pro Ile
            500                 505                 510

Tyr Leu Gly Gly Val Phe Gln Leu Glu Lys Gly Asp Arg Leu Ser Ala
        515                 520                 525

Glu Ile Asn Arg Pro Asp Tyr Leu Asn Phe Arg Glu Ser Gly Gln Val
    530                 535                 540

Tyr Phe Gly Ile Ile Ala Leu Gly Gly Gly Gly Ser Ser Ser Arg Thr
545                 550                 555                 560

Pro Ser Asp Lys Pro Val Ala His Val Val Ala Asn Pro Gln Ala Glu
                565                 570                 575

Gly Gln Leu Gln Trp Leu Asn Arg Arg Ala Asn Ala Leu Leu Ala Asn
            580                 585                 590

Gly Val Glu Leu Arg Asp Asn Gln Leu Val Val Pro Ser Glu Gly Leu
        595                 600                 605

Tyr Leu Ile Tyr Ser Gln Val Leu Phe Lys Gly Gln Gly Cys Pro Ser
    610                 615                 620

Thr His Val Leu Leu Thr His Thr Ile Ser Arg Ile Ala Val Ser Tyr
625                 630                 635                 640

Gln Thr Lys Val Asn Leu Leu Ser Ala Ile Lys Ser Pro Cys Gln Arg
                645                 650                 655

Glu Thr Pro Glu Gly Ala Glu Ala Lys Pro Trp Tyr Glu Pro Ile Tyr
            660                 665                 670

Leu Gly Gly Val Phe Gln Leu Glu Lys Gly Asp Arg Leu Ser Ala Glu
        675                 680                 685

Ile Asn Arg Pro Asp Tyr Leu Asn Phe Arg Glu Ser Gly Gln Val Tyr
    690                 695                 700

Phe Gly Ile Ile Ala Leu
705                 710
```

<210> SEQ ID NO 33
<211> LENGTH: 157
<212> TYPE: PRT
<213> ORGANISM: Artificial Sequence
<220> FEATURE:
<223> OTHER INFORMATION: Synthetic: Soluble TNF-a sequence with TNFR2 agonist mutations

<400> SEQUENCE: 33

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu
145                 150                 155
```

<210> SEQ ID NO 34
<211> LENGTH: 701
<212> TYPE: PRT
<213> ORGANISM: Artificial Sequence
<220> FEATURE:
<223> OTHER INFORMATION: Synthetic: scTNFR2 agonist with C-terminal IgG1 with mutations. This is soluble TNF-a sequence, which includes VRSSSRTPSDK at N-terminus prior to THD domain.

<400> SEQUENCE: 34

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
```

```
    130                 135                 140

Arg Glu Ser Gly Gln Val Tyr Phe Gly Ile Ile Ala Leu Val Arg Ser
145                 150                 155                 160

Ser Ser Arg Thr Pro Ser Asp Lys Pro Val Ala His Val Val Ala Asn
                165                 170                 175

Pro Gln Ala Glu Gly Gln Leu Gln Trp Leu Asn Arg Arg Ala Asn Ala
            180                 185                 190

Leu Leu Ala Asn Gly Val Glu Leu Arg Asp Asn Gln Leu Val Val Pro
        195                 200                 205

Ser Glu Gly Leu Tyr Leu Ile Tyr Ser Gln Val Leu Phe Lys Gly Gln
    210                 215                 220

Gly Cys Pro Ser Thr His Val Leu Leu Thr His Thr Ile Ser Arg Ile
225                 230                 235                 240

Ala Val Ser Tyr Gln Thr Lys Val Asn Leu Leu Ser Ala Ile Lys Ser
                245                 250                 255

Pro Cys Gln Arg Glu Thr Pro Glu Gly Ala Glu Ala Lys Pro Trp Tyr
            260                 265                 270

Glu Pro Ile Tyr Leu Gly Gly Val Phe Gln Leu Glu Lys Gly Asp Arg
        275                 280                 285

Leu Ser Ala Glu Ile Asn Arg Pro Asp Tyr Leu Asn Phe Arg Glu Ser
    290                 295                 300

Gly Gln Val Tyr Phe Gly Ile Ile Ala Leu Val Arg Ser Ser Ser Arg
305                 310                 315                 320

Thr Pro Ser Asp Lys Pro Val Ala His Val Val Ala Asn Pro Gln Ala
                325                 330                 335

Glu Gly Gln Leu Gln Trp Leu Asn Arg Arg Ala Asn Ala Leu Leu Ala
            340                 345                 350

Asn Gly Val Glu Leu Arg Asp Asn Gln Leu Val Val Pro Ser Glu Gly
        355                 360                 365

Leu Tyr Leu Ile Tyr Ser Gln Val Leu Phe Lys Gly Gln Gly Cys Pro
    370                 375                 380

Ser Thr His Val Leu Leu Thr His Thr Ile Ser Arg Ile Ala Val Ser
385                 390                 395                 400

Tyr Gln Thr Lys Val Asn Leu Leu Ser Ala Ile Lys Ser Pro Cys Gln
                405                 410                 415

Arg Glu Thr Pro Glu Gly Ala Glu Ala Lys Pro Trp Tyr Glu Pro Ile
            420                 425                 430

Tyr Leu Gly Gly Val Phe Gln Leu Glu Lys Gly Asp Arg Leu Ser Ala
        435                 440                 445

Glu Ile Asn Arg Pro Asp Tyr Leu Asn Phe Arg Glu Ser Gly Gln Val
    450                 455                 460

Tyr Phe Gly Ile Ile Ala Leu Glu Pro Lys Ser Ser Asp Lys Thr His
465                 470                 475                 480

Thr Cys Pro Pro Cys Pro Ala Pro Glu Ala Ala Gly Gly Pro Ser Val
                485                 490                 495

Phe Leu Phe Pro Pro Lys Pro Lys Asp Thr Leu Met Ile Ser Arg Thr
            500                 505                 510

Pro Glu Val Thr Cys Val Val Val Asp Val Ser His Glu Asp Pro Glu
        515                 520                 525

Val Lys Phe Asn Trp Tyr Val Asp Gly Val Glu Val His Asn Ala Lys
    530                 535                 540

Thr Lys Pro Arg Glu Glu Gln Tyr Asn Ser Thr Tyr Arg Val Val Ser
545                 550                 555                 560
```

```
Val Leu Thr Val Leu His Gln Asp Trp Leu Asn Gly Lys Glu Tyr Lys
                565                 570                 575

Cys Lys Val Ser Asn Lys Ala Leu Pro Ala Ser Ile Glu Lys Thr Ile
            580                 585                 590

Ser Lys Ala Lys Gly Gln Pro Arg Glu Pro Gln Val Tyr Thr Leu Pro
        595                 600                 605

Pro Ser Arg Asp Glu Leu Thr Lys Asn Gln Val Ser Leu Thr Cys Leu
    610                 615                 620

Val Lys Gly Phe Tyr Pro Ser Asp Ile Ala Val Glu Trp Glu Ser Asn
625                 630                 635                 640

Gly Gln Pro Glu Asn Asn Tyr Lys Thr Thr Pro Pro Val Leu Asp Ser
                645                 650                 655

Asp Gly Ser Phe Phe Leu Tyr Ser Lys Leu Thr Val Asp Lys Ser Arg
            660                 665                 670

Trp Gln Gln Gly Asn Val Phe Ser Cys Ser Val Met His Glu Ala Leu
        675                 680                 685

His Asn His Tyr Thr Gln Lys Ser Leu Ser Leu Ser Pro
    690                 695                 700


<210> SEQ ID NO 35
<211> LENGTH: 706
<212> TYPE: PRT
<213> ORGANISM: Artificial Sequence
<220> FEATURE:
<223> OTHER INFORMATION: Synthetic: scTNFR2 agonist with C-terminal IgG1
      with mutations. This is soluble TNF-a sequence, which includes
      VRSSSRTPSDK at N-terminus prior to THD domain and GGGGS prior to
      IgG1.

<400> SEQUENCE: 35

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu Val Arg Ser
145                 150                 155                 160

Ser Ser Arg Thr Pro Ser Asp Lys Pro Val Ala His Val Val Ala Asn
                165                 170                 175

Pro Gln Ala Glu Gly Gln Leu Gln Trp Leu Asn Arg Arg Ala Asn Ala
            180                 185                 190

Leu Leu Ala Asn Gly Val Glu Leu Arg Asp Asn Gln Leu Val Val Pro
        195                 200                 205
```

```
Ser Glu Gly Leu Tyr Leu Ile Tyr Ser Gln Val Leu Phe Lys Gly Gln
    210                 215                 220

Gly Cys Pro Ser Thr His Val Leu Leu Thr His Thr Ile Ser Arg Ile
225                 230                 235                 240

Ala Val Ser Tyr Gln Thr Lys Val Asn Leu Leu Ser Ala Ile Lys Ser
                245                 250                 255

Pro Cys Gln Arg Glu Thr Pro Glu Gly Ala Glu Ala Lys Pro Trp Tyr
            260                 265                 270

Glu Pro Ile Tyr Leu Gly Gly Val Phe Gln Leu Glu Lys Gly Asp Arg
        275                 280                 285

Leu Ser Ala Glu Ile Asn Arg Pro Asp Tyr Leu Asn Phe Arg Glu Ser
    290                 295                 300

Gly Gln Val Tyr Phe Gly Ile Ile Ala Leu Val Arg Ser Ser Ser Arg
305                 310                 315                 320

Thr Pro Ser Asp Lys Pro Val Ala His Val Val Ala Asn Pro Gln Ala
                325                 330                 335

Glu Gly Gln Leu Gln Trp Leu Asn Arg Arg Ala Asn Ala Leu Leu Ala
            340                 345                 350

Asn Gly Val Glu Leu Arg Asp Asn Gln Leu Val Val Pro Ser Glu Gly
        355                 360                 365

Leu Tyr Leu Ile Tyr Ser Gln Val Leu Phe Lys Gly Gln Gly Cys Pro
    370                 375                 380

Ser Thr His Val Leu Leu Thr His Thr Ile Ser Arg Ile Ala Val Ser
385                 390                 395                 400

Tyr Gln Thr Lys Val Asn Leu Leu Ser Ala Ile Lys Ser Pro Cys Gln
                405                 410                 415

Arg Glu Thr Pro Glu Gly Ala Glu Ala Lys Pro Trp Tyr Glu Pro Ile
            420                 425                 430

Tyr Leu Gly Gly Val Phe Gln Leu Glu Lys Gly Asp Arg Leu Ser Ala
        435                 440                 445

Glu Ile Asn Arg Pro Asp Tyr Leu Asn Phe Arg Glu Ser Gly Gln Val
    450                 455                 460

Tyr Phe Gly Ile Ile Ala Leu Gly Gly Gly Gly Ser Glu Pro Lys Ser
465                 470                 475                 480

Ser Asp Lys Thr His Thr Cys Pro Pro Cys Pro Ala Pro Glu Ala Ala
                485                 490                 495

Gly Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Lys Phe Asn Trp Tyr Val Asp Gly Val Glu
    530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Ser
            580                 585                 590

Ile Glu Lys Thr Ile Ser Lys Ala Lys Gly Gln Pro Arg Glu Pro Gln
        595                 600                 605

Val Tyr Thr Leu Pro Pro Ser Arg Asp Glu Leu Thr Lys Asn Gln Val
    610                 615                 620
```

```
Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Met His Glu Ala Leu His Asn His Tyr Thr Gln Lys Ser Leu Ser Leu
    690                 695                 700

Ser Pro
705


<210> SEQ ID NO 36
<211> LENGTH: 2100
<212> TYPE: DNA
<213> ORGANISM: Artificial Sequence
<220> FEATURE:
<223> OTHER INFORMATION: Synthetic: nucleic acid encoding SEQ ID NO:31
      optimized for Mus musculus expression by www.jcat.de

<400> SEQUENCE: 36

gagcccaaga gcagcgacaa gacccacacc tgcccccct gccccgcccc cgaggccgcc     60

ggcggcccca gcgtgttcct gttcccccc aagcccaagg acaccctgat gatcagcagg    120

acccccgagg tgacctgcgt ggtggtggac gtgagccacg aggaccccga ggtgaagttc    180

aactggtacg tggacggcgt ggaggtgcac aacgccaaga ccaagcccag ggaggagcag    240

tacaacagca cctacagggt ggtgagcgtg ctgaccgtgc tgcaccagga ctggctgaac    300

ggcaaggagt acaagtgcaa ggtgagcaac aaggccctgc ccgccagcat cgagaagacc    360

atcagcaagg ccaagggcca gcccagggag ccccaggtgt acaccctgcc ccccagcagg    420

gacgagctga ccaagaacca ggtgagcctg acctgcctgg tgaagggctt ctaccccagc    480

gacatcgccg tggagtggga gagcaacggc cagcccgaga acaactacaa gaccaccccc    540

cccgtgctgg acagcgacgg cagcttcttc ctgtacagca agctgaccgt ggacaagagc    600

aggtggcagc agggcaacgt gttcagctgc agcgtgatgc acgaggccct gcacaaccac    660

tacacccaga agagcctgag cctgagcccc ggcggcggcg gcagcggcgg cggcggcagc    720

cccgtggccc acgtggtggc caacccccag gccgagggcc agctgcagtg gctgaacagg    780

agggccaacg ccctgctggc caacggcgtg gagctgaggg acaaccagct ggtggtgccc    840

agcgagggcc tgtacctgat ctacagccag gtgctgttca agggccaggg ctgccccagc    900

acccacgtgc tgctgaccca caccatcagc aggatcgccg tgagctacca gaccaaggtg    960

aacctgctga gcgccatcaa gagcccctgc cagagggaga cccccgaggg cgccgaggcc   1020

aagccctggt acgagcccat ctacctgggc ggcgtgttcc agctggagaa gggcgacagg   1080

ctgagcgccg agatcaacag gcccgactac ctgaacttca gggagagcgg ccaggtgtac   1140

ttcggcatca tcgccctggt gaggagcagc agcaggaccc ccagcgacaa gcccgtggcc   1200

cacgtggtgg ccaaccccca ggccgagggc cagctgcagt ggctgaacag gagggccaac   1260

gccctgctgg ccaacggcgt ggagctgagg gacaaccagc tggtggtgcc cagcgagggc   1320

ctgtacctga tctacagcca ggtgctgttc aagggccagg gctgccccag cacccacgtg   1380

ctgctgaccc acaccatcag caggatcgcc gtgagctacc agaccaaggt gaacctgctg   1440

agcgccatca agagcccctg ccagagggag acccccgagg gcgccgaggc caagccctgg   1500
```

```
tacgagccca tctacctggg cggcgtgttc cagctggaga agggcgacag gctgagcgcc   1560

gagatcaaca ggcccgacta cctgaacttc agggagagcg gccaggtgta cttcggcatc   1620

atcgccctgg tgaggagcag cagcaggacc cccagcgaca agcccgtggc ccacgtggtg   1680

gccaaccccc aggccgaggg ccagctgcag tggctgaaca ggagggccaa cgccctgctg   1740

gccaacggcg tggagctgag ggacaaccag ctggtggtgc ccagcgaggg cctgtacctg   1800

atctacagcc aggtgctgtt caagggccag ggctgcccca gcacccacgt gctgctgacc   1860

cacaccatca gcaggatcgc cgtgagctac cagaccaagg tgaacctgct gagcgccatc   1920

aagagcccct gccagaggga gacccccgag ggcgccgagg ccaagccctg gtacgagccc   1980

atctacctgg gcggcgtgtt ccagctggag aagggcgaca ggctgagcgc cgagatcaac   2040

aggcccgact acctgaactt cagggagagc ggccaggtgt acttcggcat catcgccctg   2100
```

<210> SEQ ID NO 37
<211> LENGTH: 2130
<212> TYPE: DNA
<213> ORGANISM: Artificial Sequence
<220> FEATURE:
<223> OTHER INFORMATION: Synthetic: nucleic acid encoding SEQ ID NO:32 optimized for Mus musculus expression by www.jcat.de

<400> SEQUENCE: 37

```
gagcccaaga gcagcgacaa gacccacacc tgcccccct gccccgcccc cgaggccgcc     60

ggcggcccca gcgtgttcct gttcccccc aagcccaagg acaccctgat gatcagcagg    120

acccccgagg tgacctgcgt ggtggtggac gtgagccacg aggaccccga ggtgaagttc    180

aactggtacg tggacggcgt ggaggtgcac aacgccaaga ccaagcccag ggaggagcag    240

tacaacagca cctacagggt ggtgagcgtg ctgaccgtgc tgcaccagga ctggctgaac    300

ggcaaggagt acaagtgcaa ggtgagcaac aaggccctgc ccgccagcat cgagaagacc    360

atcagcaagg ccaagggcca gcccagggag ccccaggtgt acaccctgcc ccccagcagg    420

gacgagctga ccaagaacca ggtgagcctg acctgcctgg tgaagggctt ctaccccagc    480

gacatcgccg tggagtggga gagcaacggc cagcccgaga acaactacaa gaccaccccc    540

cccgtgctgg acagcgacgg cagcttcttc ctgtacagca agctgaccgt ggacaagagc    600

aggtggcagc agggcaacgt gttcagctgc agcgtgatgc acgaggccct gcacaaccac    660

tacacccaga agagcctgag cctgagcccc ggcggcggcg gcagcgtgag gagcagcagc    720

aggaccccca gcgacaagcc cgtggcccac gtggtggcca acccccaggc cgagggccag    780

ctgcagtggc tgaacaggag ggccaacgcc ctgctggcca acggcgtgga gctgagggac    840

aaccagctgg tggtgcccag cgagggcctg tacctgatct acagccaggt gctgttcaag    900

ggccagggct gccccagcac ccacgtgctg ctgacccaca ccatcagcag gatcgccgtg    960

agctaccaga ccaaggtgaa cctgctgagc gccatcaaga gcccctgcca gagggagacc   1020

cccgagggcg ccgaggccaa gccctggtac gagcccatct acctgggcgg cgtgttccag   1080

ctggagaagg gcgacaggct gagcgccgag atcaacaggc ccgactacct gaacttcagg   1140

gagagcggcc aggtgtactt cggcatcatc gccctgggcg gcggcggcag cagcagcagg   1200

acccccagcg acaagcccgt ggcccacgtg gtggccaacc cccaggccga gggccagctg   1260

cagtggctga acaggagggc caacgccctg ctggccaacg gcgtggagct gagggacaac   1320

cagctggtgg tgcccagcga gggcctgtac ctgatctaca gccaggtgct gttcaagggc   1380

cagggctgcc ccagcaccca cgtgctgctg acccacacca tcagcaggat cgccgtgagc   1440
```

```
taccagacca aggtgaacct gctgagcgcc atcaagagcc cctgccagag ggagaccccc   1500
gagggcgccg aggccaagcc ctggtacgag cccatctacc tgggcggcgt gttccagctg   1560
gagaagggcg acaggctgag cgccgagatc aacaggcccg actacctgaa cttcagggag   1620
agcggccagg tgtacttcgg catcatcgcc ctgggcggcg gcggcagcag cagcaggacc   1680
cccagcgaca agcccgtggc ccacgtggtg gccaaccccc aggccgaggg ccagctgcag   1740
tggctgaaca ggagggccaa cgccctgctg gccaacggcg tggagctgag ggacaaccag   1800
ctggtggtgc ccagcgaggg cctgtacctg atctacagcc aggtgctgtt caagggccag   1860
ggctgcccca gcacccacgt gctgctgacc cacaccatca gcaggatcgc cgtgagctac   1920
cagaccaagg tgaacctgct gagcgccatc aagagcccct gccagaggga gacccccgag   1980
ggcgccgagg ccaagccctg gtacgagccc atctacctgg gcggcgtgtt ccagctggag   2040
aagggcgaca ggctgagcgc cgagatcaac aggcccgact acctgaactt cagggagagc   2100
ggccaggtgt acttcggcat catcgccctg                                    2130
```

```
<210> SEQ ID NO 38
<211> LENGTH: 2103
<212> TYPE: DNA
<213> ORGANISM: Artificial Sequence
<220> FEATURE:
<223> OTHER INFORMATION: Synthetic: nucleic acid encoding SEQ ID NO:34
      optimized for Mus musculus expression by www.jcat.de

<400> SEQUENCE: 38
```

```
gtgaggagca gcagcaggac ccccagcgac aagcccgtgg cccacgtggt ggccaacccc     60
caggccgagg gccagctgca gtggctgaac aggagggcca acgccctgct ggccaacggc    120
gtggagctga gggacaacca gctggtggtg cccagcgagg gcctgtacct gatctacagc    180
caggtgctgt tcaagggcca gggctgcccc agcacccacg tgctgctgac ccacaccatc    240
agcaggatcg ccgtgagcta ccagaccaag gtgaacctgc tgagcgccat caagagcccc    300
tgccagaggg agacccccga gggcgccgag gccaagccct ggtacgagcc catctacctg    360
ggcggcgtgt tccagctgga gaagggcgac aggctgagcg ccgagatcaa caggcccgac    420
tacctgaact tcagggagag cggccaggtg tacttcggca tcatcgccct ggtgaggagc    480
agcagcagga cccccagcga caagcccgtg gcccacgtgg tggccaaccc ccaggccgag    540
ggccagctgc agtggctgaa caggagggcc aacgccctgc tggccaacgg cgtggagctg    600
agggacaacc agctggtggt gcccagcgag ggcctgtacc tgatctacag ccaggtgctg    660
ttcaagggcc agggctgccc cagcacccac gtgctgctga cccacaccat cagcaggatc    720
gccgtgagct accagaccaa ggtgaacctg ctgagcgcca tcaagagccc ctgccagagg    780
gagacccccg agggcgccga ggccaagccc tggtacgagc ccatctacct gggcggcgtg    840
ttccagctgg agaagggcga caggctgagc gccgagatca acaggcccga ctacctgaac    900
ttcagggaga gcggccaggt gtacttcggc atcatcgccc tggtgaggag cagcagcagg    960
acccccagcg acaagcccgt ggcccacgtg gtggccaacc cccaggccga gggccagctg   1020
cagtggctga acaggagggc caacgccctg ctggccaacg gcgtggagct gagggacaac   1080
cagctggtgg tgcccagcga gggcctgtac ctgatctaca gccaggtgct gttcaagggc   1140
cagggctgcc ccagcaccca cgtgctgctg acccacacca tcagcaggat cgccgtgagc   1200
taccagacca aggtgaacct gctgagcgcc atcaagagcc cctgccagag ggagaccccc   1260
gagggcgccg aggccaagcc ctggtacgag cccatctacc tgggcggcgt gttccagctg   1320
```

```
gagaagggcg acaggctgag cgccgagatc aacaggcccg actacctgaa cttcagggag   1380

agcggccagg tgtacttcgg catcatcgcc ctggagccca agagcagcga caagacccac   1440

acctgccccc cctgccccgc ccccgaggcc gccggcggcc ccagcgtgtt cctgttcccc   1500

cccaagccca aggacaccct gatgatcagc aggacccccg aggtgacctg cgtggtggtg   1560

gacgtgagcc acgaggaccc cgaggtgaag ttcaactggt acgtggacgg cgtggaggtg   1620

cacaacgcca agaccaagcc cagggaggag cagtacaaca gcacctacag ggtggtgagc   1680

gtgctgaccg tgctgcacca ggactggctg aacggcaagg agtacaagtg caaggtgagc   1740

aacaaggccc tgcccgccag catcgagaag accatcagca aggccaaggg ccagcccagg   1800

gagccccagg tgtacaccct gcccccccagc agggacgagc tgaccaagaa ccaggtgagc   1860

ctgacctgcc tggtgaaggg cttctacccc agcgacatcg ccgtggagtg ggagagcaac   1920

ggccagcccg agaacaacta caagaccacc ccccccgtgc tggacagcga cggcagcttc   1980

ttcctgtaca gcaagctgac cgtggacaag agcaggtggc agcagggcaa cgtgttcagc   2040

tgcagcgtga tgcacgaggc cctgcacaac cactacaccc agaagagcct gagcctgagc   2100

ccc                                                                 2103
```

```
<210> SEQ ID NO 39
<211> LENGTH: 2118
<212> TYPE: DNA
<213> ORGANISM: Artificial Sequence
<220> FEATURE:
<223> OTHER INFORMATION: Synthetic: nucleic acid encoding SEQ ID NO:35
      optimized for Mus musculus expression by www.jcat.de

<400> SEQUENCE: 39

gtgaggagca gcagcaggac ccccagcgac aagcccgtgg cccacgtggt ggccaacccc     60

caggccgagg gccagctgca gtggctgaac aggagggcca acgccctgct ggccaacggc    120

gtggagctga gggacaacca gctggtggtg cccagcgagg gcctgtacct gatctacagc    180

caggtgctgt tcaagggcca gggctgcccc agcacccacg tgctgctgac ccacaccatc    240

agcaggatcg ccgtgagcta ccagaccaag gtgaacctgc tgagcgccat caagagcccc    300

tgccagaggg agacccccga gggcgccgag gccaagccct ggtacgagcc catctacctg    360

ggcggcgtgt tccagctgga gaagggcgac aggctgagcg ccgagatcaa caggcccgac    420

tacctgaact tcagggagag cggccaggtg tacttcggca tcatcgccct ggtgaggagc    480

agcagcagga cccccagcga caagcccgtg gcccacgtgg tggccaaccc ccaggccgag    540

ggccagctgc agtggctgaa caggagggcc aacgccctgc tggccaacgg cgtggagctg    600

agggacaacc agctggtggt gcccagcgag ggcctgtacc tgatctacag ccaggtgctg    660

ttcaagggcc agggctgccc cagcacccac gtgctgctga cccacaccat cagcaggatc    720

gccgtgagct accagaccaa ggtgaacctg ctgagcgcca tcaagagccc ctgccagagg    780

gagacccccg agggcgccga ggccaagccc tggtacgagc ccatctacct gggcggcgtg    840

ttccagctgg agaagggcga caggctgagc gccgagatca acaggcccga ctacctgaac    900

ttcagggaga gcggccaggt gtacttcggc atcatcgccc tggtgaggag cagcagcagg    960

acccccagcg acaagcccgt ggcccacgtg gtggccaacc cccaggccga gggccagctg   1020

cagtggctga acaggagggc caacgccctg ctggccaacg gcgtggagct gagggacaac   1080

cagctggtgg tgcccagcga gggcctgtac ctgatctaca gccaggtgct gttcaagggc   1140

cagggctgcc ccagcaccca cgtgctgctg acccacacca tcagcaggat cgccgtgagc   1200
```

```
taccagacca aggtgaacct gctgagcgcc atcaagagcc cctgccagag ggagaccccc   1260

gagggcgccg aggccaagcc ctggtacgag cccatctacc tgggcggcgt gttccagctg   1320

gagaagggcg acaggctgag cgccgagatc aacaggcccg actacctgaa cttcagggag   1380

agcggccagg tgtacttcgg catcatcgcc ctgggcggcg gcggcagcga gcccaagagc   1440

agcgacaaga cccacacctg ccccccctgc cccgccccg aggccgccgg cggccccagc    1500

gtgttcctgt tcccccccaa gcccaaggac accctgatga tcagcaggac ccccgaggtg   1560

acctgcgtgg tggtggacgt gagccacgag gaccccgagg tgaagttcaa ctggtacgtg   1620

gacggcgtgg aggtgcacaa cgccaagacc aagcccaggg aggagcagta caacagcacc   1680

tacagggtgg tgagcgtgct gaccgtgctg caccaggact ggctgaacgg caaggagtac   1740

aagtgcaagg tgagcaacaa ggccctgccc gccagcatcg agaagaccat cagcaaggcc   1800

aagggccagc ccagggagcc ccaggtgtac accctgcccc ccagcaggga cgagctgacc   1860

aagaaccagg tgagcctgac ctgcctggtg aagggcttct accccagcga catcgccgtg   1920

gagtgggaga gcaacggcca gcccgagaac aactacaaga ccaccccccc cgtgctggac   1980

agcgacggca gcttcttcct gtacagcaag ctgaccgtgg acaagagcag gtggcagcag   2040

ggcaacgtgt tcagctgcag cgtgatgcac gaggccctgc acaaccacta cacccagaag   2100

agcctgagcc tgagcccc                                                2118
```

<210> SEQ ID NO 40
<211> LENGTH: 248
<212> TYPE: PRT
<213> ORGANISM: Homo sapiens
<220> FEATURE:
<221> NAME/KEY: misc_feature
<222> LOCATION: (1)..(248)
<223> OTHER INFORMATION: Human IgG1 sequence including C-terminal extension

<400> SEQUENCE: 40

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
```

```
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Glu Leu Gln Leu Glu Glu Ser Ser Ala Glu
225                 230                 235                 240

Ala Gln Asp Gly Glu Leu Asp Gly
                245


<210> SEQ ID NO 41
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Linker from C-terminus of Human IgG

<400> SEQUENCE: 41

Glu Leu Gln Leu Glu Glu Ser Ser Ala Glu Ala Gln Asp Gly Glu Leu
1               5                   10                  15

Asp Gly


<210> SEQ ID NO 42
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Linker variant derived from C-terminus of Human
      IgG

<400> SEQUENCE: 42

Glu Leu Gln Leu Glu Glu Ser Ser Ala Glu Ala Gln Gly Gly
1               5                   10


<210> SEQ ID NO 43
<211> LENGTH: 22
<212> TYPE: PRT
<213> ORGANISM: Homo sapiens
<220> FEATURE:
<221> NAME/KEY: misc_feature
<222> LOCATION: (1)..(22)
<223> OTHER INFORMATION: peptide

<400> SEQUENCE: 43

Gly Gly Gly Ser Gly Gly Gly Thr Gly Ser Glu Phe Leu Ala Ser Ser
1               5                   10                  15

Arg Thr Pro Ser Asp Lys
            20


<210> SEQ ID NO 44
<211> LENGTH: 25
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(5)
<223> OTHER INFORMATION: Gly Gly Gly Gly Ser is present at least one
      time and may repeat up to five times

<400> SEQUENCE: 44
```

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 45
<211> LENGTH: 50
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(50)
<223> OTHER INFORMATION: Gly Gly Gly Gly Ser is present at least one
      time and may repeat up to ten times

<400> SEQUENCE: 45

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50


<210> SEQ ID NO 46

<400> SEQUENCE: 46

000


<210> SEQ ID NO 47

<400> SEQUENCE: 47

000


<210> SEQ ID NO 48

<400> SEQUENCE: 48

000


<210> SEQ ID NO 49

<400> SEQUENCE: 49

000


<210> SEQ ID NO 50

<400> SEQUENCE: 50

000


<210> SEQ ID NO 51

<400> SEQUENCE: 51

000


<210> SEQ ID NO 52
```

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 592
<212> TYPE: PRT
<213> ORGANISM: Artificial Sequence
<220> FEATURE:
<223> OTHER INFORMATION: Synthetic: fusion protein

<400> SEQUENCE: 100

```
Asp Phe Thr Pro Pro Thr Val Lys Ile Leu Gln Ser Ser Cys Asp Gly
1               5                   10                  15

Gly Gly His Phe Pro Pro Thr Ile Gln Leu Leu Cys Leu Val Ser Gly
            20                  25                  30

Tyr Thr Pro Gly Thr Ile Asn Ile Thr Trp Leu Glu Asp Gly Gln Val
        35                  40                  45

Met Asp Val Asp Leu Ser Thr Ala Ser Thr Thr Gln Glu Gly Glu Leu
    50                  55                  60

Ala Ser Thr Gln Ser Glu Leu Thr Leu Ser Gln Lys His Trp Leu Ser
65                  70                  75                  80

Asp Arg Thr Tyr Thr Cys Gln Val Thr Tyr Gln Gly His Thr Phe Glu
                85                  90                  95

Asp Ser Thr Lys Lys Cys Ala Asp Ser Asn Gly Gly Gly Ser Gly Gly
            100                 105                 110

Gly Thr Gly Ser Glu Phe Leu Ala Ser Ser Arg Thr Pro Ser Asp Lys
        115                 120                 125

Pro Val Ala His Val Val Ala Asn Pro Gln Ala Glu Gly Gln Leu Gln
    130                 135                 140

Trp Leu Asn Arg Arg Ala Asn Ala Leu Leu Ala Asn Gly Val Glu Leu
145                 150                 155                 160

Arg Asp Asn Gln Leu Val Val Pro Ser Glu Gly Leu Tyr Leu Ile Tyr
                165                 170                 175

Ser Gln Val Leu Phe Lys Gly Gln Gly Cys Pro Ser Thr His Val Leu
            180                 185                 190

Leu Thr His Thr Ile Ser Arg Ile Ala Val Ser Tyr Gln Thr Lys Val
        195                 200                 205

Asn Leu Leu Ser Ala Ile Lys Ser Pro Cys Gln Arg Glu Thr Pro Glu
    210                 215                 220

Gly Ala Glu Ala Lys Pro Trp Tyr Glu Pro Ile Tyr Leu Gly Gly Val
225                 230                 235                 240

Phe Gln Leu Glu Lys Gly Asp Arg Leu Ser Ala Glu Ile Asn Arg Pro
                245                 250                 255

Asp Tyr Leu Asn Phe Arg Glu Ser Gly Gln Val Tyr Phe Gly Ile Ile
            260                 265                 270

Ala Leu Gly Gly Gly Gly Ser Ser Ser Arg Thr Pro Ser Asp Lys Pro
```

```
        275                 280                 285

Val Ala His Val Val Ala Asn Pro Gln Ala Glu Gly Gln Leu Gln Trp
    290                 295                 300

Leu Asn Arg Arg Ala Asn Ala Leu Leu Ala Asn Gly Val Glu Leu Arg
305                 310                 315                 320

Asp Asn Gln Leu Val Val Pro Ser Glu Gly Leu Tyr Leu Ile Tyr Ser
                325                 330                 335

Gln Val Leu Phe Lys Gly Gln Gly Cys Pro Ser Thr His Val Leu Leu
            340                 345                 350

Thr His Thr Ile Ser Arg Ile Ala Val Ser Tyr Gln Thr Lys Val Asn
        355                 360                 365

Leu Leu Ser Ala Ile Lys Ser Pro Cys Gln Arg Glu Thr Pro Glu Gly
    370                 375                 380

Ala Glu Ala Lys Pro Trp Tyr Glu Pro Ile Tyr Leu Gly Gly Val Phe
385                 390                 395                 400

Gln Leu Glu Lys Gly Asp Arg Leu Ser Ala Glu Ile Asn Arg Pro Asp
                405                 410                 415

Tyr Leu Asn Phe Arg Glu Ser Gly Gln Val Tyr Phe Gly Ile Ile Ala
            420                 425                 430

Leu Gly Gly Gly Gly Ser Ser Ser Arg Thr Pro Ser Asp Lys Pro Val
        435                 440                 445

Ala His Val Val Ala Asn Pro Gln Ala Glu Gly Gln Leu Gln Trp Leu
    450                 455                 460

Asn Arg Arg Ala Asn Ala Leu Leu Ala Asn Gly Val Glu Leu Arg Asp
465                 470                 475                 480

Asn Gln Leu Val Val Pro Ser Glu Gly Leu Tyr Leu Ile Tyr Ser Gln
                485                 490                 495

Val Leu Phe Lys Gly Gln Gly Cys Pro Ser Thr His Val Leu Leu Thr
            500                 505                 510

His Thr Ile Ser Arg Ile Ala Val Ser Tyr Gln Thr Lys Val Asn Leu
        515                 520                 525

Leu Ser Ala Ile Lys Ser Pro Cys Gln Arg Glu Thr Pro Glu Gly Ala
    530                 535                 540

Glu Ala Lys Pro Trp Tyr Glu Pro Ile Tyr Leu Gly Gly Val Phe Gln
545                 550                 555                 560

Leu Glu Lys Gly Asp Arg Leu Ser Ala Glu Ile Asn Arg Pro Asp Tyr
                565                 570                 575

Leu Asn Phe Arg Glu Ser Gly Gln Val Tyr Phe Gly Ile Ile Ala Leu
            580                 585                 590
```

<210> SEQ ID NO 101
<211> LENGTH: 709
<212> TYPE: PRT
<213> ORGANISM: Artificial Sequence
<220> FEATURE:
<223> OTHER INFORMATION: Synthetic: fusion protein

<400> SEQUENCE: 101

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
```

```
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Gly Ser Val Arg Ser Ser Ser Arg
225                 230                 235                 240

Thr Pro Ser Asp Lys Pro Val Ala His Val Val Ala Asn Pro Gln Ala
                245                 250                 255

Glu Gly Gln Leu Gln Trp Leu Asn Arg Arg Ala Asn Ala Leu Leu Ala
            260                 265                 270

Asn Gly Val Glu Leu Arg Asp Asn Gln Leu Val Val Pro Ser Glu Gly
        275                 280                 285

Leu Tyr Leu Ile Tyr Ser Gln Val Leu Phe Lys Gly Gln Gly Cys Pro
    290                 295                 300

Ser Thr His Val Leu Leu Thr His Thr Ile Ser Arg Ile Ala Val Ser
305                 310                 315                 320

Tyr Gln Thr Lys Val Asn Leu Leu Ser Ala Ile Lys Ser Pro Cys Gln
                325                 330                 335

Arg Glu Thr Pro Glu Gly Ala Glu Ala Lys Pro Trp Tyr Glu Pro Ile
            340                 345                 350

Tyr Leu Gly Gly Val Phe Gln Leu Glu Lys Gly Asp Arg Leu Ser Ala
        355                 360                 365

Glu Ile Asn Arg Pro Asp Tyr Leu Asn Phe Arg Glu Ser Gly Gln Val
    370                 375                 380

Tyr Phe Gly Ile Ile Ala Leu Gly Gly Gly Gly Ser Ser Ser Arg Thr
385                 390                 395                 400

Pro Ser Asp Lys Pro Val Ala His Val Val Ala Asn Pro Gln Ala Glu
                405                 410                 415

Gly Gln Leu Gln Trp Leu Asn Arg Arg Ala Asn Ala Leu Leu Ala Asn
            420                 425                 430

Gly Val Glu Leu Arg Asp Asn Gln Leu Val Val Pro Ser Glu Gly Leu
        435                 440                 445

Tyr Leu Ile Tyr Ser Gln Val Leu Phe Lys Gly Gln Gly Cys Pro Ser
    450                 455                 460

Thr His Val Leu Leu Thr His Thr Ile Ser Arg Ile Ala Val Ser Tyr
465                 470                 475                 480
```

```
Gln Thr Lys Val Asn Leu Leu Ser Ala Ile Lys Ser Pro Cys Gln Arg
                485                 490                 495

Glu Thr Pro Glu Gly Ala Glu Ala Lys Pro Trp Tyr Glu Pro Ile Tyr
            500                 505                 510

Leu Gly Gly Val Phe Gln Leu Glu Lys Gly Asp Arg Leu Ser Ala Glu
        515                 520                 525

Ile Asn Arg Pro Asp Tyr Leu Asn Phe Arg Glu Ser Gly Gln Val Tyr
    530                 535                 540

Phe Gly Ile Ile Ala Leu Gly Gly Gly Gly Ser Ser Ser Arg Thr Pro
545                 550                 555                 560

Ser Asp Lys Pro Val Ala His Val Val Ala Asn Pro Gln Ala Glu Gly
                565                 570                 575

Gln Leu Gln Trp Leu Asn Arg Arg Ala Asn Ala Leu Leu Ala Asn Gly
            580                 585                 590

Val Glu Leu Arg Asp Asn Gln Leu Val Val Pro Ser Glu Gly Leu Tyr
        595                 600                 605

Leu Ile Tyr Ser Gln Val Leu Phe Lys Gly Gln Gly Cys Pro Ser Thr
    610                 615                 620

His Val Leu Leu Thr His Thr Ile Ser Arg Ile Ala Val Ser Tyr Gln
625                 630                 635                 640

Thr Lys Val Asn Leu Leu Ser Ala Ile Lys Ser Pro Cys Gln Arg Glu
                645                 650                 655

Thr Pro Glu Gly Ala Glu Ala Lys Pro Trp Tyr Glu Pro Ile Tyr Leu
            660                 665                 670

Gly Gly Val Phe Gln Leu Glu Lys Gly Asp Arg Leu Ser Ala Glu Ile
        675                 680                 685

Asn Arg Pro Asp Tyr Leu Asn Phe Arg Glu Ser Gly Gln Val Tyr Phe
    690                 695                 700

Gly Ile Ile Ala Leu
705
```

<210> SEQ ID NO 102
<211> LENGTH: 699
<212> TYPE: PRT
<213> ORGANISM: Artificial Sequence
<220> FEATURE:
<223> OTHER INFORMATION: Synthetic: fusion protein

<400> SEQUENCE: 102

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125
```

```
Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Gly Ser Val Arg Ser Ser Ser Arg
225                 230                 235                 240

Thr Pro Ser Asp Lys Pro Val Ala His Val Val Ala Asn Pro Gln Ala
                245                 250                 255

Glu Gly Gln Leu Gln Trp Leu Asn Arg Arg Ala Asn Ala Leu Leu Ala
            260                 265                 270

Asn Gly Val Glu Leu Arg Asp Asn Gln Leu Val Val Pro Ser Glu Gly
        275                 280                 285

Leu Tyr Leu Ile Tyr Ser Gln Val Leu Phe Lys Gly Gln Gly Cys Pro
    290                 295                 300

Ser Thr His Val Leu Leu Thr His Thr Ile Ser Arg Ile Ala Val Ser
305                 310                 315                 320

Tyr Gln Thr Lys Val Asn Leu Leu Ser Ala Ile Lys Ser Pro Cys Gln
                325                 330                 335

Arg Glu Thr Pro Glu Gly Ala Glu Ala Lys Pro Trp Tyr Glu Pro Ile
            340                 345                 350

Tyr Leu Gly Gly Val Phe Gln Leu Glu Lys Gly Asp Arg Leu Ser Ala
        355                 360                 365

Glu Ile Asn Arg Pro Asp Tyr Leu Asn Phe Arg Glu Ser Gly Gln Val
    370                 375                 380

Tyr Phe Gly Ile Ile Ala Leu Ser Ser Arg Thr Pro Ser Asp Lys Pro
385                 390                 395                 400

Val Ala His Val Val Ala Asn Pro Gln Ala Glu Gly Gln Leu Gln Trp
                405                 410                 415

Leu Asn Arg Arg Ala Asn Ala Leu Leu Ala Asn Gly Val Glu Leu Arg
            420                 425                 430

Asp Asn Gln Leu Val Val Pro Ser Glu Gly Leu Tyr Leu Ile Tyr Ser
        435                 440                 445

Gln Val Leu Phe Lys Gly Gln Gly Cys Pro Ser Thr His Val Leu Leu
    450                 455                 460

Thr His Thr Ile Ser Arg Ile Ala Val Ser Tyr Gln Thr Lys Val Asn
465                 470                 475                 480

Leu Leu Ser Ala Ile Lys Ser Pro Cys Gln Arg Glu Thr Pro Glu Gly
                485                 490                 495

Ala Glu Ala Lys Pro Trp Tyr Glu Pro Ile Tyr Leu Gly Gly Val Phe
            500                 505                 510

Gln Leu Glu Lys Gly Asp Arg Leu Ser Ala Glu Ile Asn Arg Pro Asp
        515                 520                 525

Tyr Leu Asn Phe Arg Glu Ser Gly Gln Val Tyr Phe Gly Ile Ile Ala
    530                 535                 540
```

```
Leu Ser Ser Arg Thr Pro Ser Asp Lys Pro Val Ala His Val Val Ala
545                 550                 555                 560

Asn Pro Gln Ala Glu Gly Gln Leu Gln Trp Leu Asn Arg Arg Ala Asn
                565                 570                 575

Ala Leu Leu Ala Asn Gly Val Glu Leu Arg Asp Asn Gln Leu Val Val
            580                 585                 590

Pro Ser Glu Gly Leu Tyr Leu Ile Tyr Ser Gln Val Leu Phe Lys Gly
        595                 600                 605

Gln Gly Cys Pro Ser Thr His Val Leu Leu Thr His Thr Ile Ser Arg
    610                 615                 620

Ile Ala Val Ser Tyr Gln Thr Lys Val Asn Leu Leu Ser Ala Ile Lys
625                 630                 635                 640

Ser Pro Cys Gln Arg Glu Thr Pro Glu Gly Ala Glu Ala Lys Pro Trp
                645                 650                 655

Tyr Glu Pro Ile Tyr Leu Gly Gly Val Phe Gln Leu Glu Lys Gly Asp
            660                 665                 670

Arg Leu Ser Ala Glu Ile Asn Arg Pro Asp Tyr Leu Asn Phe Arg Glu
        675                 680                 685

Ser Gly Gln Val Tyr Phe Gly Ile Ile Ala Leu
    690                 695
```

<210> SEQ ID NO 103
<211> LENGTH: 705
<212> TYPE: PRT
<213> ORGANISM: Artificial Sequence
<220> FEATURE:
<223> OTHER INFORMATION: Synthetic: fusion protein

<400> SEQUENCE: 103

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205
```

```
Val Met His Glu Ala Leu His Asn His Tyr Thr Gln Lys Ser Leu Ser
    210                 215                 220

Leu Ser Leu Gly Lys Gly Gly Gly Gly Ser Val Arg Ser Ser Ser Arg
225                 230                 235                 240

Thr Pro Ser Asp Lys Pro Val Ala His Val Val Ala Asn Pro Gln Ala
                245                 250                 255

Glu Gly Gln Leu Gln Trp Leu Asn Arg Arg Ala Asn Ala Leu Leu Ala
            260                 265                 270

Asn Gly Val Glu Leu Arg Asp Asn Gln Leu Val Val Pro Ser Glu Gly
        275                 280                 285

Leu Tyr Leu Ile Tyr Ser Gln Val Leu Phe Lys Gly Gln Gly Cys Pro
    290                 295                 300

Ser Thr His Val Leu Leu Thr His Thr Ile Ser Arg Ile Ala Val Ser
305                 310                 315                 320

Tyr Gln Thr Lys Val Asn Leu Leu Ser Ala Ile Lys Ser Pro Cys Gln
                325                 330                 335

Arg Glu Thr Pro Glu Gly Ala Glu Ala Lys Pro Trp Tyr Glu Pro Ile
            340                 345                 350

Tyr Leu Gly Gly Val Phe Gln Leu Glu Lys Gly Asp Arg Leu Ser Ala
        355                 360                 365

Glu Ile Asn Arg Pro Asp Tyr Leu Asn Phe Arg Glu Ser Gly Gln Val
    370                 375                 380

Tyr Phe Gly Ile Ile Ala Leu Val Arg Ser Ser Ser Arg Thr Pro Ser
385                 390                 395                 400

Asp Lys Pro Val Ala His Val Val Ala Asn Pro Gln Ala Glu Gly Gln
                405                 410                 415

Leu Gln Trp Leu Asn Arg Arg Ala Asn Ala Leu Leu Ala Asn Gly Val
            420                 425                 430

Glu Leu Arg Asp Asn Gln Leu Val Val Pro Ser Glu Gly Leu Tyr Leu
        435                 440                 445

Ile Tyr Ser Gln Val Leu Phe Lys Gly Gln Gly Cys Pro Ser Thr His
    450                 455                 460

Val Leu Leu Thr His Thr Ile Ser Arg Ile Ala Val Ser Tyr Gln Thr
465                 470                 475                 480

Lys Val Asn Leu Leu Ser Ala Ile Lys Ser Pro Cys Gln Arg Glu Thr
                485                 490                 495

Pro Glu Gly Ala Glu Ala Lys Pro Trp Tyr Glu Pro Ile Tyr Leu Gly
            500                 505                 510

Gly Val Phe Gln Leu Glu Lys Gly Asp Arg Leu Ser Ala Glu Ile Asn
        515                 520                 525

Arg Pro Asp Tyr Leu Asn Phe Arg Glu Ser Gly Gln Val Tyr Phe Gly
    530                 535                 540

Ile Ile Ala Leu Val Arg Ser Ser Ser Arg Thr Pro Ser Asp Lys Pro
545                 550                 555                 560

Val Ala His Val Val Ala Asn Pro Gln Ala Glu Gly Gln Leu Gln Trp
                565                 570                 575

Leu Asn Arg Arg Ala Asn Ala Leu Leu Ala Asn Gly Val Glu Leu Arg
            580                 585                 590

Asp Asn Gln Leu Val Val Pro Ser Glu Gly Leu Tyr Leu Ile Tyr Ser
        595                 600                 605

Gln Val Leu Phe Lys Gly Gln Gly Cys Pro Ser Thr His Val Leu Leu
    610                 615                 620

Thr His Thr Ile Ser Arg Ile Ala Val Ser Tyr Gln Thr Lys Val Asn
```

625 630 635 640

Leu Leu Ser Ala Ile Lys Ser Pro Cys Gln Arg Glu Thr Pro Glu Gly
645 650 655

Ala Glu Ala Lys Pro Trp Tyr Glu Pro Ile Tyr Leu Gly Gly Val Phe
660 665 670

Gln Leu Glu Lys Gly Asp Arg Leu Ser Ala Glu Ile Asn Arg Pro Asp
675 680 685

Tyr Leu Asn Phe Arg Glu Ser Gly Gln Val Tyr Phe Gly Ile Ile Ala
690 695 700

Leu
705

<210> SEQ ID NO 104
<211> LENGTH: 714
<212> TYPE: PRT
<213> ORGANISM: Artificial Sequence
<220> FEATURE:
<223> OTHER INFORMATION: Synthetic: fusion protein

<400> SEQUENCE: 104

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys Gly Gly Gly Gly Ser Gly Gly Gly Gly Ser Val
225 230 235 240

Arg Ser Ser Ser Arg Thr Pro Ser Asp Lys Pro Val Ala His Val Val
245 250 255

Ala Asn Pro Gln Ala Glu Gly Gln Leu Gln Trp Leu Asn Arg Arg Ala
260 265 270

Asn Ala Leu Leu Ala Asn Gly Val Glu Leu Arg Asp Asn Gln Leu Val

```
        275                 280                 285

Val Pro Ser Glu Gly Leu Tyr Leu Ile Tyr Ser Gln Val Leu Phe Lys
    290                 295                 300

Gly Gln Gly Cys Pro Ser Thr His Val Leu Leu Thr His Thr Ile Ser
305                 310                 315                 320

Arg Ile Ala Val Ser Tyr Gln Thr Lys Val Asn Leu Leu Ser Ala Ile
                325                 330                 335

Lys Ser Pro Cys Gln Arg Glu Thr Pro Glu Gly Ala Glu Ala Lys Pro
            340                 345                 350

Trp Tyr Glu Pro Ile Tyr Leu Gly Gly Val Phe Gln Leu Glu Lys Gly
        355                 360                 365

Asp Arg Leu Ser Ala Glu Ile Asn Arg Pro Asp Tyr Leu Asn Phe Arg
    370                 375                 380

Glu Ser Gly Gln Val Tyr Phe Gly Ile Ile Ala Leu Gly Gly Gly Gly
385                 390                 395                 400

Ser Ser Ser Arg Thr Pro Ser Asp Lys Pro Val Ala His Val Val Ala
                405                 410                 415

Asn Pro Gln Ala Glu Gly Gln Leu Gln Trp Leu Asn Arg Arg Ala Asn
            420                 425                 430

Ala Leu Leu Ala Asn Gly Val Glu Leu Arg Asp Asn Gln Leu Val Val
        435                 440                 445

Pro Ser Glu Gly Leu Tyr Leu Ile Tyr Ser Gln Val Leu Phe Lys Gly
    450                 455                 460

Gln Gly Cys Pro Ser Thr His Val Leu Leu Thr His Thr Ile Ser Arg
465                 470                 475                 480

Ile Ala Val Ser Tyr Gln Thr Lys Val Asn Leu Leu Ser Ala Ile Lys
                485                 490                 495

Ser Pro Cys Gln Arg Glu Thr Pro Glu Gly Ala Glu Ala Lys Pro Trp
            500                 505                 510

Tyr Glu Pro Ile Tyr Leu Gly Gly Val Phe Gln Leu Glu Lys Gly Asp
        515                 520                 525

Arg Leu Ser Ala Glu Ile Asn Arg Pro Asp Tyr Leu Asn Phe Arg Glu
    530                 535                 540

Ser Gly Gln Val Tyr Phe Gly Ile Ile Ala Leu Gly Gly Gly Gly Ser
545                 550                 555                 560

Ser Ser Arg Thr Pro Ser Asp Lys Pro Val Ala His Val Val Ala Asn
                565                 570                 575

Pro Gln Ala Glu Gly Gln Leu Gln Trp Leu Asn Arg Arg Ala Asn Ala
            580                 585                 590

Leu Leu Ala Asn Gly Val Glu Leu Arg Asp Asn Gln Leu Val Val Pro
        595                 600                 605

Ser Glu Gly Leu Tyr Leu Ile Tyr Ser Gln Val Leu Phe Lys Gly Gln
    610                 615                 620

Gly Cys Pro Ser Thr His Val Leu Leu Thr His Thr Ile Ser Arg Ile
625                 630                 635                 640

Ala Val Ser Tyr Gln Thr Lys Val Asn Leu Leu Ser Ala Ile Lys Ser
                645                 650                 655

Pro Cys Gln Arg Glu Thr Pro Glu Gly Ala Glu Ala Lys Pro Trp Tyr
            660                 665                 670

Glu Pro Ile Tyr Leu Gly Gly Val Phe Gln Leu Glu Lys Gly Asp Arg
        675                 680                 685

Leu Ser Ala Glu Ile Asn Arg Pro Asp Tyr Leu Asn Phe Arg Glu Ser
    690                 695                 700
```

```
Gly Gln Val Tyr Phe Gly Ile Ile Ala Leu
705                 710


<210> SEQ ID NO 105
<211> LENGTH: 704
<212> TYPE: PRT
<213> ORGANISM: Artificial Sequence
<220> FEATURE:
<223> OTHER INFORMATION: Synthetic: fusion protein

<400> SEQUENCE: 105

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Gly Ser Gly Gly Gly Gly Ser Val
225                 230                 235                 240

Arg Ser Ser Ser Arg Thr Pro Ser Asp Lys Pro Val Ala His Val Val
                245                 250                 255

Ala Asn Pro Gln Ala Glu Gly Gln Leu Gln Trp Leu Asn Arg Arg Ala
            260                 265                 270

Asn Ala Leu Leu Ala Asn Gly Val Glu Leu Arg Asp Asn Gln Leu Val
        275                 280                 285

Val Pro Ser Glu Gly Leu Tyr Leu Ile Tyr Ser Gln Val Leu Phe Lys
    290                 295                 300

Gly Gln Gly Cys Pro Ser Thr His Val Leu Leu Thr His Thr Ile Ser
305                 310                 315                 320

Arg Ile Ala Val Ser Tyr Gln Thr Lys Val Asn Leu Leu Ser Ala Ile
                325                 330                 335

Lys Ser Pro Cys Gln Arg Glu Thr Pro Glu Gly Ala Glu Ala Lys Pro
            340                 345                 350
```

```
Trp Tyr Glu Pro Ile Tyr Leu Gly Gly Val Phe Gln Leu Glu Lys Gly
        355                 360                 365

Asp Arg Leu Ser Ala Glu Ile Asn Arg Pro Asp Tyr Leu Asn Phe Arg
    370                 375                 380

Glu Ser Gly Gln Val Tyr Phe Gly Ile Ile Ala Leu Ser Ser Arg Thr
385                 390                 395                 400

Pro Ser Asp Lys Pro Val Ala His Val Val Ala Asn Pro Gln Ala Glu
                405                 410                 415

Gly Gln Leu Gln Trp Leu Asn Arg Arg Ala Asn Ala Leu Leu Ala Asn
            420                 425                 430

Gly Val Glu Leu Arg Asp Asn Gln Leu Val Val Pro Ser Glu Gly Leu
        435                 440                 445

Tyr Leu Ile Tyr Ser Gln Val Leu Phe Lys Gly Gln Gly Cys Pro Ser
    450                 455                 460

Thr His Val Leu Leu Thr His Thr Ile Ser Arg Ile Ala Val Ser Tyr
465                 470                 475                 480

Gln Thr Lys Val Asn Leu Leu Ser Ala Ile Lys Ser Pro Cys Gln Arg
                485                 490                 495

Glu Thr Pro Glu Gly Ala Glu Ala Lys Pro Trp Tyr Glu Pro Ile Tyr
            500                 505                 510

Leu Gly Gly Val Phe Gln Leu Glu Lys Gly Asp Arg Leu Ser Ala Glu
        515                 520                 525

Ile Asn Arg Pro Asp Tyr Leu Asn Phe Arg Glu Ser Gly Gln Val Tyr
    530                 535                 540

Phe Gly Ile Ile Ala Leu Ser Ser Arg Thr Pro Ser Asp Lys Pro Val
545                 550                 555                 560

Ala His Val Val Ala Asn Pro Gln Ala Glu Gly Gln Leu Gln Trp Leu
                565                 570                 575

Asn Arg Arg Ala Asn Ala Leu Leu Ala Asn Gly Val Glu Leu Arg Asp
            580                 585                 590

Asn Gln Leu Val Val Pro Ser Glu Gly Leu Tyr Leu Ile Tyr Ser Gln
        595                 600                 605

Val Leu Phe Lys Gly Gln Gly Cys Pro Ser Thr His Val Leu Leu Thr
    610                 615                 620

His Thr Ile Ser Arg Ile Ala Val Ser Tyr Gln Thr Lys Val Asn Leu
625                 630                 635                 640

Leu Ser Ala Ile Lys Ser Pro Cys Gln Arg Glu Thr Pro Glu Gly Ala
                645                 650                 655

Glu Ala Lys Pro Trp Tyr Glu Pro Ile Tyr Leu Gly Gly Val Phe Gln
            660                 665                 670

Leu Glu Lys Gly Asp Arg Leu Ser Ala Glu Ile Asn Arg Pro Asp Tyr
        675                 680                 685

Leu Asn Phe Arg Glu Ser Gly Gln Val Tyr Phe Gly Ile Ile Ala Leu
    690                 695                 700
```

<210> SEQ ID NO 106
<211> LENGTH: 710
<212> TYPE: PRT
<213> ORGANISM: Artificial Sequence
<220> FEATURE:
<223> OTHER INFORMATION: Synthetic: fusion protein

<400> SEQUENCE: 106

```
Glu Ser Lys Tyr Gly Pro Pro Cys Pro Pro Cys Pro Ala Pro Glu Phe
1               5                   10                  15
```

-continued

```
Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Gly Ser Gly Gly Gly Gly Ser Val
225                 230                 235                 240

Arg Ser Ser Ser Arg Thr Pro Ser Asp Lys Pro Val Ala His Val Val
                245                 250                 255

Ala Asn Pro Gln Ala Glu Gly Gln Leu Gln Trp Leu Asn Arg Arg Ala
            260                 265                 270

Asn Ala Leu Leu Ala Asn Gly Val Glu Leu Arg Asp Asn Gln Leu Val
        275                 280                 285

Val Pro Ser Glu Gly Leu Tyr Leu Ile Tyr Ser Gln Val Leu Phe Lys
    290                 295                 300

Gly Gln Gly Cys Pro Ser Thr His Val Leu Leu Thr His Thr Ile Ser
305                 310                 315                 320

Arg Ile Ala Val Ser Tyr Gln Thr Lys Val Asn Leu Leu Ser Ala Ile
                325                 330                 335

Lys Ser Pro Cys Gln Arg Glu Thr Pro Glu Gly Ala Glu Ala Lys Pro
            340                 345                 350

Trp Tyr Glu Pro Ile Tyr Leu Gly Gly Val Phe Gln Leu Glu Lys Gly
        355                 360                 365

Asp Arg Leu Ser Ala Glu Ile Asn Arg Pro Asp Tyr Leu Asn Phe Arg
    370                 375                 380

Glu Ser Gly Gln Val Tyr Phe Gly Ile Ile Ala Leu Val Arg Ser Ser
385                 390                 395                 400

Ser Arg Thr Pro Ser Asp Lys Pro Val Ala His Val Val Ala Asn Pro
                405                 410                 415

Gln Ala Glu Gly Gln Leu Gln Trp Leu Asn Arg Arg Ala Asn Ala Leu
            420                 425                 430
```

```
Leu Ala Asn Gly Val Glu Leu Arg Asp Asn Gln Leu Val Val Pro Ser
        435                 440                 445

Glu Gly Leu Tyr Leu Ile Tyr Ser Gln Val Leu Phe Lys Gly Gln Gly
    450                 455                 460

Cys Pro Ser Thr His Val Leu Leu Thr His Thr Ile Ser Arg Ile Ala
465                 470                 475                 480

Val Ser Tyr Gln Thr Lys Val Asn Leu Leu Ser Ala Ile Lys Ser Pro
                485                 490                 495

Cys Gln Arg Glu Thr Pro Glu Gly Ala Glu Ala Lys Pro Trp Tyr Glu
            500                 505                 510

Pro Ile Tyr Leu Gly Gly Val Phe Gln Leu Glu Lys Gly Asp Arg Leu
        515                 520                 525

Ser Ala Glu Ile Asn Arg Pro Asp Tyr Leu Asn Phe Arg Glu Ser Gly
    530                 535                 540

Gln Val Tyr Phe Gly Ile Ile Ala Leu Val Arg Ser Ser Ser Arg Thr
545                 550                 555                 560

Pro Ser Asp Lys Pro Val Ala His Val Val Ala Asn Pro Gln Ala Glu
                565                 570                 575

Gly Gln Leu Gln Trp Leu Asn Arg Arg Ala Asn Ala Leu Leu Ala Asn
            580                 585                 590

Gly Val Glu Leu Arg Asp Asn Gln Leu Val Val Pro Ser Glu Gly Leu
        595                 600                 605

Tyr Leu Ile Tyr Ser Gln Val Leu Phe Lys Gly Gln Gly Cys Pro Ser
    610                 615                 620

Thr His Val Leu Leu Thr His Thr Ile Ser Arg Ile Ala Val Ser Tyr
625                 630                 635                 640

Gln Thr Lys Val Asn Leu Leu Ser Ala Ile Lys Ser Pro Cys Gln Arg
                645                 650                 655

Glu Thr Pro Glu Gly Ala Glu Ala Lys Pro Trp Tyr Glu Pro Ile Tyr
            660                 665                 670

Leu Gly Gly Val Phe Gln Leu Glu Lys Gly Asp Arg Leu Ser Ala Glu
        675                 680                 685

Ile Asn Arg Pro Asp Tyr Leu Asn Phe Arg Glu Ser Gly Gln Val Tyr
    690                 695                 700

Phe Gly Ile Ile Ala Leu
705                 710


<210> SEQ ID NO 107
<211> LENGTH: 709
<212> TYPE: PRT
<213> ORGANISM: Artificial Sequence
<220> FEATURE:
<223> OTHER INFORMATION: Synthetic: fusion protein

<400> SEQUENCE: 107

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80
```

```
Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu Gly Gly Gly
145                 150                 155                 160

Gly Ser Ser Ser Arg Thr Pro Ser Asp Lys Pro Val Ala His Val Val
                165                 170                 175

Ala Asn Pro Gln Ala Glu Gly Gln Leu Gln Trp Leu Asn Arg Arg Ala
            180                 185                 190

Asn Ala Leu Leu Ala Asn Gly Val Glu Leu Arg Asp Asn Gln Leu Val
        195                 200                 205

Val Pro Ser Glu Gly Leu Tyr Leu Ile Tyr Ser Gln Val Leu Phe Lys
    210                 215                 220

Gly Gln Gly Cys Pro Ser Thr His Val Leu Leu Thr His Thr Ile Ser
225                 230                 235                 240

Arg Ile Ala Val Ser Tyr Gln Thr Lys Val Asn Leu Leu Ser Ala Ile
                245                 250                 255

Lys Ser Pro Cys Gln Arg Glu Thr Pro Glu Gly Ala Glu Ala Lys Pro
            260                 265                 270

Trp Tyr Glu Pro Ile Tyr Leu Gly Gly Val Phe Gln Leu Glu Lys Gly
        275                 280                 285

Asp Arg Leu Ser Ala Glu Ile Asn Arg Pro Asp Tyr Leu Asn Phe Arg
    290                 295                 300

Glu Ser Gly Gln Val Tyr Phe Gly Ile Ile Ala Leu Gly Gly Gly Gly
305                 310                 315                 320

Ser Ser Ser Arg Thr Pro Ser Asp Lys Pro Val Ala His Val Val Ala
                325                 330                 335

Asn Pro Gln Ala Glu Gly Gln Leu Gln Trp Leu Asn Arg Arg Ala Asn
            340                 345                 350

Ala Leu Leu Ala Asn Gly Val Glu Leu Arg Asp Asn Gln Leu Val Val
        355                 360                 365

Pro Ser Glu Gly Leu Tyr Leu Ile Tyr Ser Gln Val Leu Phe Lys Gly
    370                 375                 380

Gln Gly Cys Pro Ser Thr His Val Leu Leu Thr His Thr Ile Ser Arg
385                 390                 395                 400

Ile Ala Val Ser Tyr Gln Thr Lys Val Asn Leu Leu Ser Ala Ile Lys
                405                 410                 415

Ser Pro Cys Gln Arg Glu Thr Pro Glu Gly Ala Glu Ala Lys Pro Trp
            420                 425                 430

Tyr Glu Pro Ile Tyr Leu Gly Gly Val Phe Gln Leu Glu Lys Gly Asp
        435                 440                 445

Arg Leu Ser Ala Glu Ile Asn Arg Pro Asp Tyr Leu Asn Phe Arg Glu
    450                 455                 460

Ser Gly Gln Val Tyr Phe Gly Ile Ile Ala Leu Gly Gly Gly Gly Ser
465                 470                 475                 480

Glu Ser Lys Tyr Gly Pro Pro Cys Pro Pro Cys Pro Ala Pro Glu Phe
                485                 490                 495

Leu Gly Gly Pro Ser Val Phe Leu Phe Pro Pro Lys Pro Lys Asp Thr
```

```
            500                 505                 510

Leu Met Ile Ser Arg Thr Pro Glu Val Thr Cys Val Val Val Asp Val
        515                 520                 525

Ser Gln Glu Asp Pro Glu Val Gln Phe Asn Trp Tyr Val Asp Gly Val
    530                 535                 540

Glu Val His Asn Ala Lys Thr Lys Pro Arg Glu Glu Gln Phe Asn Ser
545                 550                 555                 560

Thr Tyr Arg Val Val Ser Val Leu Thr Val Leu His Gln Asp Trp Leu
                565                 570                 575

Asn Gly Lys Glu Tyr Lys Cys Lys Val Ser Asn Lys Gly Leu Pro Ser
            580                 585                 590

Ser Ile Glu Lys Thr Ile Ser Lys Ala Lys Gly Gln Pro Arg Glu Pro
        595                 600                 605

Gln Val Tyr Thr Leu Pro Pro Ser Gln Glu Glu Met Thr Lys Asn Gln
    610                 615                 620

Val Ser Leu Thr Cys Leu Val Lys Gly Phe Tyr Pro Ser Asp Ile Ala
625                 630                 635                 640

Val Glu Trp Glu Ser Asn Gly Gln Pro Glu Asn Asn Tyr Lys Thr Thr
                645                 650                 655

Pro Pro Val Leu Asp Ser Asp Gly Ser Phe Phe Leu Tyr Ser Arg Leu
            660                 665                 670

Thr Val Asp Lys Ser Arg Trp Gln Glu Gly Asn Val Phe Ser Cys Ser
        675                 680                 685

Val Met His Glu Ala Leu His Asn His Tyr Thr Gln Lys Ser Leu Ser
    690                 695                 700

Leu Ser Leu Gly Lys
705


<210> SEQ ID NO 108
<211> LENGTH: 699
<212> TYPE: PRT
<213> ORGANISM: Artificial Sequence
<220> FEATURE:
<223> OTHER INFORMATION: Synthetic: fusion protein

<400> SEQUENCE: 108

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu Ser Ser Arg
```

```
145                 150                 155                 160

Thr Pro Ser Asp Lys Pro Val Ala His Val Val Ala Asn Pro Gln Ala
                165                 170                 175

Glu Gly Gln Leu Gln Trp Leu Asn Arg Arg Ala Asn Ala Leu Leu Ala
            180                 185                 190

Asn Gly Val Glu Leu Arg Asp Asn Gln Leu Val Val Pro Ser Glu Gly
        195                 200                 205

Leu Tyr Leu Ile Tyr Ser Gln Val Leu Phe Lys Gly Gln Gly Cys Pro
    210                 215                 220

Ser Thr His Val Leu Leu Thr His Thr Ile Ser Arg Ile Ala Val Ser
225                 230                 235                 240

Tyr Gln Thr Lys Val Asn Leu Leu Ser Ala Ile Lys Ser Pro Cys Gln
                245                 250                 255

Arg Glu Thr Pro Glu Gly Ala Glu Ala Lys Pro Trp Tyr Glu Pro Ile
            260                 265                 270

Tyr Leu Gly Gly Val Phe Gln Leu Glu Lys Gly Asp Arg Leu Ser Ala
        275                 280                 285

Glu Ile Asn Arg Pro Asp Tyr Leu Asn Phe Arg Glu Ser Gly Gln Val
    290                 295                 300

Tyr Phe Gly Ile Ile Ala Leu Ser Ser Arg Thr Pro Ser Asp Lys Pro
305                 310                 315                 320

Val Ala His Val Val Ala Asn Pro Gln Ala Glu Gly Gln Leu Gln Trp
                325                 330                 335

Leu Asn Arg Arg Ala Asn Ala Leu Leu Ala Asn Gly Val Glu Leu Arg
            340                 345                 350

Asp Asn Gln Leu Val Val Pro Ser Glu Gly Leu Tyr Leu Ile Tyr Ser
        355                 360                 365

Gln Val Leu Phe Lys Gly Gln Gly Cys Pro Ser Thr His Val Leu Leu
    370                 375                 380

Thr His Thr Ile Ser Arg Ile Ala Val Ser Tyr Gln Thr Lys Val Asn
385                 390                 395                 400

Leu Leu Ser Ala Ile Lys Ser Pro Cys Gln Arg Glu Thr Pro Glu Gly
                405                 410                 415

Ala Glu Ala Lys Pro Trp Tyr Glu Pro Ile Tyr Leu Gly Gly Val Phe
            420                 425                 430

Gln Leu Glu Lys Gly Asp Arg Leu Ser Ala Glu Ile Asn Arg Pro Asp
        435                 440                 445

Tyr Leu Asn Phe Arg Glu Ser Gly Gln Val Tyr Phe Gly Ile Ile Ala
    450                 455                 460

Leu Gly Gly Gly Gly Ser Glu Ser Lys Tyr Gly Pro Pro Cys Pro Pro
465                 470                 475                 480

Cys Pro Ala Pro Glu Phe Leu Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser Gln Glu Asp Pro Glu Val Gln Phe Asn
        515                 520                 525

Trp Tyr Val Asp Gly Val Glu Val His Asn Ala Lys Thr Lys Pro Arg
    530                 535                 540

Glu Glu Gln Phe Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575
```

```
Asn Lys Gly Leu Pro Ser Ser Ile Glu Lys Thr Ile Ser Lys Ala Lys
            580                 585                 590

Gly Gln Pro Arg Glu Pro Gln Val Tyr Thr Leu Pro Pro Ser Gln Glu
        595                 600                 605

Glu Met Thr Lys Asn Gln Val Ser Leu Thr Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Arg Leu Thr Val Asp Lys Ser Arg Trp Gln Glu Gly
            660                 665                 670

Asn Val Phe Ser Cys Ser Val Met His Glu Ala Leu His Asn His Tyr
        675                 680                 685

Thr Gln Lys Ser Leu Ser Leu Ser Leu Gly Lys
    690                 695
```

<210> SEQ ID NO 109
<211> LENGTH: 705
<212> TYPE: PRT
<213> ORGANISM: Artificial Sequence
<220> FEATURE:
<223> OTHER INFORMATION: Synthetic: fusion protein

<400> SEQUENCE: 109

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu Val Arg Ser
145                 150                 155                 160

Ser Ser Arg Thr Pro Ser Asp Lys Pro Val Ala His Val Val Ala Asn
                165                 170                 175

Pro Gln Ala Glu Gly Gln Leu Gln Trp Leu Asn Arg Arg Ala Asn Ala
            180                 185                 190

Leu Leu Ala Asn Gly Val Glu Leu Arg Asp Asn Gln Leu Val Val Pro
        195                 200                 205

Ser Glu Gly Leu Tyr Leu Ile Tyr Ser Gln Val Leu Phe Lys Gly Gln
    210                 215                 220

Gly Cys Pro Ser Thr His Val Leu Leu Thr His Thr Ile Ser Arg Ile
225                 230                 235                 240
```

```
Ala Val Ser Tyr Gln Thr Lys Val Asn Leu Leu Ser Ala Ile Lys Ser
                245                 250                 255

Pro Cys Gln Arg Glu Thr Pro Glu Gly Ala Glu Ala Lys Pro Trp Tyr
            260                 265                 270

Glu Pro Ile Tyr Leu Gly Gly Val Phe Gln Leu Glu Lys Gly Asp Arg
        275                 280                 285

Leu Ser Ala Glu Ile Asn Arg Pro Asp Tyr Leu Asn Phe Arg Glu Ser
    290                 295                 300

Gly Gln Val Tyr Phe Gly Ile Ile Ala Leu Val Arg Ser Ser Ser Arg
305                 310                 315                 320

Thr Pro Ser Asp Lys Pro Val Ala His Val Val Ala Asn Pro Gln Ala
                325                 330                 335

Glu Gly Gln Leu Gln Trp Leu Asn Arg Arg Ala Asn Ala Leu Leu Ala
            340                 345                 350

Asn Gly Val Glu Leu Arg Asp Asn Gln Leu Val Val Pro Ser Glu Gly
        355                 360                 365

Leu Tyr Leu Ile Tyr Ser Gln Val Leu Phe Lys Gly Gln Gly Cys Pro
    370                 375                 380

Ser Thr His Val Leu Leu Thr His Thr Ile Ser Arg Ile Ala Val Ser
385                 390                 395                 400

Tyr Gln Thr Lys Val Asn Leu Leu Ser Ala Ile Lys Ser Pro Cys Gln
                405                 410                 415

Arg Glu Thr Pro Glu Gly Ala Glu Ala Lys Pro Trp Tyr Glu Pro Ile
            420                 425                 430

Tyr Leu Gly Gly Val Phe Gln Leu Glu Lys Gly Asp Arg Leu Ser Ala
        435                 440                 445

Glu Ile Asn Arg Pro Asp Tyr Leu Asn Phe Arg Glu Ser Gly Gln Val
    450                 455                 460

Tyr Phe Gly Ile Ile Ala Leu Gly Gly Gly Gly Ser Glu Ser Lys Tyr
465                 470                 475                 480

Gly Pro Pro Cys Pro Pro Cys Pro Ala Pro Glu Phe Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser Gln Glu Asp
        515                 520                 525

Pro Glu Val Gln Phe Asn Trp Tyr Val Asp Gly Val Glu Val His Asn
    530                 535                 540

Ala Lys Thr Lys Pro Arg Glu Glu Gln Phe Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Gly Leu Pro Ser Ser Ile Glu Lys
            580                 585                 590

Thr Ile Ser Lys Ala Lys Gly Gln Pro Arg Glu Pro Gln Val Tyr Thr
        595                 600                 605

Leu Pro Pro Ser Gln Glu Glu Met Thr Lys Asn Gln Val Ser Leu Thr
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655
```

```
Asp Ser Asp Gly Ser Phe Phe Leu Tyr Ser Arg Leu Thr Val Asp Lys
            660                 665                 670

Ser Arg Trp Gln Glu Gly Asn Val Phe Ser Cys Ser Val Met His Glu
        675                 680                 685

Ala Leu His Asn His Tyr Thr Gln Lys Ser Leu Ser Leu Ser Leu Gly
    690                 695                 700

Lys
705


<210> SEQ ID NO 110
<211> LENGTH: 704
<212> TYPE: PRT
<213> ORGANISM: Artificial Sequence
<220> FEATURE:
<223> OTHER INFORMATION: Synthetic: fusion protein

<400> SEQUENCE: 110

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu Gly Gly Gly
145                 150                 155                 160

Gly Ser Ser Ser Arg Thr Pro Ser Asp Lys Pro Val Ala His Val Val
                165                 170                 175

Ala Asn Pro Gln Ala Glu Gly Gln Leu Gln Trp Leu Asn Arg Arg Ala
            180                 185                 190

Asn Ala Leu Leu Ala Asn Gly Val Glu Leu Arg Asp Asn Gln Leu Val
        195                 200                 205

Val Pro Ser Glu Gly Leu Tyr Leu Ile Tyr Ser Gln Val Leu Phe Lys
    210                 215                 220

Gly Gln Gly Cys Pro Ser Thr His Val Leu Leu Thr His Thr Ile Ser
225                 230                 235                 240

Arg Ile Ala Val Ser Tyr Gln Thr Lys Val Asn Leu Leu Ser Ala Ile
                245                 250                 255

Lys Ser Pro Cys Gln Arg Glu Thr Pro Glu Gly Ala Glu Ala Lys Pro
            260                 265                 270

Trp Tyr Glu Pro Ile Tyr Leu Gly Gly Val Phe Gln Leu Glu Lys Gly
        275                 280                 285

Asp Arg Leu Ser Ala Glu Ile Asn Arg Pro Asp Tyr Leu Asn Phe Arg
    290                 295                 300
```

```
Glu Ser Gly Gln Val Tyr Phe Gly Ile Ile Ala Leu Gly Gly Gly Gly
305                 310                 315                 320

Ser Ser Ser Arg Thr Pro Ser Asp Lys Pro Val Ala His Val Val Ala
                325                 330                 335

Asn Pro Gln Ala Glu Gly Gln Leu Gln Trp Leu Asn Arg Arg Ala Asn
            340                 345                 350

Ala Leu Leu Ala Asn Gly Val Glu Leu Arg Asp Asn Gln Leu Val Val
        355                 360                 365

Pro Ser Glu Gly Leu Tyr Leu Ile Tyr Ser Gln Val Leu Phe Lys Gly
    370                 375                 380

Gln Gly Cys Pro Ser Thr His Val Leu Leu Thr His Thr Ile Ser Arg
385                 390                 395                 400

Ile Ala Val Ser Tyr Gln Thr Lys Val Asn Leu Leu Ser Ala Ile Lys
                405                 410                 415

Ser Pro Cys Gln Arg Glu Thr Pro Glu Gly Ala Glu Ala Lys Pro Trp
            420                 425                 430

Tyr Glu Pro Ile Tyr Leu Gly Gly Val Phe Gln Leu Glu Lys Gly Asp
        435                 440                 445

Arg Leu Ser Ala Glu Ile Asn Arg Pro Asp Tyr Leu Asn Phe Arg Glu
    450                 455                 460

Ser Gly Gln Val Tyr Phe Gly Ile Ile Ala Leu Glu Ser Lys Tyr Gly
465                 470                 475                 480

Pro Pro Cys Pro Pro Cys Pro Ala Pro Glu Phe Leu Gly Gly Pro Ser
                485                 490                 495

Val Phe Leu Phe Pro Pro Lys Pro Lys Asp Thr Leu Met Ile Ser Arg
            500                 505                 510

Thr Pro Glu Val Thr Cys Val Val Val Asp Val Ser Gln Glu Asp Pro
        515                 520                 525

Glu Val Gln Phe Asn Trp Tyr Val Asp Gly Val Glu Val His Asn Ala
    530                 535                 540

Lys Thr Lys Pro Arg Glu Glu Gln Phe Asn Ser Thr Tyr Arg Val Val
545                 550                 555                 560

Ser Val Leu Thr Val Leu His Gln Asp Trp Leu Asn Gly Lys Glu Tyr
                565                 570                 575

Lys Cys Lys Val Ser Asn Lys Gly Leu Pro Ser Ser Ile Glu Lys Thr
            580                 585                 590

Ile Ser Lys Ala Lys Gly Gln Pro Arg Glu Pro Gln Val Tyr Thr Leu
        595                 600                 605

Pro Pro Ser Gln Glu Glu Met Thr Lys Asn Gln Val Ser Leu Thr Cys
    610                 615                 620

Leu Val Lys Gly Phe Tyr Pro Ser Asp Ile Ala Val Glu Trp Glu Ser
625                 630                 635                 640

Asn Gly Gln Pro Glu Asn Asn Tyr Lys Thr Thr Pro Pro Val Leu Asp
                645                 650                 655

Ser Asp Gly Ser Phe Phe Leu Tyr Ser Arg Leu Thr Val Asp Lys Ser
            660                 665                 670

Arg Trp Gln Glu Gly Asn Val Phe Ser Cys Ser Val Met His Glu Ala
        675                 680                 685

Leu His Asn His Tyr Thr Gln Lys Ser Leu Ser Leu Ser Leu Gly Lys
    690                 695                 700
```

<210> SEQ ID NO 111
<211> LENGTH: 694
<212> TYPE: PRT

```
<213> ORGANISM: Artificial Sequence
<220> FEATURE:
<223> OTHER INFORMATION: Synthetic: fusion protein

<400> SEQUENCE: 111

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu Ser Ser Arg
145                 150                 155                 160

Thr Pro Ser Asp Lys Pro Val Ala His Val Val Ala Asn Pro Gln Ala
                165                 170                 175

Glu Gly Gln Leu Gln Trp Leu Asn Arg Arg Ala Asn Ala Leu Leu Ala
            180                 185                 190

Asn Gly Val Glu Leu Arg Asp Asn Gln Leu Val Val Pro Ser Glu Gly
        195                 200                 205

Leu Tyr Leu Ile Tyr Ser Gln Val Leu Phe Lys Gly Gln Gly Cys Pro
    210                 215                 220

Ser Thr His Val Leu Leu Thr His Thr Ile Ser Arg Ile Ala Val Ser
225                 230                 235                 240

Tyr Gln Thr Lys Val Asn Leu Leu Ser Ala Ile Lys Ser Pro Cys Gln
                245                 250                 255

Arg Glu Thr Pro Glu Gly Ala Glu Ala Lys Pro Trp Tyr Glu Pro Ile
            260                 265                 270

Tyr Leu Gly Gly Val Phe Gln Leu Glu Lys Gly Asp Arg Leu Ser Ala
        275                 280                 285

Glu Ile Asn Arg Pro Asp Tyr Leu Asn Phe Arg Glu Ser Gly Gln Val
    290                 295                 300

Tyr Phe Gly Ile Ile Ala Leu Ser Ser Arg Thr Pro Ser Asp Lys Pro
305                 310                 315                 320

Val Ala His Val Val Ala Asn Pro Gln Ala Glu Gly Gln Leu Gln Trp
                325                 330                 335

Leu Asn Arg Arg Ala Asn Ala Leu Leu Ala Asn Gly Val Glu Leu Arg
            340                 345                 350

Asp Asn Gln Leu Val Val Pro Ser Glu Gly Leu Tyr Leu Ile Tyr Ser
        355                 360                 365

Gln Val Leu Phe Lys Gly Gln Gly Cys Pro Ser Thr His Val Leu Leu
    370                 375                 380

Thr His Thr Ile Ser Arg Ile Ala Val Ser Tyr Gln Thr Lys Val Asn
```

```
385                 390                 395                 400

Leu Leu Ser Ala Ile Lys Ser Pro Cys Gln Arg Glu Thr Pro Glu Gly
                405                 410                 415

Ala Glu Ala Lys Pro Trp Tyr Glu Pro Ile Tyr Leu Gly Gly Val Phe
            420                 425                 430

Gln Leu Glu Lys Gly Asp Arg Leu Ser Ala Glu Ile Asn Arg Pro Asp
        435                 440                 445

Tyr Leu Asn Phe Arg Glu Ser Gly Gln Val Tyr Phe Gly Ile Ile Ala
    450                 455                 460

Leu Glu Ser Lys Tyr Gly Pro Pro Cys Pro Pro Cys Pro Ala Pro Glu
465                 470                 475                 480

Phe Leu Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser Gln Glu Asp Pro Glu Val Gln Phe Asn Trp Tyr Val Asp Gly
        515                 520                 525

Val Glu Val His Asn Ala Lys Thr Lys Pro Arg Glu Glu Gln Phe Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Gly Leu Pro
                565                 570                 575

Ser Ser Ile Glu Lys Thr Ile Ser Lys Ala Lys Gly Gln Pro Arg Glu
            580                 585                 590

Pro Gln Val Tyr Thr Leu Pro Pro Ser Gln Glu Glu Met Thr Lys Asn
        595                 600                 605

Gln Val Ser Leu Thr Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Arg
                645                 650                 655

Leu Thr Val Asp Lys Ser Arg Trp Gln Glu Gly Asn Val Phe Ser Cys
            660                 665                 670

Ser Val Met His Glu Ala Leu His Asn His Tyr Thr Gln Lys Ser Leu
        675                 680                 685

Ser Leu Ser Leu Gly Lys
    690
```

<210> SEQ ID NO 112
<211> LENGTH: 698
<212> TYPE: PRT
<213> ORGANISM: Artificial Sequence
<220> FEATURE:
<223> OTHER INFORMATION: Synthetic: fusion protein

<400> SEQUENCE: 112

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
```

```
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu Val Arg Ser
145                 150                 155                 160

Ser Arg Thr Pro Ser Asp Lys Pro Val Ala His Val Val Ala Asn Pro
                165                 170                 175

Gln Ala Glu Gly Gln Leu Gln Trp Leu Asn Arg Arg Ala Asn Ala Leu
            180                 185                 190

Leu Ala Asn Gly Val Glu Leu Arg Asp Asn Gln Leu Val Val Pro Ser
        195                 200                 205

Glu Gly Leu Tyr Leu Ile Tyr Ser Gln Val Leu Phe Lys Gly Gln Gly
    210                 215                 220

Cys Pro Ser Thr His Val Leu Leu Thr His Thr Ile Ser Arg Ile Ala
225                 230                 235                 240

Val Ser Tyr Gln Thr Lys Val Asn Leu Leu Ser Ala Ile Lys Ser Pro
                245                 250                 255

Cys Gln Arg Glu Thr Pro Glu Gly Ala Glu Ala Lys Pro Trp Tyr Glu
            260                 265                 270

Pro Ile Tyr Leu Gly Gly Val Phe Gln Leu Glu Lys Gly Asp Arg Leu
        275                 280                 285

Ser Ala Glu Ile Asn Arg Pro Asp Tyr Leu Asn Phe Arg Glu Ser Gly
    290                 295                 300

Gln Val Tyr Phe Gly Ile Ile Ala Leu Val Arg Ser Ser Arg Thr Pro
305                 310                 315                 320

Ser Asp Lys Pro Val Ala His Val Val Ala Asn Pro Gln Ala Glu Gly
                325                 330                 335

Gln Leu Gln Trp Leu Asn Arg Arg Ala Asn Ala Leu Leu Ala Asn Gly
            340                 345                 350

Val Glu Leu Arg Asp Asn Gln Leu Val Val Pro Ser Glu Gly Leu Tyr
        355                 360                 365

Leu Ile Tyr Ser Gln Val Leu Phe Lys Gly Gln Gly Cys Pro Ser Thr
    370                 375                 380

His Val Leu Leu Thr His Thr Ile Ser Arg Ile Ala Val Ser Tyr Gln
385                 390                 395                 400

Thr Lys Val Asn Leu Leu Ser Ala Ile Lys Ser Pro Cys Gln Arg Glu
                405                 410                 415

Thr Pro Glu Gly Ala Glu Ala Lys Pro Trp Tyr Glu Pro Ile Tyr Leu
            420                 425                 430

Gly Gly Val Phe Gln Leu Glu Lys Gly Asp Arg Leu Ser Ala Glu Ile
        435                 440                 445

Asn Arg Pro Asp Tyr Leu Asn Phe Arg Glu Ser Gly Gln Val Tyr Phe
    450                 455                 460

Gly Ile Ile Ala Leu Glu Ser Lys Tyr Gly Pro Pro Cys Pro Pro Cys
465                 470                 475                 480
```

```
Pro Ala Pro Glu Phe Leu Gly Gly Pro Ser Val Phe Leu Phe Pro Pro
                485                 490                 495

Lys Pro Lys Asp Thr Leu Met Ile Ser Arg Thr Pro Glu Val Thr Cys
            500                 505                 510

Val Val Val Asp Val Ser Gln Glu Asp Pro Glu Val Gln Phe Asn Trp
        515                 520                 525

Tyr Val Asp Gly Val Glu Val His Asn Ala Lys Thr Lys Pro Arg Glu
    530                 535                 540

Glu Gln Phe Asn Ser Thr Tyr Arg Val Val Ser Val Leu Thr Val Leu
545                 550                 555                 560

His Gln Asp Trp Leu Asn Gly Lys Glu Tyr Lys Cys Lys Val Ser Asn
                565                 570                 575

Lys Gly Leu Pro Ser Ser Ile Glu Lys Thr Ile Ser Lys Ala Lys Gly
            580                 585                 590

Gln Pro Arg Glu Pro Gln Val Tyr Thr Leu Pro Pro Ser Gln Glu Glu
        595                 600                 605

Met Thr Lys Asn Gln Val Ser Leu Thr Cys Leu Val Lys Gly Phe Tyr
    610                 615                 620

Pro Ser Asp Ile Ala Val Glu Trp Glu Ser Asn Gly Gln Pro Glu Asn
625                 630                 635                 640

Asn Tyr Lys Thr Thr Pro Pro Val Leu Asp Ser Asp Gly Ser Phe Phe
                645                 650                 655

Leu Tyr Ser Arg Leu Thr Val Asp Lys Ser Arg Trp Gln Glu Gly Asn
            660                 665                 670

Val Phe Ser Cys Ser Val Met His Glu Ala Leu His Asn His Tyr Thr
        675                 680                 685

Gln Lys Ser Leu Ser Leu Ser Leu Gly Lys
    690                 695


<210> SEQ ID NO 113
<211> LENGTH: 712
<212> TYPE: PRT
<213> ORGANISM: Artificial Sequence
<220> FEATURE:
<223> OTHER INFORMATION: Synthetic: fusion protein

<400> SEQUENCE: 113

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Val Arg Ser
225                 230                 235                 240

Ser Ser Arg Thr Pro Ser Asp Lys Pro Val Ala His Val Val Ala Asn
                245                 250                 255

Pro Gln Ala Glu Gly Gln Leu Gln Trp Leu Asn Arg Arg Ala Asn Ala
            260                 265                 270

Leu Leu Ala Asn Gly Val Glu Leu Arg Asp Asn Gln Leu Val Val Pro
        275                 280                 285

Ser Glu Gly Leu Tyr Leu Ile Tyr Ser Gln Val Leu Phe Lys Gly Gln
    290                 295                 300

Gly Cys Pro Ser Thr His Val Leu Leu Thr His Thr Ile Ser Arg Ile
305                 310                 315                 320

Ala Val Ser Tyr Gln Thr Lys Val Asn Leu Leu Ser Ala Ile Lys Ser
                325                 330                 335

Pro Cys Gln Arg Glu Thr Pro Glu Gly Ala Glu Ala Lys Pro Trp Tyr
            340                 345                 350

Glu Pro Ile Tyr Leu Gly Gly Val Phe Gln Leu Glu Lys Gly Asp Arg
        355                 360                 365

Leu Ser Ala Glu Ile Asn Arg Pro Asp Tyr Leu Asn Phe Arg Glu Ser
    370                 375                 380

Gly Gln Val Tyr Phe Gly Ile Ile Ala Leu Gly Gly Gly Gly Ser Ser
385                 390                 395                 400

Ser Arg Thr Pro Ser Asp Lys Pro Val Ala His Val Val Ala Asn Pro
                405                 410                 415

Gln Ala Glu Gly Gln Leu Gln Trp Leu Asn Arg Arg Ala Asn Ala Leu
            420                 425                 430

Leu Ala Asn Gly Val Glu Leu Arg Asp Asn Gln Leu Val Val Pro Ser
        435                 440                 445

Glu Gly Leu Tyr Leu Ile Tyr Ser Gln Val Leu Phe Lys Gly Gln Gly
    450                 455                 460

Cys Pro Ser Thr His Val Leu Leu Thr His Thr Ile Ser Arg Ile Ala
465                 470                 475                 480

Val Ser Tyr Gln Thr Lys Val Asn Leu Leu Ser Ala Ile Lys Ser Pro
                485                 490                 495

Cys Gln Arg Glu Thr Pro Glu Gly Ala Glu Ala Lys Pro Trp Tyr Glu
            500                 505                 510

Pro Ile Tyr Leu Gly Gly Val Phe Gln Leu Glu Lys Gly Asp Arg Leu
        515                 520                 525

Ser Ala Glu Ile Asn Arg Pro Asp Tyr Leu Asn Phe Arg Glu Ser Gly
    530                 535                 540

Gln Val Tyr Phe Gly Ile Ile Ala Leu Gly Gly Gly Gly Ser Ser Ser
545                 550                 555                 560
```

```
Arg Thr Pro Ser Asp Lys Pro Val Ala His Val Val Ala Asn Pro Gln
                565                 570                 575

Ala Glu Gly Gln Leu Gln Trp Leu Asn Arg Arg Ala Asn Ala Leu Leu
            580                 585                 590

Ala Asn Gly Val Glu Leu Arg Asp Asn Gln Leu Val Val Pro Ser Glu
        595                 600                 605

Gly Leu Tyr Leu Ile Tyr Ser Gln Val Leu Phe Lys Gly Gln Gly Cys
    610                 615                 620

Pro Ser Thr His Val Leu Leu Thr His Thr Ile Ser Arg Ile Ala Val
625                 630                 635                 640

Ser Tyr Gln Thr Lys Val Asn Leu Leu Ser Ala Ile Lys Ser Pro Cys
                645                 650                 655

Gln Arg Glu Thr Pro Glu Gly Ala Glu Ala Lys Pro Trp Tyr Glu Pro
            660                 665                 670

Ile Tyr Leu Gly Gly Val Phe Gln Leu Glu Lys Gly Asp Arg Leu Ser
        675                 680                 685

Ala Glu Ile Asn Arg Pro Asp Tyr Leu Asn Phe Arg Glu Ser Gly Gln
    690                 695                 700

Val Tyr Phe Gly Ile Ile Ala Leu
705                 710


<210> SEQ ID NO 114
<211> LENGTH: 708
<212> TYPE: PRT
<213> ORGANISM: Artificial Sequence
<220> FEATURE:
<223> OTHER INFORMATION: Synthetic: fusion protein

<400> SEQUENCE: 114

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Ser
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205
```

```
Met His Glu Ala Leu His Asn His Tyr Thr Gln Lys Ser Leu Ser Leu
    210                 215                 220

Ser Pro Gly Lys Gly Gly Gly Gly Ser Val Arg Ser Ser Ser Arg Thr
225                 230                 235                 240

Pro Ser Asp Lys Pro Val Ala His Val Val Ala Asn Pro Gln Ala Glu
                245                 250                 255

Gly Gln Leu Gln Trp Leu Asn Arg Arg Ala Asn Ala Leu Leu Ala Asn
            260                 265                 270

Gly Val Glu Leu Arg Asp Asn Gln Leu Val Val Pro Ser Glu Gly Leu
        275                 280                 285

Tyr Leu Ile Tyr Ser Gln Val Leu Phe Lys Gly Gln Gly Cys Pro Ser
    290                 295                 300

Thr His Val Leu Leu Thr His Thr Ile Ser Arg Ile Ala Val Ser Tyr
305                 310                 315                 320

Gln Thr Lys Val Asn Leu Leu Ser Ala Ile Lys Ser Pro Cys Gln Arg
                325                 330                 335

Glu Thr Pro Glu Gly Ala Glu Ala Lys Pro Trp Tyr Glu Pro Ile Tyr
            340                 345                 350

Leu Gly Gly Val Phe Gln Leu Glu Lys Gly Asp Arg Leu Ser Ala Glu
        355                 360                 365

Ile Asn Arg Pro Asp Tyr Leu Asn Phe Arg Glu Ser Gly Gln Val Tyr
    370                 375                 380

Phe Gly Ile Ile Ala Leu Gly Gly Gly Gly Ser Ser Ser Arg Thr Pro
385                 390                 395                 400

Ser Asp Lys Pro Val Ala His Val Val Ala Asn Pro Gln Ala Glu Gly
                405                 410                 415

Gln Leu Gln Trp Leu Asn Arg Arg Ala Asn Ala Leu Leu Ala Asn Gly
            420                 425                 430

Val Glu Leu Arg Asp Asn Gln Leu Val Val Pro Ser Glu Gly Leu Tyr
        435                 440                 445

Leu Ile Tyr Ser Gln Val Leu Phe Lys Gly Gln Gly Cys Pro Ser Thr
    450                 455                 460

His Val Leu Leu Thr His Thr Ile Ser Arg Ile Ala Val Ser Tyr Gln
465                 470                 475                 480

Thr Lys Val Asn Leu Leu Ser Ala Ile Lys Ser Pro Cys Gln Arg Glu
                485                 490                 495

Thr Pro Glu Gly Ala Glu Ala Lys Pro Trp Tyr Glu Pro Ile Tyr Leu
            500                 505                 510

Gly Gly Val Phe Gln Leu Glu Lys Gly Asp Arg Leu Ser Ala Glu Ile
        515                 520                 525

Asn Arg Pro Asp Tyr Leu Asn Phe Arg Glu Ser Gly Gln Val Tyr Phe
    530                 535                 540

Gly Ile Ile Ala Leu Gly Gly Gly Gly Ser Ser Ser Arg Thr Pro Ser
545                 550                 555                 560

Asp Lys Pro Val Ala His Val Val Ala Asn Pro Gln Ala Glu Gly Gln
                565                 570                 575

Leu Gln Trp Leu Asn Arg Arg Ala Asn Ala Leu Leu Ala Asn Gly Val
            580                 585                 590

Glu Leu Arg Asp Asn Gln Leu Val Val Pro Ser Glu Gly Leu Tyr Leu
        595                 600                 605

Ile Tyr Ser Gln Val Leu Phe Lys Gly Gln Gly Cys Pro Ser Thr His
    610                 615                 620

Val Leu Leu Thr His Thr Ile Ser Arg Ile Ala Val Ser Tyr Gln Thr
```

```
625                 630                 635                 640

Lys Val Asn Leu Leu Ser Ala Ile Lys Ser Pro Cys Gln Arg Glu Thr
                645                 650                 655

Pro Glu Gly Ala Glu Ala Lys Pro Trp Tyr Glu Pro Ile Tyr Leu Gly
            660                 665                 670

Gly Val Phe Gln Leu Glu Lys Gly Asp Arg Leu Ser Ala Glu Ile Asn
        675                 680                 685

Arg Pro Asp Tyr Leu Asn Phe Arg Glu Ser Gly Gln Val Tyr Phe Gly
    690                 695                 700

Ile Ile Ala Leu
705


<210> SEQ ID NO 115
<211> LENGTH: 712
<212> TYPE: PRT
<213> ORGANISM: Artificial Sequence
<220> FEATURE:
<223> OTHER INFORMATION: Synthetic: fusion protein

<400> SEQUENCE: 115

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu Gly Gly Gly
145                 150                 155                 160

Gly Ser Ser Ser Arg Thr Pro Ser Asp Lys Pro Val Ala His Val Val
                165                 170                 175

Ala Asn Pro Gln Ala Glu Gly Gln Leu Gln Trp Leu Asn Arg Arg Ala
            180                 185                 190

Asn Ala Leu Leu Ala Asn Gly Val Glu Leu Arg Asp Asn Gln Leu Val
        195                 200                 205

Val Pro Ser Glu Gly Leu Tyr Leu Ile Tyr Ser Gln Val Leu Phe Lys
    210                 215                 220

Gly Gln Gly Cys Pro Ser Thr His Val Leu Leu Thr His Thr Ile Ser
225                 230                 235                 240

Arg Ile Ala Val Ser Tyr Gln Thr Lys Val Asn Leu Leu Ser Ala Ile
                245                 250                 255

Lys Ser Pro Cys Gln Arg Glu Thr Pro Glu Gly Ala Glu Ala Lys Pro
            260                 265                 270

Trp Tyr Glu Pro Ile Tyr Leu Gly Gly Val Phe Gln Leu Glu Lys Gly
```

```
        275                 280                 285

Asp Arg Leu Ser Ala Glu Ile Asn Arg Pro Asp Tyr Leu Asn Phe Arg
    290                 295                 300

Glu Ser Gly Gln Val Tyr Phe Gly Ile Ile Ala Leu Gly Gly Gly Gly
305                 310                 315                 320

Ser Ser Ser Arg Thr Pro Ser Asp Lys Pro Val Ala His Val Val Ala
                325                 330                 335

Asn Pro Gln Ala Glu Gly Gln Leu Gln Trp Leu Asn Arg Arg Ala Asn
            340                 345                 350

Ala Leu Leu Ala Asn Gly Val Glu Leu Arg Asp Asn Gln Leu Val Val
        355                 360                 365

Pro Ser Glu Gly Leu Tyr Leu Ile Tyr Ser Gln Val Leu Phe Lys Gly
    370                 375                 380

Gln Gly Cys Pro Ser Thr His Val Leu Leu Thr His Thr Ile Ser Arg
385                 390                 395                 400

Ile Ala Val Ser Tyr Gln Thr Lys Val Asn Leu Leu Ser Ala Ile Lys
                405                 410                 415

Ser Pro Cys Gln Arg Glu Thr Pro Glu Gly Ala Glu Ala Lys Pro Trp
            420                 425                 430

Tyr Glu Pro Ile Tyr Leu Gly Gly Val Phe Gln Leu Glu Lys Gly Asp
        435                 440                 445

Arg Leu Ser Ala Glu Ile Asn Arg Pro Asp Tyr Leu Asn Phe Arg Glu
    450                 455                 460

Ser Gly Gln Val Tyr Phe Gly Ile Ile Ala Leu Gly Gly Gly Gly Ser
465                 470                 475                 480

Glu Pro Lys Ser Ser Asp Lys Thr His Thr Cys Pro Pro Cys Pro Ala
                485                 490                 495

Pro Glu Ala Ala Gly Gly Pro Ser Val Phe Leu Phe Pro Pro Lys Pro
            500                 505                 510

Lys Asp Thr Leu Met Ile Ser Arg Thr Pro Glu Val Thr Cys Val Val
        515                 520                 525

Val Asp Val Ser His Glu Asp Pro Glu Val Lys Phe Asn Trp Tyr Val
    530                 535                 540

Asp Gly Val Glu Val His Asn Ala Lys Thr Lys Pro Arg Glu Glu Gln
545                 550                 555                 560

Tyr Asn Ser Thr Tyr Arg Val Val Ser Val Leu Thr Val Leu His Gln
                565                 570                 575

Asp Trp Leu Asn Gly Lys Glu Tyr Lys Cys Lys Val Ser Asn Lys Ala
            580                 585                 590

Leu Pro Ala Ser Ile Glu Lys Thr Ile Ser Lys Ala Lys Gly Gln Pro
        595                 600                 605

Arg Glu Pro Gln Val Tyr Thr Leu Pro Pro Ser Arg Asp Glu Leu Thr
    610                 615                 620

Lys Asn Gln Val Ser Leu Thr Cys Leu Val Lys Gly Phe Tyr Pro Ser
625                 630                 635                 640

Asp Ile Ala Val Glu Trp Glu Ser Asn Gly Gln Pro Glu Asn Asn Tyr
                645                 650                 655

Lys Thr Thr Pro Pro Val Leu Asp Ser Asp Gly Ser Phe Phe Leu Tyr
            660                 665                 670

Ser Lys Leu Thr Val Asp Lys Ser Arg Trp Gln Gln Gly Asn Val Phe
        675                 680                 685

Ser Cys Ser Val Met His Glu Ala Leu His Asn His Tyr Thr Gln Lys
    690                 695                 700
```

```
Ser Leu Ser Leu Ser Pro Gly Lys
705                 710


<210> SEQ ID NO 116
<211> LENGTH: 708
<212> TYPE: PRT
<213> ORGANISM: Artificial Sequence
<220> FEATURE:
<223> OTHER INFORMATION: Synthetic: fusion protein

<400> SEQUENCE: 116

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asn Phe
    130                 135                 140

Arg Glu Ser Gly Gln Val Tyr Phe Gly Ile Ile Ala Leu Gly Gly Gly
145                 150                 155                 160

Gly Ser Ser Ser Arg Thr Pro Ser Asp Lys Pro Val Ala His Val Val
                165                 170                 175

Ala Asn Pro Gln Ala Glu Gly Gln Leu Gln Trp Leu Asn Arg Arg Ala
            180                 185                 190

Asn Ala Leu Leu Ala Asn Gly Val Glu Leu Arg Asp Asn Gln Leu Val
        195                 200                 205

Val Pro Ser Glu Gly Leu Tyr Leu Ile Tyr Ser Gln Val Leu Phe Lys
    210                 215                 220

Gly Gln Gly Cys Pro Ser Thr His Val Leu Leu Thr His Thr Ile Ser
225                 230                 235                 240

Arg Ile Ala Val Ser Tyr Gln Thr Lys Val Asn Leu Leu Ser Ala Ile
                245                 250                 255

Lys Ser Pro Cys Gln Arg Glu Thr Pro Glu Gly Ala Glu Ala Lys Pro
            260                 265                 270

Trp Tyr Glu Pro Ile Tyr Leu Gly Gly Val Phe Gln Leu Glu Lys Gly
        275                 280                 285

Asp Arg Leu Ser Ala Glu Ile Asn Arg Pro Asp Tyr Leu Asn Phe Arg
    290                 295                 300

Glu Ser Gly Gln Val Tyr Phe Gly Ile Ile Ala Leu Gly Gly Gly Gly
305                 310                 315                 320

Ser Ser Ser Arg Thr Pro Ser Asp Lys Pro Val Ala His Val Val Ala
                325                 330                 335

Asn Pro Gln Ala Glu Gly Gln Leu Gln Trp Leu Asn Arg Arg Ala Asn
            340                 345                 350
```

```
Ala Leu Leu Ala Asn Gly Val Glu Leu Arg Asp Asn Gln Leu Val Val
        355                 360                 365

Pro Ser Glu Gly Leu Tyr Leu Ile Tyr Ser Gln Val Leu Phe Lys Gly
    370                 375                 380

Gln Gly Cys Pro Ser Thr His Val Leu Leu Thr His Thr Ile Ser Arg
385                 390                 395                 400

Ile Ala Val Ser Tyr Gln Thr Lys Val Asn Leu Leu Ser Ala Ile Lys
                405                 410                 415

Ser Pro Cys Gln Arg Glu Thr Pro Glu Gly Ala Glu Ala Lys Pro Trp
            420                 425                 430

Tyr Glu Pro Ile Tyr Leu Gly Gly Val Phe Gln Leu Glu Lys Gly Asp
        435                 440                 445

Arg Leu Ser Ala Glu Ile Asn Arg Pro Asp Tyr Leu Asn Phe Arg Glu
    450                 455                 460

Ser Gly Gln Val Tyr Phe Gly Ile Ile Ala Leu Gly Gly Gly Gly Ser
465                 470                 475                 480

Glu Arg Lys Ser Ser Val Glu Cys Pro Pro Cys Pro Ala Pro Pro Val
                485                 490                 495

Ala Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Gln Phe Asn Trp Tyr Val Asp Gly Val Glu
    530                 535                 540

Val His Asn Ala Lys Thr Lys Pro Arg Glu Glu Gln Phe Asn Ser Thr
545                 550                 555                 560

Phe Arg Val Val Ser Val Leu Thr Val Val His Gln Asp Trp Leu Asn
                565                 570                 575

Gly Lys Glu Tyr Lys Cys Lys Val Ser Asn Lys Gly Leu Pro Ala Ser
            580                 585                 590

Ile Glu Lys Thr Ile Ser Lys Thr Lys Gly Gln Pro Arg Glu Pro Gln
        595                 600                 605

Val Tyr Thr Leu Pro Pro Ser Arg Glu Glu Met Thr Lys Asn Gln Val
    610                 615                 620

Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Met Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Met His Glu Ala Leu His Asn His Tyr Thr Gln Lys Ser Leu Ser Leu
    690                 695                 700

Ser Pro Gly Lys
705
```

<210> SEQ ID NO 117
<211> LENGTH: 694
<212> TYPE: PRT
<213> ORGANISM: Artificial Sequence
<220> FEATURE:
<223> OTHER INFORMATION: Synthetic: fusion protein

<400> SEQUENCE: 117

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Val Arg Ser Ser Ser Arg Thr Pro Ser Asp Lys
225                 230                 235                 240

Pro Val Ala His Val Val Ala Asn Pro Gln Ala Glu Gly Gln Leu Gln
                245                 250                 255

Trp Leu Asn Arg Arg Ala Asn Ala Leu Leu Ala Asn Gly Val Glu Leu
            260                 265                 270

Arg Asp Asn Gln Leu Val Val Pro Ser Glu Gly Leu Tyr Leu Ile Tyr
        275                 280                 285

Ser Gln Val Leu Phe Lys Gly Gln Gly Cys Pro Ser Thr His Val Leu
    290                 295                 300

Leu Thr His Thr Ile Ser Arg Ile Ala Val Ser Tyr Gln Thr Lys Val
305                 310                 315                 320

Asn Leu Leu Ser Ala Ile Lys Ser Pro Cys Gln Arg Glu Thr Pro Glu
                325                 330                 335

Gly Ala Glu Ala Lys Pro Trp Tyr Glu Pro Ile Tyr Leu Gly Gly Val
            340                 345                 350

Phe Gln Leu Glu Lys Gly Asp Arg Leu Ser Ala Glu Ile Asn Arg Pro
        355                 360                 365

Asp Tyr Leu Asn Phe Arg Glu Ser Gly Gln Val Tyr Phe Gly Ile Ile
    370                 375                 380

Ala Leu Ser Ser Arg Thr Pro Ser Asp Lys Pro Val Ala His Val Val
385                 390                 395                 400

Ala Asn Pro Gln Ala Glu Gly Gln Leu Gln Trp Leu Asn Arg Arg Ala
                405                 410                 415
```

```
Asn Ala Leu Leu Ala Asn Gly Val Glu Leu Arg Asp Asn Gln Leu Val
            420                 425                 430

Val Pro Ser Glu Gly Leu Tyr Leu Ile Tyr Ser Gln Val Leu Phe Lys
        435                 440                 445

Gly Gln Gly Cys Pro Ser Thr His Val Leu Leu Thr His Thr Ile Ser
    450                 455                 460

Arg Ile Ala Val Ser Tyr Gln Thr Lys Val Asn Leu Leu Ser Ala Ile
465                 470                 475                 480

Lys Ser Pro Cys Gln Arg Glu Thr Pro Glu Gly Ala Glu Ala Lys Pro
                485                 490                 495

Trp Tyr Glu Pro Ile Tyr Leu Gly Gly Val Phe Gln Leu Glu Lys Gly
            500                 505                 510

Asp Arg Leu Ser Ala Glu Ile Asn Arg Pro Asp Tyr Leu Asn Phe Arg
        515                 520                 525

Glu Ser Gly Gln Val Tyr Phe Gly Ile Ile Ala Leu Ser Ser Arg Thr
    530                 535                 540

Pro Ser Asp Lys Pro Val Ala His Val Val Ala Asn Pro Gln Ala Glu
545                 550                 555                 560

Gly Gln Leu Gln Trp Leu Asn Arg Arg Ala Asn Ala Leu Leu Ala Asn
                565                 570                 575

Gly Val Glu Leu Arg Asp Asn Gln Leu Val Val Pro Ser Glu Gly Leu
            580                 585                 590

Tyr Leu Ile Tyr Ser Gln Val Leu Phe Lys Gly Gln Gly Cys Pro Ser
        595                 600                 605

Thr His Val Leu Leu Thr His Thr Ile Ser Arg Ile Ala Val Ser Tyr
    610                 615                 620

Gln Thr Lys Val Asn Leu Leu Ser Ala Ile Lys Ser Pro Cys Gln Arg
625                 630                 635                 640

Glu Thr Pro Glu Gly Ala Glu Ala Lys Pro Trp Tyr Glu Pro Ile Tyr
                645                 650                 655

Leu Gly Gly Val Phe Gln Leu Glu Lys Gly Asp Arg Leu Ser Ala Glu
            660                 665                 670

Ile Asn Arg Pro Asp Tyr Leu Asn Phe Arg Glu Ser Gly Gln Val Tyr
        675                 680                 685

Phe Gly Ile Ile Ala Leu
    690
```

<210> SEQ ID NO 118
<211> LENGTH: 693
<212> TYPE: PRT
<213> ORGANISM: Artificial Sequence
<220> FEATURE:
<223> OTHER INFORMATION: Synthetic: fusion protein

<400> SEQUENCE: 118

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80
```

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Gly Ser Val Arg Ser Ser Ser Arg
225                 230                 235                 240

Thr Pro Ser Asp Lys Pro Val Ala His Val Val Ala Asn Pro Gln Ala
                245                 250                 255

Glu Gly Gln Leu Gln Trp Leu Asn Arg Arg Ala Asn Ala Leu Leu Ala
                260                 265                 270

Asn Gly Val Glu Leu Arg Asp Asn Gln Leu Val Val Pro Ser Glu Gly
        275                 280                 285

Leu Tyr Leu Ile Tyr Ser Gln Val Leu Phe Lys Gly Gln Gly Cys Pro
    290                 295                 300

Ser Thr His Val Leu Leu Thr His Thr Ile Ser Arg Ile Ala Val Ser
305                 310                 315                 320

Tyr Gln Thr Lys Val Asn Leu Leu Ser Ala Ile Lys Ser Pro Cys Gln
                325                 330                 335

Arg Glu Thr Pro Glu Gly Ala Glu Ala Lys Pro Trp Tyr Glu Pro Ile
                340                 345                 350

Tyr Leu Gly Gly Val Phe Gln Leu Glu Lys Gly Asp Arg Leu Ser Ala
        355                 360                 365

Glu Ile Asn Arg Pro Asp Tyr Leu Asn Phe Arg Glu Ser Gly Gln Val
    370                 375                 380

Tyr Phe Gly Ile Ile Ala Leu Gly Gly Gly Gly Ser Pro Val Ala His
385                 390                 395                 400

Val Val Ala Asn Pro Gln Ala Glu Gly Gln Leu Gln Trp Leu Asn Arg
                405                 410                 415

Arg Ala Asn Ala Leu Leu Ala Asn Gly Val Glu Leu Arg Asp Asn Gln
                420                 425                 430

Leu Val Val Pro Ser Glu Gly Leu Tyr Leu Ile Tyr Ser Gln Val Leu
        435                 440                 445

Phe Lys Gly Gln Gly Cys Pro Ser Thr His Val Leu Leu Thr His Thr
    450                 455                 460

Ile Ser Arg Ile Ala Val Ser Tyr Gln Thr Lys Val Asn Leu Leu Ser
465                 470                 475                 480

Ala Ile Lys Ser Pro Cys Gln Arg Glu Thr Pro Glu Gly Ala Glu Ala
                485                 490                 495

Lys Pro Trp Tyr Glu Pro Ile Tyr Leu Gly Gly Val Phe Gln Leu Glu
```

```
            500                 505                 510

Lys Gly Asp Arg Leu Ser Ala Glu Ile Asn Arg Pro Asp Tyr Leu Asn
        515                 520                 525

Phe Arg Glu Ser Gly Gln Val Tyr Phe Gly Ile Ile Ala Leu Gly Gly
    530                 535                 540

Gly Gly Ser Pro Val Ala His Val Val Ala Asn Pro Gln Ala Glu Gly
545                 550                 555                 560

Gln Leu Gln Trp Leu Asn Arg Arg Ala Asn Ala Leu Leu Ala Asn Gly
                565                 570                 575

Val Glu Leu Arg Asp Asn Gln Leu Val Val Pro Ser Glu Gly Leu Tyr
            580                 585                 590

Leu Ile Tyr Ser Gln Val Leu Phe Lys Gly Gln Gly Cys Pro Ser Thr
        595                 600                 605

His Val Leu Leu Thr His Thr Ile Ser Arg Ile Ala Val Ser Tyr Gln
    610                 615                 620

Thr Lys Val Asn Leu Leu Ser Ala Ile Lys Ser Pro Cys Gln Arg Glu
625                 630                 635                 640

Thr Pro Glu Gly Ala Glu Ala Lys Pro Trp Tyr Glu Pro Ile Tyr Leu
                645                 650                 655

Gly Gly Val Phe Gln Leu Glu Lys Gly Asp Arg Leu Ser Ala Glu Ile
            660                 665                 670

Asn Arg Pro Asp Tyr Leu Asn Phe Arg Glu Ser Gly Gln Val Tyr Phe
        675                 680                 685

Gly Ile Ile Ala Leu
    690


<210> SEQ ID NO 119
<211> LENGTH: 698
<212> TYPE: PRT
<213> ORGANISM: Artificial Sequence
<220> FEATURE:
<223> OTHER INFORMATION: Synthetic: fusion protein

<400> SEQUENCE: 119

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
```

```
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Gly Ser Gly Gly Gly Gly Ser Val
225                 230                 235                 240

Arg Ser Ser Ser Arg Thr Pro Ser Asp Lys Pro Val Ala His Val Val
                245                 250                 255

Ala Asn Pro Gln Ala Glu Gly Gln Leu Gln Trp Leu Asn Arg Arg Ala
            260                 265                 270

Asn Ala Leu Leu Ala Asn Gly Val Glu Leu Arg Asp Asn Gln Leu Val
        275                 280                 285

Val Pro Ser Glu Gly Leu Tyr Leu Ile Tyr Ser Gln Val Leu Phe Lys
    290                 295                 300

Gly Gln Gly Cys Pro Ser Thr His Val Leu Leu Thr His Thr Ile Ser
305                 310                 315                 320

Arg Ile Ala Val Ser Tyr Gln Thr Lys Val Asn Leu Leu Ser Ala Ile
                325                 330                 335

Lys Ser Pro Cys Gln Arg Glu Thr Pro Glu Gly Ala Glu Ala Lys Pro
            340                 345                 350

Trp Tyr Glu Pro Ile Tyr Leu Gly Gly Val Phe Gln Leu Glu Lys Gly
        355                 360                 365

Asp Arg Leu Ser Ala Glu Ile Asn Arg Pro Asp Tyr Leu Asn Phe Arg
    370                 375                 380

Glu Ser Gly Gln Val Tyr Phe Gly Ile Ile Ala Leu Gly Gly Gly Gly
385                 390                 395                 400

Ser Pro Val Ala His Val Val Ala Asn Pro Gln Ala Glu Gly Gln Leu
                405                 410                 415

Gln Trp Leu Asn Arg Arg Ala Asn Ala Leu Leu Ala Asn Gly Val Glu
            420                 425                 430

Leu Arg Asp Asn Gln Leu Val Val Pro Ser Glu Gly Leu Tyr Leu Ile
        435                 440                 445

Tyr Ser Gln Val Leu Phe Lys Gly Gln Gly Cys Pro Ser Thr His Val
    450                 455                 460

Leu Leu Thr His Thr Ile Ser Arg Ile Ala Val Ser Tyr Gln Thr Lys
465                 470                 475                 480

Val Asn Leu Leu Ser Ala Ile Lys Ser Pro Cys Gln Arg Glu Thr Pro
                485                 490                 495

Glu Gly Ala Glu Ala Lys Pro Trp Tyr Glu Pro Ile Tyr Leu Gly Gly
            500                 505                 510

Val Phe Gln Leu Glu Lys Gly Asp Arg Leu Ser Ala Glu Ile Asn Arg
        515                 520                 525

Pro Asp Tyr Leu Asn Phe Arg Glu Ser Gly Gln Val Tyr Phe Gly Ile
    530                 535                 540

Ile Ala Leu Gly Gly Gly Gly Ser Pro Val Ala His Val Val Ala Asn
545                 550                 555                 560

Pro Gln Ala Glu Gly Gln Leu Gln Trp Leu Asn Arg Arg Ala Asn Ala
                565                 570                 575

Leu Leu Ala Asn Gly Val Glu Leu Arg Asp Asn Gln Leu Val Val Pro
            580                 585                 590
```

```
Ser Glu Gly Leu Tyr Leu Ile Tyr Ser Gln Val Leu Phe Lys Gly Gln
        595                 600                 605

Gly Cys Pro Ser Thr His Val Leu Leu Thr His Thr Ile Ser Arg Ile
    610                 615                 620

Ala Val Ser Tyr Gln Thr Lys Val Asn Leu Leu Ser Ala Ile Lys Ser
625                 630                 635                 640

Pro Cys Gln Arg Glu Thr Pro Glu Gly Ala Glu Ala Lys Pro Trp Tyr
                645                 650                 655

Glu Pro Ile Tyr Leu Gly Gly Val Phe Gln Leu Glu Lys Gly Asp Arg
            660                 665                 670

Leu Ser Ala Glu Ile Asn Arg Pro Asp Tyr Leu Asn Phe Arg Glu Ser
        675                 680                 685

Gly Gln Val Tyr Phe Gly Ile Ile Ala Leu
    690                 695


<210> SEQ ID NO 120
<211> LENGTH: 704
<212> TYPE: PRT
<213> ORGANISM: Artificial Sequence
<220> FEATURE:
<223> OTHER INFORMATION: Synthetic: fusion protein

<400> SEQUENCE: 120

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Gly Ser Gly Gly Gly Gly Ser Val
225                 230                 235                 240

Arg Ser Ser Ser Arg Thr Pro Ser Asp Lys Pro Val Ala His Val Val
                245                 250                 255
```

```
Ala Asn Pro Gln Ala Glu Gly Gln Leu Gln Trp Leu Asn Arg Arg Ala
            260                 265                 270

Asn Ala Leu Leu Ala Asn Gly Val Glu Leu Arg Asp Asn Gln Leu Val
        275                 280                 285

Val Pro Ser Glu Gly Leu Tyr Leu Ile Tyr Ser Gln Val Leu Phe Lys
    290                 295                 300

Gly Gln Gly Cys Pro Ser Thr His Val Leu Leu Thr His Thr Ile Ser
305                 310                 315                 320

Arg Ile Ala Val Ser Tyr Gln Thr Lys Val Asn Leu Leu Ser Ala Ile
                325                 330                 335

Lys Ser Pro Cys Gln Arg Glu Thr Pro Glu Gly Ala Glu Ala Lys Pro
            340                 345                 350

Trp Tyr Glu Pro Ile Tyr Leu Gly Gly Val Phe Gln Leu Glu Lys Gly
        355                 360                 365

Asp Arg Leu Ser Ala Glu Ile Asn Arg Pro Asp Tyr Leu Asn Phe Arg
    370                 375                 380

Glu Ser Gly Gln Val Tyr Phe Gly Ile Ile Ala Leu Ser Ser Arg Thr
385                 390                 395                 400

Pro Ser Asp Lys Pro Val Ala His Val Val Ala Asn Pro Gln Ala Glu
                405                 410                 415

Gly Gln Leu Gln Trp Leu Asn Arg Arg Ala Asn Ala Leu Leu Ala Asn
            420                 425                 430

Gly Val Glu Leu Arg Asp Asn Gln Leu Val Val Pro Ser Glu Gly Leu
        435                 440                 445

Tyr Leu Ile Tyr Ser Gln Val Leu Phe Lys Gly Gln Gly Cys Pro Ser
    450                 455                 460

Thr His Val Leu Leu Thr His Thr Ile Ser Arg Ile Ala Val Ser Tyr
465                 470                 475                 480

Gln Thr Lys Val Asn Leu Leu Ser Ala Ile Lys Ser Pro Cys Gln Arg
                485                 490                 495

Glu Thr Pro Glu Gly Ala Glu Ala Lys Pro Trp Tyr Glu Pro Ile Tyr
            500                 505                 510

Leu Gly Gly Val Phe Gln Leu Glu Lys Gly Asp Arg Leu Ser Ala Glu
        515                 520                 525

Ile Asn Arg Pro Asp Tyr Leu Asn Phe Arg Glu Ser Gly Gln Val Tyr
    530                 535                 540

Phe Gly Ile Ile Ala Leu Ser Ser Arg Thr Pro Ser Asp Lys Pro Val
545                 550                 555                 560

Ala His Val Val Ala Asn Pro Gln Ala Glu Gly Gln Leu Gln Trp Leu
                565                 570                 575

Asn Arg Arg Ala Asn Ala Leu Leu Ala Asn Gly Val Glu Leu Arg Asp
            580                 585                 590

Asn Gln Leu Val Val Pro Ser Glu Gly Leu Tyr Leu Ile Tyr Ser Gln
        595                 600                 605

Val Leu Phe Lys Gly Gln Gly Cys Pro Ser Thr His Val Leu Leu Thr
    610                 615                 620

His Thr Ile Ser Arg Ile Ala Val Ser Tyr Gln Thr Lys Val Asn Leu
625                 630                 635                 640

Leu Ser Ala Ile Lys Ser Pro Cys Gln Arg Glu Thr Pro Glu Gly Ala
                645                 650                 655

Glu Ala Lys Pro Trp Tyr Glu Pro Ile Tyr Leu Gly Gly Val Phe Gln
            660                 665                 670
```

```
Leu Glu Lys Gly Asp Arg Leu Ser Ala Glu Ile Asn Arg Pro Asp Tyr
        675                 680                 685

Leu Asn Phe Arg Glu Ser Gly Gln Val Tyr Phe Gly Ile Ile Ala Leu
    690                 695                 700


<210> SEQ ID NO 121
<211> LENGTH: 2127
<212> TYPE: DNA
<213> ORGANISM: Artificial Sequence
<220> FEATURE:
<223> OTHER INFORMATION: Synthetic: Codon optimized nucleic acid
      sequence encoding SEQ ID NO 101

<400> SEQUENCE: 121

gagtccaagt atgggccacc ttgtccacca tgcccagccc ccgaatttct tggtggccct      60

tcagtctttc tcttcccacc caaacccaaa gatactctta tgatttctcg aacccccgag     120

gtgacatgcg tggtcgtaga cgtgagtcag gaagacccag aggttcagtt caactggtat     180

gtcgacggcg tagaggtgca taacgccaag actaaacccc gagaagagca gtttaactcc     240

acttacagag tggtgagtgt cttgaccgtc ctgcatcagg actggcttaa cggcaaagag     300

tataaatgta aagttagcaa taaaggactc ccaagtagca ttgaaaaaac catcagtaaa     360

gcaaagggcc aaccaagaga gccccaggtg tatacccttc cacccagtca ggaggaaatg     420

accaaaaacc aagtttccct tacttgcctt gttaagggat tctacccctc agacattgct     480

gtagagtggg agtccaatgg tcagcctgag aataattaca aaacaacacc tcctgtgttg     540

gacagcgacg gatctttctt tctctatagt cgactcactg tggacaaatc aagatggcag     600

gaggggaatg tgttctcatg ctcagtaatg catgaagccc tgcacaatca ctacacacaa     660

aagagtctct ctctgtccct tggaaagggt ggaggtggga gcgtgcgctc ttcaagccgc     720

acaccatctg ataagcctgt ggcacatgtc gttgcaaatc cacaagcaga gggacaactt     780

cagtggttga acaggcgcgc caacgcattg ctcgccaacg gtgtcgagct gcgggacaac     840

cagctggtcg tacctagtga gggtctgtac ttgatctaca gccaagtact gttcaaaggg     900

cagggctgtc ccagcaccca tgttctcttg actcatacca tatcacgaat cgcagtaagt     960

taccagacta aagtgaacct gctttccgct atcaaaagtc cctgtcaaag agagactcca    1020

gaaggggctg aggctaaacc ttggtacgaa ccaatttatc tgggaggtgt gttccagctt    1080

gagaaaggag atcgcctttc agctgagatc aatcgaccag attatttgaa ttttcgagag    1140

agcggccaag tttattttgg cataatcgca ttgggtggtg gtggtagctc ctcacgcact    1200

ccatctgaca agccagttgc tcatgtcgta gctaatcccc aggcagaggg acaacttcaa    1260

tggctgaaca gaagggcaaa cgccctgttg gccaatggtg tggagttgag agacaatcag    1320

ctggttgtcc cttctgaggg actttatctt atatatagcc aagtgttgtt caaaggtcaa    1380

gggtgcccct caactcatgt tctgttgacc cataccataa gtcgaatcgc agtgagttac    1440

caaacaaagg tcaatctctt gtccgccata aagagcccct gccaacggga aacacccgaa    1500

ggagccgagg caaaaccatg gtacgaacca atatacctcg gggagtgtt ccagctggag    1560

aagggagacc gactttcagc tgaaatcaac aggcccgact atcttaactt cagggagtca    1620

gggcaggtct actttggaat aatagcattg ggcggaggcg gatccagcag cagaactcct    1680

agcgacaagc ccgttgctca tgtcgtagcc aatccacaag ccgaaggcca gctgcagtgg    1740

cttaatcgac gggccaatgc cctgttggca aacggagtcg agcttaggga taatcagctc    1800

gttgttccaa gtgaaggatt gtatttgatc tacagccaag ttctgttcaa gggtcagggt    1860
```

```
tgcccctcta cccatgtttt gttgacacac acaatcagtc gcattgctgt atcctatcaa   1920

accaaggtca atttgctgtc cgcaatcaag agcccatgcc agagagagac tccagaaggc   1980

gcagaagcta agccctggta cgagccaatt taccttggcg gggttttcca gcttgagaaa   2040

ggagataggc tgagcgcaga aatcaatcgg cccgactact tgaatttccg cgaaagcggt   2100

caagtgtatt ttggtatcat agcactt                                       2127
```

<210> SEQ ID NO 122
<211> LENGTH: 2097
<212> TYPE: DNA
<213> ORGANISM: Artificial Sequence
<220> FEATURE:
<223> OTHER INFORMATION: Synthetic: Codon optimized nucleic acid sequence encoding SEQ ID NO 102

<400> SEQUENCE: 122

```
gaatctaagt acggtccccc ttgtccacca tgtccagccc ccgagtttct cggagggccc     60

agtgtctttc ttttccctcc taaacccaag gatactctca tgattagccg aacacctgaa    120

gtaacatgtg ttgttgtgga cgttagtcaa gaagaccccg aagttcaatt taactggtat    180

gtggatggcg tagaggtaca caacgcaaag actaaaccac gagaagagca gttcaactcc    240

acttatcgag tagttagtgt gttgacagta ctccatcaag actggctcaa cggcaaagaa    300

tataagtgta aagttagtaa caaaggactc cccagtagca ttgaaaagac tatctccaag    360

gcaaaagggc aaccaaggga gccccaggtg tataccttgc caccctcaca agaggagatg    420

acaaagaacc aggtcagtct cacctgtctg gttaagggtt tctatccttc tgacattgcc    480

gttgaatggg agtctaacgg ccagcctgaa aataactaca agactacacc tcccgtcctg    540

gatagcgatg gtagtttttt cctctattcc aggctcactg tagacaagtc aaggtggcag    600

gaaggcaatg ttttcagctg ctctgtcatg catgaggcac tccacaatca ttatacacaa    660

aaaagtctca gtttgtcctt gggcaagggt ggaggcggga gcgttcgcag ctcctctcgg    720

actccaagcg acaaacctgt tgctcatgtc gtcgccaatc ctcaggcaga aggccaactg    780

caatggctga acagacgcgc taatgcattg ttggccaacg gcgttgagtt gagagacaac    840

caactcgttg taccctccga gggactttat ctgatatact ctcaagtatt gtttaagggt    900

caaggttgtc catcaaccca cgtattgctg acccatacca tttctagaat tgccgtaagt    960

tatcagacta aagttaattt gttgagcgca attaaaagtc cttgtcaacg cgaaactcct   1020

gagggagcag aagcaaaacc ctggtacgaa cccatttatt tgggaggggt atttcagctg   1080

gaaaaggggg atcggctgtc agccgaaatt aatcgccctg attatctgaa cttcagagaa   1140

agcggtcaag tctacttcgg catcatagcc ctttcatctc gcacaccaag tgataagccc   1200

gttgctcacg tcgtggcaaa cccacaagcc gaggggcaac tccagtggtt gaaccgcagg   1260

gcaaatgctc tcttggctaa cggggtcgaa ttgagggata atcagctcgt tgtcccttcc   1320

gaaggactgt atctgatcta cagccaagta ctgttcaagg gtcaaggttg cccaagtaca   1380

catgttttgc tgacacatac tataagccgc atcgccgtgt cttaccaaac aaaagtgaat   1440

ctgctgtcag ctataaagag cccatgtcag agggaaacac ccgagggagc tgaggcaaag   1500

ccctggtacg aacccatata cttgggggc gtcttccaac tggagaaagg tgacaggctc   1560

agtgcagaga taaaccgccc cgactacctg aattttcgag agagcggtca agtatatttt   1620

ggtattattg cacttagtag tcggacccca tctgataaac ccgtcgctca cgtcgtcgca   1680

aacccacaag ctgaggggca gttgcagtgg cttaataggc gcgctaacgc tctgcttgct   1740
```

```
aatggcgtgg agttgaggga taatcaattg gtcgttccca gcgagggtct gtatttgatc   1800

tacagccagg tactttttaa gggccaaggc tgccctagta ctcatgtgct tctgactcat   1860

actatatcaa ggatcgccgt cagctaccaa accaaggtta atctccttag tgctatcaaa   1920

agcccatgtc aacgcgagac tcccgagggc gccgaagcca aaccctggta cgagcccata   1980

tacctgggtg gtgtgtttca gctggagaag ggggaccgac ttagtgcaga gattaataga   2040

cctgattacc tgaatttcag ggagagcggt caggtttatt ttgggatcat cgcactc      2097
```

<210> SEQ ID NO 123
<211> LENGTH: 2115
<212> TYPE: DNA
<213> ORGANISM: Artificial Sequence
<220> FEATURE:
<223> OTHER INFORMATION: Synthetic: Codon optimized nucleic acid sequence encoding SEQ ID NO 103

<400> SEQUENCE: 123

```
gagtcaaagt acggcccacc atgtcctcct tgtcctgccc ccgagtttct gggtggccca     60

tccgtcttcc tctttccacc taaaccaaaa gataccctca tgatctctcg gacacccgaa    120

gttacctgcg tcgtcgtcga cgtcagccaa gaagatcctg aagttcagtt caattggtac    180

gttgacggcg ttgaggtaca taacgccaaa acaaaacccc gggaggagca attcaattct    240

acttatcggg tggtttcagt tttgaccgtg ctgcatcagg actggctcaa cgggaaagaa    300

tacaaatgta aggtgtccaa caaaggactc ccttccagta tagagaagac tatatcaaag    360

gccaagggcc agccacgaga gcctcaggta tacaccctgc cccctagcca agaggagatg    420

actaaaaacc aagtaagtct gacatgcctt gtcaaggggt tctatcctag tgatattgcc    480

gtagagtggg agtctaacgg ccagcccgag aacaattata agacaacccc acccgtgctg    540

gattcagatg gatctttttt cttgtatagc cggcttacag tagataaatc tcgatggcaa    600

gaaggtaacg tgtttagttg ctccgtaatg cacgaggcac tccataatca ctatactcaa    660

aaatccctct ccttgtctct gggcaaaggg gggggcggct ccgtccgatc atctagtcgc    720

actccttcag acaagcctgt ggcccacgta gttgctaatc cacaggccga ggggcaactc    780

caatggctca accgcagagc caacgcattg ctggctaacg gcgtagaatt gcgagacaat    840

cagcttgtgg taccttccga gggactgtac ctcatctact ctcaagtttt gtttaaaggc    900

caaggttgcc ccagtactca cgtacttctc actcacacaa tcagccgcat cgctgtgtct    960

tatcaaacca aagtcaattt gctttccgcc ataaaaagcc cttgtcagcg agaaacccct   1020

gaaggagctg aagctaaacc atggtacgag cccatctatc tcggcggtgt tttccagctt   1080

gagaaggggg atcggctttc cgccgagatt aatcggcccg attacttgaa tttcagggag   1140

agcgggcagg tgtattttgg aataatcgct cttgtccggt cctcatctcg aacacctagt   1200

gataaacccg tagcccacgt agttgcaaat ccccaggccg aaggtcaact gcagtggctt   1260

aaccgccgag caaatgctct tctggcaaat ggggtagagt tgcgcgacaa tcaattggtc   1320

gtaccaagtg aaggcctcta ccttatctac tctcaggtcc tcttcaaagg tcaaggttgt   1380

ccttctactc acgtactcct gacacataca atatctcgca ttgcagtatc ataccaaaca   1440

aaggtgaatc ttctctccgc tataaaatca ccctgccaac gagagacacc tgaaggtgca   1500

gaggccaaac cctggtacga accaatttac cttggaggag tttttcaatt ggaaaaagga   1560

gatagactta gcgccgaaat aaataggccc gattacttga attttagaga gtccgggcag   1620

gtatatttcg gcataatagc actggtcagg agttccagca ggactcccag cgataagccc   1680
```

```
gtcgcacacg tggttgctaa tccacaagct gaaggacagc tgcaatggct taatagaagg   1740

gccaatgctc tgttggctaa cggcgttgaa cttcgggata accagcttgt ggtgccctcc   1800

gaaggtttgt atttgatcta ttcacaagtt ttgttcaaag gccagggttg cccctctacc   1860

cacgtacttc tgacacacac aatcagccgc atcgctgtct cataccagac caaagtcaac   1920

ttgttgtctg caataaaatc accatgtcag cgggaaactc ctgagggcgc cgaggccaaa   1980

ccctggtatg agccaatcta ccttggtggc gtatttcagc ttgaaaaagg agacaggctt   2040

tccgcagaga taaacaggcc agattatctg aactttaggg aatcaggtca agtctacttt   2100

ggaatcatag ctctc                                                    2115
```

```
<210> SEQ ID NO 124
<211> LENGTH: 2142
<212> TYPE: DNA
<213> ORGANISM: Artificial Sequence
<220> FEATURE:
<223> OTHER INFORMATION: Synthetic: Codon optimized nucleic acid
      sequence encoding SEQ ID NO 104

<400> SEQUENCE: 124
```

```
gaatccaagt atggcccacc atgtcccccc tgccccgccc ctgaatttct tggcggaccc     60

agcgtatttc tgttcccacc aaagcccaag gacacactta tgataagtcg gacacctgaa    120

gtaacttgtg tcgtcgtcga cgtgagtcag gaagaccctg aagtccaatt taactggtac    180

gtggatggcg tggaggtaca caatgccaag accaagccac gcgaagagca gttcaattca    240

acatatcggg tcgtttccgt cctgaccgta ctgcaccaag attggctcaa tgggaaggag    300

tacaaatgta aagtatctaa caaaggcctc ccatcctcca tagaaaaaac cataagtaaa    360

gctaagggac agcctcgaga acctcaggtc tacacactgc ccccatctca agaagaaatg    420

accaaaaacc aagtgagtct tacttgtctg gtgaaaggtt tctatccatc cgacattgcc    480

gtagagtggg aatcaaacgg ccaacctgag aataactaca aaactactcc tcccgtcctc    540

gatagtgacg gtagcttctt cctgtacagc aggctcacag tcgacaaatc caggtggcaa    600

gaaggcaatg ttttcagctg ttccgtcatg catgaagccc tgcacaacca ttatacacag    660

aaaagcttga gcctgtcctt gggtaaaggt ggaggggggga gtgggggtgg tgggtctgtg    720

cgaagcagta gcagaacacc ttccgacaaa ccagttgcac atgttgttgc taatcctcag    780

gccgaagggc agcttcagtg gctcaacagg agggctaacg ctttgttggc taacggtgta    840

gagctccgcg ataaccaact tgtagtgcct tccgagggac tctatcttat ttactcccaa    900

gtgctgttta aggacaaggg gtgccctagc acccacgtat tgctgactca cactatcagc    960

aggattgccg tcagctacca gactaaagtt aaccttctgt cagctataaa atcaccctgt   1020

cagcgggaaa ccccagaggg agcagaggca aaaccctggt acgaaccaat atacttgggc   1080

ggagtatttc aattggagaa aggtgataga ctgagcgctg aaataaatcg gcctgactat   1140

cttaacttcc gcgaatcagg gcaggtgtat ttcggcatca ttgccctcgg tggcggaggg   1200

agctcctcaa ggactccaag cgataagcca gtggctcacg tagtggccaa tccacaagca   1260

gaaggtcaac tgcaatggct taaccgccgc gcaaacgcat tgttggctaa cggtgtggaa   1320

ttgagagata accaattggt ggttccttca gaaggcctgt acctgatcta tagtcaagta   1380

ctgttcaaag gacagggttg tcccagcact catgttcttc tgacccacac tattagtaga   1440

atagccgtat catatcaaac caaagtcaac cttttgtctg ccataaaatc cccctgccaa   1500

agagaaacac ccgaaggagc cgaggccaaa ccttggtacg agccaatata cctgggggc    1560
```

```
gttttccaat tggaaaaggg cgataggttg agcgctgaga taaataggcc agattatttg   1620

aatttcaggg aaagcgggca agtgtacttc gggatcatag ccctgggcgg gggtgggtca   1680

agctctcgca ctccctcaga caagcccgtt gcacatgtgg tggctaatcc acaggctgag   1740

ggacagctgc agtggctgaa tagacgagca aatgcactgc ttgctaacgg agttgagctc   1800

cgcgataacc aactggtggt accctctgag ggactctatt tgatttactc ccaagttctc   1860

ttcaagggcc aaggctgccc ctccactcat gtcctgctta cccacactat ttctagaata   1920

gccgtatctt accagaccaa ggtcaacctc ttgagtgcaa taaagagtcc ctgtcaacga   1980

gaaactccag aaggcgccga agctaagcca tggtatgagc caatttacct cggggggagtg   2040

tttcagcttg agaaagggga cagactgagt gccgaaataa accggcccga ctatctcaac   2100

ttccgcgaga gtggtcaagt ctacttcggt atcatagctt tg                       2142
```

```
<210> SEQ ID NO 125
<211> LENGTH: 2112
<212> TYPE: DNA
<213> ORGANISM: Artificial Sequence
<220> FEATURE:
<223> OTHER INFORMATION: Synthetic: Codon optimized nucleic acid
      sequence encoding SEQ ID NO 105

<400> SEQUENCE: 125
```

```
gagagtaaat acggcccacc ttgtcctccc tgccctgctc cagagttcct tggcgggcct     60

tccgtcttcc tgtttccccc caagccaaag gacacactga tgatttcaag aaccccagag    120

gtcacctgtg tcgttgtaga tgttagtcaa gaggatccag aggtgcaatt caattggtat    180

gtcgatgggg tggaggttca caacgctaag accaaacctc gggaagagca attcaattct    240

acttatcggg tggtaagtgt tcttactgtt ttgcaccagg actggttgaa cgggaaggaa    300

tataagtgca aggttagtaa caaggggctt ccttccagca tcgaaaagac aattagcaaa    360

gccaagggac aaccccgaga gccacaagtg tataccctta ccccctccca agaggaaatg    420

accaagaacc aagtctctct gacctgcctg gtgaaagggt tctatccaag cgacatagct    480

gtcgaatggg aatccaacgg ccaacccgaa aataactata aaacaacacc tcccgtcctg    540

gattccgatg ggtcattttt cttgtattca agattgaccg tggataaaag ccgctggcag    600

gaggggaacg tttttttcatg tagtgtaatg catgaagctc ttcataacca ttatacacag    660

aaaagtttga gtttgtcact cggtaaaggt ggaggagggt ccggtggcgg tggctcagtg    720

agaagttctt ctaggacccc ttccgacaaa cccgttgccc acgttgtcgc aaatccacaa    780

gctgaagggc agcttcagtg gctcaatcgg agagcaaatg ctctccttgc caacggagtc    840

gaactgcgcg acaaccaact cgtcgttccc tccgagggcc tgtatctgat ctattcacaa    900

gtgttgttca aaggtcaagg ttgtccaagt acccatgtct tgctgacaca cacaatatca    960

agaatagcag tcagctatca aacaaaagtg aatttgctct ctgccatcaa aagtccctgc   1020

caacgcgaga ctcctgaagg tgctgaagca aaaccctggt atgaacctat atatttgggt   1080

ggcgtctttc aacttgaaaa gggtgacaga ctttctgccg agataaaccg gccagactat   1140

ctgaactttc gagagtccgg tcaggtttat ttcggtatca ttgccttgag ctctagaaca   1200

cctagcgaca aacctgtcgc ccatgtagtt gcaaatcccc aggctgaggg tcaactccaa   1260

tggcttaaca ggcgcgccaa cgctcttctc gccaacggtg tagagctgcg cgataatcaa   1320

ctggtggttc cttccgaggg actttatctg atatattcac aggttctgtt taaaggccag   1380

ggttgtccct ctacacatgt attgttgaca cacactatat ctcggatagc tgtgagctac   1440
```

```
caaacaaaag taaatttgct gtctgctatc aagagtccat gtcagaggga aacccccgaa   1500

ggagcagagg ccaaaccatg gtacgaacca atatatcttg gggagtctt tcaattggag   1560

aaaggggacc ggttgagtgc cgagattaac cgacctgatt accttaattt cagggagagc   1620

ggtcaagttt acttcggcat aatagccctt tcttcacgga caccttcaga caaaccagtg   1680

gctcatgtgg ttgcaaaccc tcaagcagaa ggtcaattgc aatggcttaa tcgcagagct   1740

aatgcccttt tggcaaacgg tgtggagctt cgggataatc agttggtggt tccaagtgaa   1800

ggtctgtact tgatatattc ccaagtgctg ttcaaagggc agggctgccc ctctactcat   1860

gttctgctca cccatacaat atctagaatc gctgtgagct accagactaa ggtcaatctt   1920

ttgtcagcaa taaaatcacc atgccaacgg gagactccag aaggagcaga agccaaaccc   1980

tggtatgaac ctatatacct cgggggcgtc tttcagcttg agaagggtga caggctgagc   2040

gctgaaatta atcggcccga ctaccttaac tttagagaat ccggtcaagt atatttcggt   2100

attattgccc tc                                                       2112
```

```
<210> SEQ ID NO 126
<211> LENGTH: 2130
<212> TYPE: DNA
<213> ORGANISM: Artificial Sequence
<220> FEATURE:
<223> OTHER INFORMATION: Synthetic: Codon optimized nucleic acid
      sequence encoding SEQ ID NO 106

<400> SEQUENCE: 126

gagagcaaat atggcccacc ctgcccccca tgtcctgccc cagaattcct gggaggaccc     60

tcagtgtttc tctttccacc caagccaaaa gacacattga tgatttcaag gactcctgag    120

gtgacatgtg ttgtagtaga cgtatcacag gaggatcctg aagtccagtt caactggtac    180

gtcgacggcg ttgaagtgca caatgctaaa accaagcccc gagaggagca gtttaacagc    240

acatatcggg tcgtttctgt gcttaccgtc ttgcatcagg attggctgaa cggaaaagaa    300

tataaatgca aggtctcaaa caaggggctt ccatcttcaa tagaaaaaac aatttcaaag    360

gcaaaaggac agcctagaga gccccaagtc tacactctgc cacccagcca ggaggagatg    420

acaaagaacc aggtcagcct gacctgtctc gtcaaaggat tctatccatc cgacatcgcc    480

gtagaatggg agagtaatgg acagcctgaa aacaactata agaccactcc cccagtactg    540

gacagtgatg ggtcattctt tttgtatagt cgactgactg tagataaaag tcgatggcag    600

gaaggtaatg tgttctcatg cagcgtcatg cacgaggccc tgcacaacca ttatacacag    660

aagagtctga gtcttagctt gggtaaggga ggcgggggat ccggaggcgg tggatctgta    720

cggtcttcta gcagaacacc aagtgataaa ccagtggctc acgtggtagc aaacccccaa    780

gctgaggggc agcttcaatg gcttaataga agggctaacg ctcttcttgc caacggggtc    840

gagcttaggg ataaccagct ggtggtcccc tctgaaggct tgtatctgat atactcccag    900

gtactgttta aggacaaggg ctgtcccagc actcatgtac tgttgacaca tactatatca    960

cgcatagctg tctcttatca gacaaaagtt aacttgctta gcgctatcaa gagtccctgt   1020

cagagagaaa cccccgaagg tgcagaggcc aagccatggt acgaacctat ttaccttgga   1080

ggcgttttcc aactggagaa aggggatcgc ctctccgccg aaataaacag gcccgattat   1140

ctgaacttcc gagagagcgg ccaagtctac tttgggataa tcgctctcgt gcggagcagt   1200

agcagaaccc cctctgataa accagttgcc catgtggttg ccaacccaca ggccgaaggt   1260

cagctgcagt ggctgaatcg gagagccaac gctcttctcg ccaatggtgt ggaactcagg   1320
```

```
gataaccaac tggttgtccc atctgaaggt ctttatctta tctattcaca agtgctcttt   1380

aagggacagg gctgtccaag tacacacgtc ttgctcactc acacaatatc cagaattgct   1440

gtaagctacc agacaaaagt aaacctcctt agcgccatta aaagcccttg tcaaagggaa   1500

acacctgagg gagccgaagc caaaccatgg tacgaaccca tatatctcgg tggcgttttc   1560

cagttggaga agggcgatcg actgtccgcc gagattaatc gccctgatta tctgaacttt   1620

cgggagtccg ggcaggttta ctttggtata atcgcactgg tacgctcaag cagtagaact   1680

ccctcagaca aaccagtagc acatgttgta gctaatccac aagcagaagg acagctgcaa   1740

tggctgaacc ggagagctaa cgccctgctg gctaacggtg tcgagttgcg agataatcag   1800

cttgtcgtgc ctagcgaggg gctctacctt atttatagtc aagttctctt taaagggcag   1860

gggtgtccaa gtacacacgt gttgctcaca catactattt ctcgaatagc cgtgtcctat   1920

caaaccaagg tgaaccttct ctccgctatc aaaagccctt gccaaagaga aacacccgaa   1980

ggcgccgagg ctaagccatg gtacgaacct atctatctcg gggtgtttt tcaactcgaa   2040

aaaggggaca ggttgagtgc tgagattaat agacccgatt atttgaattt tagggaatct   2100

gggcaggttt attttggaat aattgctctc                                   2130
```

```
<210> SEQ ID NO 127
<211> LENGTH: 2127
<212> TYPE: DNA
<213> ORGANISM: Artificial Sequence
<220> FEATURE:
<223> OTHER INFORMATION: Synthetic: Codon optimized nucleic acid
      sequence encoding SEQ ID NO 107

<400> SEQUENCE: 127
```

```
gtacggagca gctctagaac tccatctgac aagccagtcg ctcatgtggt agcaaatccc     60

caagctgagg gccaacttca gtggttgaat cgcagggcta acgctctgct cgccaatgga    120

gtagaattga gggataatca gctcgtagta cctagcgaag ggctttacct catatattct    180

caggttctgt ttaagggtca aggctgtcca agtactcacg ttctccttac tcatacaatc    240

tctcgcatcg cagtttctta tcaaaccaag gttaatttgc tgagcgccat taagtcacca    300

tgccagcgcg aaaccccga aggtgccgaa gcaaaacctt ggtatgagcc catttacctt    360

ggcggtgtgt ttcagctgga gaagggggac aggctttcag cagaaattaa taggcccgac    420

tatcttaatt tccgggagtc cggccaggtt tatttcggta tcattgccct gggcggtggc    480

ggctcatcct cacgcactcc atctgataag cccgtcgcac atgtggtcgc caatcctcag    540

gcagaggggc aattgcaatg gcttaaccgc agggcaaacg ctctgcttgc taatggggtt    600

gagcttcggg ataaccagct cgtggtacct tcagagggtt tgtacttgat ctattctcaa    660

gtgcttttca aggacaaggg ttgcccaagc acccatgtgt tgttgaccca tactatttcc    720

cggatagcag tgtcatatca aactaaggtc aatcttctgt cagctattaa aagtccctgt    780

cagagagaga ctccagaggg agctgaagcc aaaccctggt acgagcccat atatcttgga    840

ggggtgttcc agctcgagaa aggcgacaga ttgagcgccg agataaaccg gcctgactat    900

ctcaattttc gagagtccgg tcaggtttac tttgggataa tcgcactggg tggtggaggg    960

tctagctctc gcacaccatc cgataagcca gtagctcatg tggtggccaa ccctcaagcc   1020

gaggggcaac ttcagtggct gaatagacga gctaatgcat tgctggctaa cggtgtcgaa   1080

ctgagagata atcagctcgt agtaccttca gaagggcttt acctcatata ctctcaggtt   1140

ttgttcaaag gacagggatg tccttcaact cacgtccttc tcactcacac tataagtaga   1200
```

```
atcgctgtat cctaccaaac taaagtgaac cttttgtctg ctatcaaatc cccttgccaa   1260

cgcgaaactc ccgaaggcgc agaagccaag ccttggtatg agccaatcta cctcggagga   1320

gtttttcagt tggaaaaggg tgacaggctg agtgctgaaa tcaacaggcc cgattatctg   1380

aacttcaggg aaagcggaca agtgtatttt ggaataatcg cacttggtgg gggagggtcc   1440

gagtctaagt acgggccacc ttgtcctccc tgtccagcac ctgagttttt gggcgggccc   1500

agtgtattcc tgtttccacc caaacctaag gataccctga tgatatcacg aacccctgag   1560

gtcacctgtg ttgtcgttga cgtaagtcag gaggacccag aggttcagtt caactggtat   1620

gtcgacgggg tagaagttca taatgctaag actaagccaa gggaggaaca atttaattcc   1680

acttatcgag ttgtgagcgt cctgacagtt ttgcatcagg attggcttaa cggcaaagaa   1740

tataagtgca aggtttcaaa taaaggtctg ccttcttcca tagaaaaaac aatctctaaa   1800

gccaaaggcc aaccaagaga gcctcaggtg tacactcttc ctccctctca ggaagagatg   1860

acaaaaaacc aggtgtcctt gacctgtctc gttaaggggt tctatccaag cgatattgct   1920

gttgagtggg aatcaaacgg gcagcctgag aataattaca agaccacacc cccagttttg   1980

gatagcgatg gtagtttctt cctttacagt aggttgaccg ttgataagtc ccggtggcaa   2040

gaaggaaatg tgtttagttg ctccgtgatg cacgaggcac tgcataatca ttacactcaa   2100

aagagtctta gtctgagctt ggggaaa                                       2127
```

<210> SEQ ID NO 128
<211> LENGTH: 2097
<212> TYPE: DNA
<213> ORGANISM: Artificial Sequence
<220> FEATURE:
<223> OTHER INFORMATION: Synthetic: Codon optimized nucleic acid sequence encoding SEQ ID NO 108

<400> SEQUENCE: 128

```
gtgcggagta gcagcagaac tccatccgat aaaccagtgg cacacgtggt cgctaatccc     60

caagcagaag ggcagctcca atggctgaac aggcgggcca atgccctttt ggctaatggc    120

gtcgagctca gagacaatca gctcgtcgtc ccatctgagg gtctctactt gatctatagt    180

caggtcttgt tcaaaggcca aggctgtcct agtactcatg ttctccttac acataccatt    240

tcaaggatag cagtctcata tcagactaaa gtcaatctcc tgagtgcaat taagtccccc    300

tgccagcgag agactccaga aggtgctgag gcaaagccat ggtatgagcc catatatctt    360

ggcggagtct ttcaactgga gaagggtgac cggctctccg cagagattaa ccggcctgac    420

tatctgaatt tcagagagtc tggccaggtt tactttggca ttatcgcact ttccagtcgg    480

acccccagcg acaaacctgt tgcccatgtc gtagcaaatc cccaagccga aggccagttg    540

cagtggctga acagacgagc taatgctttg ttggcaaatg ggtggagct tcgggacaat    600

caactcgtgg taccatctga agggttgtac ctgatatata gccaggtact ctttaagggt    660

caaggttgtc ctagtactca tgtgctcttg acccacacaa tttcaagaat cgccgtcagt    720

taccaaacca aggttaatct gctttctgcc ataaagtctc cctgccaacg cgaaacccca    780

gaaggtgctg aagccaagcc ttggtacgag ccaatctacc tcggtggcgt tttcaactt    840

gaaaaggggg atcgcctgtc tgccgagatc aacaggccag actacctgaa cttccgagaa    900

agtgggcaag tctattttgg gatcatagcc ctgagctctc ggacccccag cgacaagcct    960

gttgcccacg tagttgctaa ccctcaggct gaaggacaac ttcagtggct gaacaggaga   1020

gctaacgccc tcctggctaa tggagtcgaa ctgagagata atcaattggt cgtaccaagc   1080
```

```
gagggactgt acctcatata ctctcaggta ctgtttaagg gccaaggatg tccaagtacc   1140

catgtacttc tcacacatac aataagccgg atagccgtca gctatcagac taaggtaaac   1200

ctgctcagcg ctattaagag cccatgccag cgagagaccc cagaaggagc agaagctaaa   1260

ccctggtacg agccaatata tcttggagga gtctttcaac tggagaaggg tgaccgattg   1320

agtgctgaaa ttaatcggcc agattatttg aacttccgcg agagcgggca agtgtatttc   1380

ggaatcattg cacttggcgg gggcgggagc gagtccaaat atggcccacc atgtcccccc   1440

tgccctgccc cagagttcct tggggggccct tctgtatttc tcttcccccc aaaacccaag   1500

gatactctta tgatcagcag gactcctgag gtaacctgtg tggtcgtcga cgtatcacaa   1560

gaggatccag aggtacagtt taattggtat gtagacggcg tggaagtcca caatgctaaa   1620

actaagccca gagaggagca gtttaatagt acataccgag tagtgagcgt attgactgta   1680

ttgcatcagg actggttgaa tgggaaagag tacaagtgca aagtttccaa caaaggtctc   1740

ccttcatcta tcgagaaaac catctcaaag gccaaaggcc aacccagaga gcctcaagta   1800

tacactctgc cacccagcca agaagagatg actaagaatc aggttagtct cacttgtctc   1860

gtcaaagggt tctatccctc cgatattgct gtggaatggg agagcaacgg gcaacccgag   1920

aacaactata agacaacccc accagtactt gatagcgacg ggtctttttt cctttattca   1980

cgccttacag ttgataaatc tcggtggcag gaagggaacg ttttcagctg ttctgttatg   2040

catgaagcct tgcataacca ttacacacaa aagagtctta gtttgtctct tggaaag      2097
```

<210> SEQ ID NO 129
<211> LENGTH: 2115
<212> TYPE: DNA
<213> ORGANISM: Artificial Sequence
<220> FEATURE:
<223> OTHER INFORMATION: Synthetic: Codon optimized nucleic acid sequence encoding SEQ ID NO 109

<400> SEQUENCE: 129

```
gtgcgcagca gttccagaac acctagtgac aagcctgtgg cacacgttgt ggccaatcct     60

caagctgaag gtcagctcca atggcttaat agaagggcta acgcattgct tgctaatggg    120

gtggaacttc gagataacca attggtggtg ccctccgagg gtctctacct tatctatagc    180

caggtcctct ttaaaggcca aggttgcccc agtacacacg tcctgcttac acacacaata    240

tccagaatag cagtctcata ccagaccaag gtaaatctgc ttagcgctat taagtcaccc    300

tgtcagcggg aaaccccaga gggtgcagaa gcaaaaccat ggtatgagcc aatttacctt    360

ggtggcgttt ttcaactgga aaagggcgat aggttgagcg ccgagatcaa tagacccgac    420

tatctcaatt ttcgggagtc aggccaggtt tatttcggga tcattgcttt ggttcgctcc    480

tctagccgca ccccttccga taaaccagtt gcacatgttg tggccaatcc ccaggctgaa    540

ggccagcttc agtggctcaa cagacgggct aatgccctcc tcgccaatgg ggtcgagctg    600

agggacaacc aacttgtggt cccctcagaa ggtctctacc ttatctacag ccaggttctt    660

ttcaaaggcc agggctgtcc ttccactcac gtgctgttga cccataccat atcccgcatt    720

gccgttagct atcaaaccaa agtcaacctt ttgtctgcaa ttaagagtcc atgccagaga    780

gaaactcccg aaggtgcaga agcaaagcca tggtatgaac ctatatatct cggaggtgtg    840

tttcaacttg agaaagggga cagactgagt gccgaaataa atcgccctga ttatcttaat    900

ttccgagagt ctgggcaagt atattttgga attattgccc tcgtgcgaag ctcttcaagg    960

accccaagtg ataaacccgt agcacacgta gttgcaaatc cacaagccga aggacagttg   1020
```

```
caatggctga ataggcgggc taatgctttg cttgctaatg gggtcgagct gcgggataac   1080

cagcttgtcg tgccatctga aggattgtac ctgatataca gccaagtttt gtttaaggga   1140

cagggatgcc catcaaccca cgtgctcctc actcacacta tttctcgaat tgccgtatca   1200

tatcagacta aagtcaactt gttgagcgca ataaagagcc cttgtcaacg ggaaaccccc   1260

gagggtgcag aggccaaacc atggtatgaa cctatttacc tcgggggcgt ctttcagttg   1320

gaaaaaggtg atcggttgtc cgctgagatt aaccgaccag actatcttaa ctttcgggaa   1380

tctggtcaag tctattttgg cataattgca ttggggggcg gggctctga atccaaatac   1440

gggcctcctt gcccccttg cccagcacca gaatttctcg gggggcccatc agtttttctt   1500

ttccccccta agccaaaaga taccctcatg atatcaagaa ctccagaggt tacatgtgtc   1560

gtggtcgacg ttagccagga ggatcccgag gttcagttca attggtacgt ggatggagtt   1620

gaagtgcaca atgccaaaac aaaaccacga gaagagcaat ttaatagcac ctacagggta   1680

gtcagcgttc ttacagtttt gcaccaagat tggcttaacg gcaaagaata caaatgtaag   1740

gttagtaata aaggactccc ctcatcaata gaaaaaacaa tttccaaagc taaaggccag   1800

cctagggaac ctcaagtgta cacacttcct ccaagtcaag aagagatgac aaagaaccag   1860

gtctcactca cttgtctcgt caaaggtttc taccctctg acatcgccgt ggaatgggag   1920

tccaatggcc aacctgagaa taattacaag accacacctc cagtactcga tagtgacggg   1980

tctttctttt tgtattctag gttgacagtg gataaatcca gatggcaaga aggaaatgtt   2040

ttctcatgtt ctgtgatgca cgaggctctt cacaaccact acactcaaaa gtctctgtct   2100

ctttcccttg gcaaa                                                    2115
```

<210> SEQ ID NO 130
<211> LENGTH: 2112
<212> TYPE: DNA
<213> ORGANISM: Artificial Sequence
<220> FEATURE:
<223> OTHER INFORMATION: Synthetic: Codon optimized nucleic acid sequence encoding SEQ ID NO 110

<400> SEQUENCE: 130

```
gtccgatcat ctagtaggac ccctagcgac aagccagttg cacacgtggt agcaaaccca     60

caagcagaag gacaactgca gtggcttaat aggcgcgcaa atgcattgct cgccaatgga    120

gtggaactcc gagacaacca attggtagtg ccttccgaag gactctacct tatttatagt    180

caggtcctgt tcaaagggca aggttgcccc tcaacacacg tattgctgac acacaccata    240

tcccgcatag cagttagcta tcaaacaaag gttaatttgc tgtccgcaat aaagagcccc    300

tgccaacggg agacccccga gggcgcagag gcaaaaccct ggtacgagcc catctacttg    360

ggtggcgtct ttcaacttga aaagggggat aggctgagcg ctgaaattaa ccggcccgac    420

tatttgaatt tccgggaatc tggccaagta tactttggta ttattgcctt gggtggtgga    480

ggtagcagta gccgaacacc atcagacaaa cctgtggcac acgttgtcgc caacccacaa    540

gctgaaggac aactccaatg gttgaacagg cgagccaatg ccctccttgc aaatggcgta    600

gaattgcgag ataatcagct tgttgttcct agcgagggtc tttatcttat atacagtcag    660

gtcctcttta aaggccaagg atgtcctagt acacacgtgc tgctgactca tacaataagc    720

cgaattgccg tatcctatca gactaaggtc aaccttctga gcgctattaa atccccatgt    780

caaagggaaa ctccagaagg cgcagaagcc aagccctggt atgagccaat ctatctcgga    840

ggggttttcc aattggagaa gggcgaccgg ctttctgctg aaatcaatcg acctgattat    900
```

```
ctcaactttc gagagtcagg gcaggtttat ttcggtatca ttgctctcgg tggcggaggg     960
tccagctcta ggaccccctc agacaaacca gtagcccacg ttgtggccaa tccccaggca    1020
gaaggtcagt tgcagtggtt gaatcggcgc gctaatgcac tcctcgccaa tggagttgaa    1080
cttagggata atcaactcgt agtccccagc gaagggttgt atcttattta tagtcaggtc    1140
ctttttaagg gtcagggttg cccatccact cacgtgttgc tcactcacac catcagtcgc    1200
atcgccgttt cctatcagac caaggttaat ctcctgtccg ctataaagtc cccatgtcaa    1260
agagagaccc ccgaaggagc agaggcaaag ccttggtacg agcctatata cttgggtggc    1320
gtatttcagt tggaaaaggg tgaccggttg tccgctgaga taaatcgacc tgactatctc    1380
aactttcggg agtctggtca ggtttacttt gggattatag cactggagag caaatacgga    1440
ccccccctgtc ctccttgtcc tgccccagag tttctcggtg gaccatcagt ctttcttttt    1500
cctcctaagc ccaaggatac attgatgatc tcacggaccc ccgaagttac ctgcgtggtt    1560
gttgatgtaa gtcaggagga tcccgaagtc caattcaatt ggtatgtcga cggcgtggag    1620
gtccacaatg caaagacaaa gccccgggag gaacagttta acagcacata ccgggtcgtt    1680
agcgtgttga ccgtccttca tcaagattgg ttgaacggca aagagtacaa gtgcaaggtt    1740
agcaacaaag gtttgccatc ttccatcgag aaaacaatat ctaaggccaa aggacagccc    1800
cgcgaaccac aagtttatac tcttcctcca agccaggagg aaatgactaa gaatcaggtt    1860
tccctcacat gccttgtaaa gggtttttat ccctcagata ttgcagttga gtgggagagc    1920
aatggtcagc ccgagaataa ctataaaaca accccaccag tactcgactc agatggtagt    1980
ttcttcctct actccaggtt gacagtagac aaaagccgct ggcaagaggg caacgtattc    2040
tcttgctcag tgatgcatga agcactgcat aatcactaca cacaaaaatc tctgagcctt    2100
tcacttggca aa                                                        2112
```

<210> SEQ ID NO 131
<211> LENGTH: 2082
<212> TYPE: DNA
<213> ORGANISM: Artificial Sequence
<220> FEATURE:
<223> OTHER INFORMATION: Synthetic: Codon optimized nucleic acid sequence encoding SEQ ID NO 111

<400> SEQUENCE: 131

```
gttaggtctt catctagaac acccagcgac aagcccgtgg cccacgtcgt tgccaacccc      60
caggcagagg gtcagctgca gtggctcaat aggcgagcta acgcccttct cgctaacggt     120
gtggagttgc gcgataacca actggtcgta ccatccgaag gactctatct gatttattct     180
caagtcctgt ttaagggcca gggctgtcct tcaacccacg tcctccttac acataccatt     240
tctagaatag ccgtatcata tcagactaaa gtaaatcttt tgtcagcaat caaatctcca     300
tgccaacggg agaccccaga gggagcagaa gctaaaccct ggtacgaacc catatatctg     360
ggcggtgtct tccagcttga gaagggggac cgactctcag ccgagataaa tcgacctgac     420
tatttgaact tcagagagtc cgggcaagtc tatttcggaa ttatagctct ctcctctagg     480
accccatcag ataaaccagt tgcccatgtc gtggctaatc cccaggctga aggccaactg     540
caatggctta accgccgggc caatgctttg ctcgccaacg gtgtagagtt gcgcgacaac     600
caactggtag tccctagcga agggctgtac ctgatctact cccaagttct ttttaaaggc     660
caaggttgtc ctagtaccca cgtacttctg acccatacta tatctcggat agctgtgagt     720
taccagacaa aggttaacct tctttccgcc atcaaaagtc cttgccaaag ggaaacacct     780
```

```
gaaggtgcag aagccaagcc ctggtatgag ccaatttatc tgggcggagt cttccaactc    840

gagaaggggg atagactgag cgctgagata aacagaccag actatctgaa ttttagggag    900

tcaggccagg tatactttgg aataatcgcc ctctcatcaa ggactccctc cgacaaacca    960

gtagcacacg tagtggcaaa tccccaggca gaaggacagc tccagtggct gaatcggcgg   1020

gcaaacgccc tgctcgctaa cggggtcgaa cttagggaca accagcttgt tgtgccatcc   1080

gaaggtttgt acctgatata ttctcaagtt ctctttaaag gccaggggtg tccttctact   1140

catgtgctgt tgactcatac aatatcacgg attgcagttt cctatcaaac taaagtaaac   1200

ttgctttcag ctatcaagag tccatgccaa agggagacac ctgaaggggc agaggctaaa   1260

ccctggtacg agcctattta cctcgggggc gtttttcagc tggaaaaagg agatcggttg   1320

tcagctgaaa tcaacagacc cgactatctg aactttcgcg agtcaggtca ggtttatttt   1380

ggcattattg ccctggaaag caagtacggt cctccttgtc caccatgccc tgctccagaa   1440

ttcttggggg gaccatcagt gtttctgttc ccccccaaac caaaggacac cttgatgata   1500

agccgaaccc cagaagtgac ctgtgtcgta gttgatgtaa gtcaagaaga tccagaggtc   1560

caattcaact ggtacgttga cggtgtcgag gtacataacg ccaaaaccaa gcctcgcgaa   1620

gagcagttta actccacata tagggtggta agtgtgctca cagtgctgca tcaagactgg   1680

cttaacggga aggaatacaa gtgtaaagtc tccaataagg gacttccctc tagcatagaa   1740

aaaactatat ctaaagcaaa gggtcaacca cgcgaaccac aggtatatac actcccccct   1800

agccaggagg aaatgaccaa aaaccaagta tctttgacct gtctggtgaa aggcttttac   1860

ccatctgata tcgcagttga atgggagtca aatggccaac ccgaaaataa ctacaagaca   1920

actcctcccg tgctcgactc tgacggatca ttcttccttt actctcgcct caccgtagat   1980

aagagccgct ggcaagaggg taacgtattc agttgtagcg tgatgcatga ggctcttcat   2040

aaccattata cacaaaagtc cctcagcctt tctctgggaa ag                      2082
```

<210> SEQ ID NO 132
<211> LENGTH: 2094
<212> TYPE: DNA
<213> ORGANISM: Artificial Sequence
<220> FEATURE:
<223> OTHER INFORMATION: Synthetic: Codon optimized nucleic acid sequence encoding SEQ ID NO 112

<400> SEQUENCE: 132

```
gtccgctcat catcaagaac cccaagcgac aaacctgtgg cccacgttgt tgccaatcca     60

caagccgagg ggcagctgca gtggcttaac aggagagcaa acgctcttct tgccaacggc    120

gtagagcttc gagacaacca acttgtcgta ccttctgaag gtctgtacct catctatagt    180

caagtacttt ttaaaggaca gggttgtcca agtacacatg tacttctgac ccacacaata    240

tccaggatag ccgtgtcata ccagacaaag gtcaatctgt tgtctgcaat taagtcacca    300

tgccaaagag aaaccccaga aggtgcagaa gcaaagccat ggtatgagcc aatatatctg    360

ggcggcgtct ttcagctcga gaagggagac cggctgtctg cagaaatcaa caggcctgac    420

tacctcaact tcagggagag tggccaggtg tattttggaa taattgcatt ggttagaagt    480

tctcgcacac catccgataa accagtcgcc cacgttgtag ctaatccaca agccgaggga    540

cagctgcaat ggctgaatcg acgggccaat gcattgctgg ctaatggggt agagcttcgc    600

gataatcaac ttgtggtccc atcagagggt ctttacctca tatactccca agtccttttc    660

aaaggccaag gttgtccttc tacacatgtg cttttgaccc acactatttc tagaatcgca    720
```

-continued

```
gtgtcatacc agactaaggt caacctgctc tcagctatta agtcaccctg ccaaagggaa    780

actcccgagg gtgccgaggc caaaccttgg tatgaaccta tctaccttgg gggagtgttc    840

caactggaga agggcgatag attgagtgcc gagataaatc ggccagatta tttgaacttc    900

agagagagcg gacaagtcta cttcggtata atagcattgg tgcgcagtag ccgaactccc    960

tccgataagc cagtcgccca tgttgtcgca aaccctcagg cagagggaca gcttcaatgg   1020

ctcaatcgcc gcgccaatgc cttgcttgcc aacggtgttg aactgaggga caaccagttg   1080

gtcgttccta gcgaaggttt gtatcttatc tatagccagg tactgttcaa agggcaaggg   1140

tgtcctagta cccatgtgct cctcacacat accatatcaa gaattgcagt tagttatcag   1200

accaaggtaa atctcctgag tgcaataaaa tccccctgcc agcgggagac tccagagggg   1260

gctgaggcca aaccatggta cgagcccatc tatctcggtg gagtctttca gctggaaaag   1320

ggagatcgcc tttctgcaga gattaatagg ccagattacc tgaatttccg cgagagtggg   1380

caagtttact tcggtatcat agcccttgaa agcaaatacg gccctccatg cccccccctgc   1440

cctgcacccg agttcctggg cggtccctct gtgttcttgt tccccccaaa gcccaaggac   1500

accctcatga tatccaggac accagaagta acttgcgttg tcgtcgatgt gtcccaggaa   1560

gatccagaag ttcaatttaa ctggtatgtc gatggtgtgg aagtgcataa tgcaaaaact   1620

aagcctcgag aagaacaatt caactctaca tatcgcgtcg tcagtgtgtt gactgtcctc   1680

caccaagact ggctgaatgg caaagagtac aagtgcaaag tgtccaataa gggccttcca   1740

tcttcaattg agaaaaccat tagtaaggca aagggtcagc cccgggaacc acaggtctat   1800

acattgcccc ctagccaaga ggagatgacc aagaaccaag tctcactcac ctgtctggta   1860

aagggatttt accctagtga tatcgctgtc gaatgggaaa gcaacggtca gcccgagaac   1920

aattacaaaa ccactccacc agtgctcgac tcagacggct ctttttttcct ttactcacgg   1980

ttgactgtag ataaatcccg ctggcaggag ggcaatgttt tcagctgtag tgttatgcac   2040

gaagcacttc acaatcatta tacccagaag tcactgtctc tttcccttgg gaag           2094
```

<210> SEQ ID NO 133
<211> LENGTH: 2136
<212> TYPE: DNA
<213> ORGANISM: Artificial Sequence
<220> FEATURE:
<223> OTHER INFORMATION: Synthetic: Codon optimized nucleic acid sequence encoding SEQ ID NO 113

<400> SEQUENCE: 133

```
gagccaaagt ccagcgacaa gacacatact tgtccaccct gtccagctcc agaggcagcc     60

ggcggtcctt ccgtgttctt gtttcctccc aagccaaagg acacactgat gatctctaga    120

actcccgagg ttacatgcgt tgtggttgac gtgtctcatg aggaccctga agtgaagttt    180

aattggtacg tcgacggtgt cgaggtacat aatgcaaaaa ctaagccacg cgaggaacaa    240

tataatagca cataccgagt ggtcagcgtc ttgacagtgc ttcaccaaga ctggctcaat    300

ggtaaggagt ataaatgcaa agtatcaaac aaagccttgc ccgcatccat cgaaaaaaca    360

ataagcaagg ctaagggaca accacgggag ccacaagtgt atactctccc cccttcaaga    420

gacgagctca caaaaaacca agtttcactg acttgcctgg ttaaaggttt ttatccctcc    480

gatatagctg ttgaatggga gagtaatgga caaccagaaa ataactataa aactactcct    540

cccgtgcttg acagtgacgg gtcttttttc ttgtattcta aactcaccgt tgataaaagt    600

agatggcagc agggcaatgt tttctcctgc tcagtgatgc atgaagctct gcacaatcac    660
```

```
tacacacaaa aatcactgtc cctgtctcct ggtaagggtg gcggtggcag cgtcaggtca    720
agttccagaa cacctagtga taaaccagta gcccatgtag ttgctaaccc ccaggctgag    780
ggacaacttc agtggcttaa ccgccgcgct aatgctcttc ttgctaacgg agtcgaactg    840
agagataacc aacttgtcgt gcctagtgag ggttgtatc tcatttactc tcaggtgctg     900
ttcaagggcc agggctgtcc atcaactcac gtactgctta cacatactat tagcaggata    960
gcagtgagct accaaaccaa agttaacttg ttgtctgcca ttaaaagccc ttgtcagagg   1020
gaaacccctg agggggcaga agctaagcca tggtacgaac ctatttacct tggtggggtg   1080
tttcagttgg agaaagggga tcggcttagt gctgaaataa atagacccga ttatttgaac   1140
ttccgggaga gtggtcaggt ttacttcgga atcatcgccc tgggaggggg gggttctagc   1200
tcaaggacac caagcgataa accagtggca catgtggtcg ctaatcccca agcagagggg   1260
caacttcagt ggttgaaccg ccgggctaat gcactgctcg caaacggtgt agagttgagg   1320
gacaatcaac tcgttgtacc aagtgagggc ttgtatctca tatacagcca ggtgcttttt   1380
aaaggccagg ggtgtcccag tacacacgtg ttgctcaccc acacaatatc aagaatagca   1440
gtctcatacc aaactaaggt taatctcctc tcagcaatta aatccccttg tcagcgggag   1500
acccccgaag gcgctgaggc taagccctgg tacgaaccca tctatcttgg tggggttttt   1560
caactggaga aaggcgatcg attgtcagcc gagattaatc gcccagatta cctgaacttt   1620
cgcgaatccg gacaggtata cttcggcatt atcgcattgg gtggcggtgg cagcagcagt   1680
aggactccta gcgataaacc cgttgctcat gttgttgcaa acccacaggc agaagggcag   1740
ctccaatggc tcaatcggcg cgcaaacgca ttgctggcca acggagtaga gctgcgggac   1800
aaccaacttg ttgttcccag cgaaggtctt tacctcattt attcccaagt ccttttcaag   1860
ggccaaggct gtccaagtac acacgtactt cttactcaca caataagtcg catagcagtc   1920
tcttaccaaa caaaagtcaa tctcctgtct gcaattaaat ccccatgtca aagagaaacc   1980
ccagaagggg cagaggccaa gccttggtat gagcctatct atttgggcgg ggtttttccaa  2040
cttgagaagg gagaccggct ttcagctgaa atcaacaggc ccgattatct caacttcagg   2100
gagagtggac aagtctactt cggaattata gccctg                             2136
```

<210> SEQ ID NO 134
<211> LENGTH: 2124
<212> TYPE: DNA
<213> ORGANISM: Artificial Sequence
<220> FEATURE:
<223> OTHER INFORMATION: Synthetic: Codon optimized nucleic acid sequence encoding SEQ ID NO 114

<400> SEQUENCE: 134

```
gaaaggaagt caagcgtgga atgccctccc tgtccagcac cacccgtcgc tggacccagc     60
gtgttcctgt tcccacccaa acccaaggat actctcatga tcagccggac accagaggta    120
acttgtgtag tagtagatgt tagccatgag gatcctgagg tgcagtttaa ttggtacgtt    180
gacggggtgg aggtacataa cgcaaaaacc aaaccacgag aggagcagtt caacagcacc    240
tttcgcgtag tgtcagtcct gaccgtagtc caccaggact ggttgaacgg taaggaatac    300
aagtgtaagg tttccaacaa gggtctgcct gcctctatcg agaaaacaat aagcaagaca    360
aaaggccaac ctcgggaacc tcaggtatat acacttcccc caagtcgaga ggagatgact    420
aagaaccagg taagccttac ttgcctggta aaaggttttt atcccagcga catcgccgtc    480
gaatgggaat ccaatggaca gcctgagaat aactataaga caaccccccc tatgctggat    540
```

```
tcagacggta gcttctttct ttattccaaa cttaccgtgg ataaatcaag gtggcagcaa    600
gggaatgttt tctcttgtag tgtcatgcac gaagcccttc acaaccatta cactcagaaa    660
tccctcagct tgtcacctgg aaaagggggc ggcggaagtg tccgatcctc ctctcggacc    720
ccatctgaca agccagttgc ccatgtggtg gctaatccac aggctgaggg gcaactccag    780
tggctgaata ggagagctaa tgctctcctt gctaatggag ttgaacttag agacaatcag    840
cttgtcgtcc cctctgaagg gctctatttg atatacagcc aggttctttt taagggtcag    900
ggctgtccct ccactcatgt gcttctcaca cacacaatca gccgcatcgc agtgagttat    960
caaaccaaag ttaacctgct ttccgcaatc aaaagccctt gtcagagaga aaccccagaa   1020
ggagcagaag ccaaaccctg gtatgagccc atctatctcg gaggagtatt ccaactggaa   1080
aagggtgata ggttgagcgc tgagataaat agacccgact atctgaactt cagggagagt   1140
ggtcaagtat actttggcat tattgccctc ggcggcggcg gcagttccag tcggacaccc   1200
tcagataagc cagttgctca cgttgtggcc aacccccaag ccgaaggcca gttgcagtgg   1260
ttgaataggc gggctaatgc tctgctggca aacggtgtag aacttcgaga taatcaactc   1320
gttgtgccct cagagggact ctatctcatt tacagccagg tgcttttcaa agggcagggg   1380
tgtccctcta cacatgtcct tctgacacat acaatctcac gaatagctgt ctcctaccaa   1440
acaaaagtta atttgctcag tgctataaaa tccccttgcc agcgggagac acctgagggg   1500
gctgaggcca aaccttggta cgagcctatc tatctcggcg ggtattccaa acttgaaaaa   1560
ggggacagac ttagtgccga aataaaccgc ccagactacc ttaacttccg cgagtccggg   1620
caggtttact ttgggataat cgcactgggg ggaggtggat cttcatctag aaccccaagc   1680
gacaaaccag ttgctcatgt ggtcgccaat cctcaagctg aaggacagct tcaatggctt   1740
aatcgccggg caaacgccct tttggcaaat ggcgttgagc tgcgggataa tcaactggta   1800
gttccaagtg agggcttgta cttgatctat agtcaagtac tgttcaaggg ccaaggctgc   1860
ccatctacac acgttctttt gacccacact atttcaagga ttgccgtcag ctatcaaact   1920
aaagtgaacc tcctgtctgc tatcaagtca ccctgtcaac gagaaacccc tgagggtgct   1980
gaagccaagc cctggtatga gcccatatat ctcggcggag tctttcaact ggagaagggt   2040
gacaggctgt ctgccgaaat caatcggcct gactatctga actttcggga gagcggccag   2100
gtctacttcg gcattattgc tctc                                          2124
```

<210> SEQ ID NO 135
<211> LENGTH: 2136
<212> TYPE: DNA
<213> ORGANISM: Artificial Sequence
<220> FEATURE:
<223> OTHER INFORMATION: Synthetic: Codon optimized nucleic acid sequence encoding SEQ ID NO 115

<400> SEQUENCE: 135

```
gtcaggagta gctctaggac cccatccgat aagcccgtcg cacatgtggt ggccaacccc     60
caggcagaag gccaactcca gtggcttaat agacgagcca atgccctttt ggctaatggc    120
gtcgagctca gggacaatca acttgtggtg cctagtgagg gactctattt gatttatagc    180
caagtacttt tcaagggaca gggttgtcca tctacacacg tgcttcttac ccacactatt    240
tctcggatcg cagtttctta tcaaaccaaa gtcaaccttt tgtccgctat caagagtcca    300
tgtcagagag agacacccga gggcgctgaa gctaagccct ggtatgagcc aatctatctt    360
gggggagttt tccagctcga aaaaggggac cggctgtctg ccgaaattaa ccgccctgac    420
```

```
tacctcaact ttagggagag tggtcaggtg tatttcggaa taatcgcctt gggcggtggc    480
gggtcatcta gcagaacccc atccgacaag ccagtcgccc atgtagtggc caatccacag    540
gcagagggac aattgcagtg gttgaatcgg cgagccaatg cattgctcgc aaacggggtg    600
gagctccgcg ataaccagct tgtagtgcca tccgaaggat tgtatttgat ttattctcaa    660
gtgctgttca aaggacaagg gtgcccatct acccatgtct tgctgacaca cacaatttcc    720
cggatcgctg tatcctacca aaccaaggtg aatcttttgt cagcaatcaa aagcccatgt    780
caacgcgaaa caccagaggg agcagaggcc aagccttggt acgagcctat ttacctgggc    840
ggtgtctttc aacttgagaa gggagatcgc ttgagcgcag aaattaatag gcctgactac    900
cttaacttta gggaaagtgg acaggtatat tttggaataa ttgcactcgg tggtgggga     960
tcatcaagcc gcacaccttc cgataaaccc gttgcccacg tagtggcaaa tccccaggcc   1020
gaaggccaat tgcaatggct gaaccgaaga gccaacgctc ttctcgcaaa tggtgtagaa   1080
ctccgggata accagttggt ggtgcccagc gagggccttt atctcatata ctctcaagtc   1140
cttttcaaag ggcagggatg tcctagtacc catgtacttc tcactcacac aatctccagg   1200
atcgccgttt catatcaaac aaaagttaat ttgctcagcg ctataaagag tccatgccaa   1260
cgcgaaacac ctgagggggc cgaagcaaaa ccttggtacg agcctattta tcttggtgga   1320
gtattccaac ttgaaaaagg tgacaggttg tcagctgaga ttaatagacc agattatctg   1380
aattttcgcg aatctgggca ggtttacttc gggataatcg ctctgggagg aggagggagt   1440
gaaccaaagt ccagcgataa aactcatacc tgtccacctt gtccagcccc cgaagctgca   1500
ggaggcccta gcgtgttctt gtttcctccc aaacccaaag acacattgat gattagtcgc   1560
actcctgaag tgacatgtgt tgtcgtagac gtatctcatg aagaccccga agtcaagttt   1620
aactggtatg tcgatggagt ggaggtgcac aatgcaaaga ctaagcctag ggaagaacaa   1680
tataacagta cctacagagt tgtgtcagtg cttaccgtct tgcatcagga ttggctcaat   1740
ggaaaagagt ataagtgtaa ggtaagtaac aaggcattgc ccgctagcat agagaaaaca   1800
ataagcaagg caaaggggca gcccagggaa ccccaagtct ataccctttcc accaagtcgg  1860
gatgaactga ctaaaaatca ggtgtccttg acttgccttg taaagggatt ctacccctca   1920
gatatcgcag tggagtggga gagcaacgga cagccagaaa acaattacaa aaccaccccc   1980
cctgtcctgg attcagacgg ttctttcttt ttgtactcca aacttacagt agacaagtcc   2040
aggtggcaac aaggcaatgt ctttagctgt tctgtcatgc acgaagccct tcacaaccac   2100
tatactcaaa agtcactttc tctttcccct ggaaaa                             2136
```

```
<210> SEQ ID NO 136
<211> LENGTH: 2124
<212> TYPE: DNA
<213> ORGANISM: Artificial Sequence
<220> FEATURE:
<223> OTHER INFORMATION: Synthetic: Codon optimized nucleic acid
      sequence encoding SEQ ID NO 116

<400> SEQUENCE: 136
```

```
gtaagatcat ctagtcggac tccatcagac aaaccagtag cccatgttgt tgcaaaccca     60
caagccgagg gtcaacttca gtggctcaat aggcgcgcca atgcactgct cgctaatgga    120
gtcgaattgc gcgataacca attggtggta cctagtgagg gactttattt gatctatagt    180
caggtgctct ttaaaggtca gggttgcccc tccacccacg ttctcctgac acataccatt    240
agcaggatag ctgtaagtta ccagactaaa gtcaacctcc ttagcgctat caaaagtcca    300
```

```
tgtcaaagag aaactccaga aggagcagaa gccaaacctt ggtacgagcc tatctacctc    360

ggaggagtat ttcagcttga aaagggggat cgactgagcg ccgaaatcaa cagacccgat    420

taccttaact tccgagaatc cggccaagta tacttcggga ttattgccct tgggggaggt    480

ggctcttcaa gcagaacccc atcagacaag ccagtggctc acgtcgttgc caatccccaa    540

gctgaagggc aacttcaatg gcttaatcga agggctaatg cacttttggc caacggtgta    600

gaactccgag acaaccaatt ggtcgtgcca tcagaaggcc tttacctcat atactcccag    660

gttcttttca agggtcaggg atgtcctagt acacacgtat tgttgaccca tacaatttca    720

aggatagcag taagctacca gactaaagtt aatctgctta gtgctataaa gtctccttgt    780

cagcgagaga cacccgaagg cgctgaggca aaaccctggt acgagcccat ctacctcggg    840

ggtgtttttc aactggagaa gggagaccga ctgtccgccg aaattaaccg gcccgactac    900

ctcaattttc gcgaatccgg gcaagtttat tttggtatca ttgcattggg tggtggaggc    960

tccagtagcc ggactccctc cgataaacca gtggcacatg tagtcgccaa ccctcaagca   1020

gaagggcaat tgcagtggct gaatagacgc gccaatgccc tcctggctaa tggcgtagag   1080

cttagagata atcaattggt ggtgcctagt gaaggtctgt acctcattta ctctcaggtt   1140

ctctttaagg gccaaggatg tccctcaact cacgtactgc tgactcatac tatatcacgg   1200

atagccgtct cttaccagac aaaagtgaat ttgctgtcag ccatcaagag tccatgccag   1260

cgagaaaccc ctgagggggc tgaagctaaa ccatggtatg aaccaatcta ccttggtggc   1320

gttttccagc tcgagaaggg cgatagactt agcgccgaaa ttaatcgacc agactatctc   1380

aattttagag agtcaggaca agtgtacttt ggtattatag ccttgggtgg gggcggttct   1440

gaacggaaaa gttctgttga atgccctcca tgtcctgccc cccctgtggc cggtccctca   1500

gtctttctct tcccacccaa gcccaaagat acattgatga ttagtaggac tcccgaggtg   1560

acttgcgtag ttgtcgatgt ttcccatgaa gatccagaag tgcaatttaa ctggtatgta   1620

gacggcgtcg aggtccataa tgctaaaact aagccccgcg aggagcagtt taattcaacc   1680

tttagagttg tgagcgttct gaccgttgta caccaggatt ggcttaatgg taaagagtac   1740

aagtgcaagg tgtccaacaa gggacttcca gcatccattg aaaagaccat ttccaagact   1800

aaagggcaac cacgggaacc acaagtctac accctcccac ccagccgcga agagatgact   1860

aaaaatcagg tatcacttac ttgcctggtt aagggtttct acccatctga cattgctgtc   1920

gagtgggaat ctaatgggca acctgaaaac aattacaaga caacaccacc tatgctggat   1980

tccgatggga gtttcttcct gtacagtaaa ctcactgttg acaagtcccg atggcagcag   2040

ggaaatgtct tttcatgctc cgttatgcat gaggccctcc acaaccatta tacccaaaag   2100

tctctgtccc tgtcaccagg aaag                                          2124
```

```
<210> SEQ ID NO 137
<211> LENGTH: 2082
<212> TYPE: DNA
<213> ORGANISM: Artificial Sequence
<220> FEATURE:
<223> OTHER INFORMATION: Synthetic: Codon optimized nucleic acid
      sequence encoding SEQ ID NO 117

<400> SEQUENCE: 137

gaatcaaagt acggtccacc ttgtcctccc tgtcccgccc ccgagtttct gggggggtccc    60

tctgtctttc tgtttccacc aaagcccaag gacactctga tgattagcag aacaccagaa    120

gtaacctgtg tcgtcgtgga tgtctcacag gaggatcccg aggtacagtt caactggtac    180
```

```
gtggatggtg tagaggtgca taatgcaaag actaaaccaa gggaagaaca attcaattct    240

acttaccggg tcgtatctgt cttgaccgtg cttcaccaag attggctgaa cggcaaggag    300

tataaatgta aagtttctaa taaggggctc ccatcaagta tcgagaaaac catttcaaaa    360

gcaaaagggc aacctcgaga gcctcaagtt tacacactcc ctccatcaca agaagaaatg    420

acaaagaatc aagtcagcct cacctgcctt gtaaagggct tctatccctc cgacattgca    480

gtggaatggg agtcaaacgg acaacctgag aataattata agaccacacc tccagtgctg    540

gactcagatg ggtcattttt cctgtactcc cgcttgaccg tggacaagtc tcgatggcag    600

gaaggtaatg tgttcagctg tagtgtgatg cacgaagcac tgcacaacca ttatacccag    660

aaatccctgt cattgtccct cggtaaggtg agatccagta gccgcacacc aagtgataaa    720

cctgtagccc acgtagtggc aaatccacaa gctgaagggc agctccagtg gctgaatcgc    780

cgcgcaaacg cactgctggc aaatggggta gagcttaggg acaatcagct cgtagtgccc    840

agtgaaggcc tctatctcat ttattcacaa gtacttttca aaggccaggg atgccctagt    900

acccatgtcc ttttgacaca caccatctcc cgaatagccg taagctacca aactaaggtt    960

aatctcctta gcgcaatcaa atctccttgc caaagggaaa cccccgaagg cgccgaagcc   1020

aagccctggt atgaacctat ataccttggc ggggtttttc agctggaaaa gggagacagg   1080

ttgagtgccg agattaatcg accagactac cttaatttta gagagtccgg ccaggtctat   1140

ttcgggataa tcgctctgtc ttctagaact cccagtgata aacccgttgc ccacgtggtg   1200

gccaacccac aggccgaagg gcaactgcag tggctgaaca gacgagcaaa tgcattgttg   1260

gccaacggtg ttgaactgcg cgacaaccaa cttgtggtgc ctagtgaggg tctctacttg   1320

atttattccc aagtcctctt taaagggcaa gggtgtccct ctactcatgt cctgctcact   1380

cacaccatct ccagaattgc agtatcttat cagacaaaag taaacttgct gtcagccatt   1440

aaatcaccat gtcagaggga gacacctgaa ggtgcagaag ctaagccttg gtatgaacct   1500

atttatctcg gcggggtgtt ccaattggag aaaggggacc gactgagcgc tgaaatcaat   1560

agacccgatt atttgaactt tagagagagt ggccaggtat acttcggtat aatagccctg   1620

tccagtcgaa ctccttctga taagcctgtc gcacatgttg tggcaaatcc tcaagctgag   1680

ggacagctcc aatggttgaa tagacgcgcc aacgcactcc tcgctaacgg ggttgagctc   1740

cgagacaatc agcttgtcgt cccaagcgag ggctgtacc ttatttactc ccaggtattg    1800

tttaagggac agggttgccc ctccacacat gtgctcctga cccacactat cagccgaata   1860

gccgttagct atcaaacaaa ggtcaatctc ctgagtgcaa taaagtctcc ttgtcagcga   1920

gaaacccccg aaggcgccga ggccaagccc tggtacgagc caatttacct cggtggagtc   1980

tttcagttgg agaaggggga tagattgagc gcagaaatta accgacctga ctatttgaac   2040

ttcagagaaa gcggacaagt ctattttggt atcatcgccc tg                      2082
```

<210> SEQ ID NO 138
<211> LENGTH: 2079
<212> TYPE: DNA
<213> ORGANISM: Artificial Sequence
<220> FEATURE:
<223> OTHER INFORMATION: Synthetic: Codon optimized nucleic acid sequence encoding SEQ ID NO 118

<400> SEQUENCE: 138

```
gaatcaaagt acggccctcc atgtccaccc tgtcctgccc ctgagtttct cggaggaccc     60

agtgtattcc tcttcccacc aaaacccaag gataccctca tgatcagcag gactcccgaa    120
```

-continued

```
gttacatgcg ttgtcgtaga cgtatcacag gaagatcctg aggtccaatt taattggtac    180

gtcgacggag tcgaagttca taacgccaaa acaaaaccac gagaagagca atttaacagt    240

acatatcgcg tggtctcagt gctgaccgtg ctccaccagg actggctcaa tgggaaagaa    300

tacaaatgta aggtttccaa taagggactc cctagctcaa tagaaaagac catttcaaaa    360

gctaaaggcc aaccccggga gccccaagtc tacacccttc cccccctctca ggaagaaatg    420

accaaaaatc aggtgtccct gacctgtctt gtgaaagggt tttatccctc agacattgcc    480

gtagagtggg aatcaaatgg acaacccgag aacaactata aaactactcc acctgttctg    540

gactccgatg gttccttttt cctgtacagc cgccttaccg ttgacaaatc acgatggcag    600

gaagggaatg tcttcagttg ttcagtaatg catgaagctc tccataacca ctatactcag    660

aagtccctgt ccctctctct gggcaagggc ggcggtggtt ccgtccgcag ttcttctcgg    720

actccctccg acaagccagt cgcacatgta gtcgccaacc cacaagcaga gggacagctt    780

cagtggctca atcgaagagc aaacgccctc cttgcaaacg gcgtcgaact tcgcgacaac    840

caactggttg ttccatcaga aggcttgtat ctgatctact ctcaggtgct gtttaaggga    900

cagggatgtc ctagcacaca tgtgctcctt actcatacaa tttcaaggat cgcagtaagc    960

taccaaacta aagtgaacct ccttagcgcc ataaagtccc catgccaaag ggagacaccc   1020

gagggagcag aagcaaagcc atggtatgaa cctatctatc tcggtggagt tttccagttg   1080

gagaaaggtg atagactctc tgctgagatc aatcgccccg actatctgaa tttccgcgaa   1140

tctgggcagg tctactttgg gataatagca ctgggtggcg gtggatctcc cgtagctcac   1200

gtggtcgcta acccacaggc tgaggggcaa ttgcaatggt tgaaccggcg ggctaatgct   1260

ttgttggcaa acggcgtaga attgagagac aaccaattgg tcgttccttc agaaggattg   1320

tatctcatct acagccaagt cttgtttaaa ggccaaggct gtccatctac acacgtgctt   1380

cttactcaca caatctcacg aatcgcagta tcttatcaga ccaaagtgaa cttgctctct   1440

gcaataaaaa gcccttgtca acgcgaaact ccagaagggg ctgaagcaaa gccatggtac   1500

gaacctattt atctcggggg ggtgttccaa ctcgagaaag gggaccgact gtccgctgaa   1560

atcaaccgcc ctgactatct taatttccgg gagtctgggc aggtatattt cggtataatt   1620

gcacttggag gcggggggtc acctgtggca catgtagtcg ccaaccccca agctgaagga   1680

caacttcaat ggctcaatag gcgcgcaaat gctctgctcg caaatggagt agaactccgg   1740

gataatcaac tggttgtgcc ttctgaagga ctgtatctga tctatagcca agttttgttc   1800

aagggccagg ggtgcccatc tacacacgta cttcttaccc acacaatatc ccgcatcgcc   1860

gtcagttatc agacaaaagt gaaccttttg tccgccatca agagcccatg tcagcgcgaa   1920

actcccgagg gtgctgaggc taaaccatgg tatgagccca tctatttggg aggcgtattt   1980

caactggaaa aaggggatcg actgagcgca gagatcaata ggcccgatta tcttaatttc   2040

agggagtctg gtcaagtgta ttttgggata attgctctg                          2079

<210> SEQ ID NO 139
<211> LENGTH: 2094
<212> TYPE: DNA
<213> ORGANISM: Artificial Sequence
<220> FEATURE:
<223> OTHER INFORMATION: Synthetic: Codon optimized nucleic acid
      sequence encoding SEQ ID NO 119

<400> SEQUENCE: 139

gaatctaagt atgggccacc atgcccacca tgcccagccc cagaattcct gggcggacct     60
```

```
tccgttttct tgttcccacc aaagccaaaa gatactctga tgatttccag gacccctgaa    120
gttacctgtg tggtagtgga tgtcagccag gaggatccag aagttcaatt taattggtat    180
gtagacggag tcgaagtcca taacgctaaa actaaacctc gagaagagca gtttaattca    240
acctacaggg ttgtttccgt actgacagtt ttgcatcagg actggctgaa tggcaaggaa    300
tacaaatgca aggtcagcaa caaaggactc ccaagttcaa tagaaaagac catttcaaaa    360
gctaaagggc aaccacgaga acctcaggtc tacactctcc ctccctctca ggaagagatg    420
actaaaaatc aggtttcact tacatgcctc gtgaagggct tttaccccag cgacattgct    480
gttgagtggg agagtaacgg acaacctgag aacaactaca agactacacc tcctgtgctg    540
gactcagatg gttccttctt tttgtatagc aggcttaccg ttgataagtc ccgctggcaa    600
gaaggcaacg ttttcagttg ttcagtaatg cacgaagctc tccacaatca ttatacacag    660
aagagtctta gcctgtccct gggtaaggga ggcggggggt ccgggggcgg gggctcagtt    720
cgctcatcaa gccgaacacc ctcagacaag ccagttgccc acgtcgtagc caaccccaa     780
gctgaaggac agttgcaatg gctgaatagg cgagctaatg cattgttggc aaatggagta    840
gaactgcgcg ataatcaatt ggttgtgccc tcagaagggc tgtaccttat ttactcccag    900
gtgctcttca aagggcaggg ttgcccttca acccacgtac ttcttaccca cacaataagc    960
aggattgccg tctcctacca aactaaagta aacctgttga gcgctatcaa gagtccttgc   1020
caacgggaga cccctgaagg tgcagaggca aaaccatggt acgaacccat ttatctcgga   1080
ggggtgttcc agttggagaa gggggaccgc ctgtctgccg aaatcaatag gccagactac   1140
ctcaactttc gcgagtccgg gcaggtgtat tttgggatca tagctttggg cggtggggga   1200
tctcctgttg ctcatgtcgt tgcaaaccct caggctgaag gccaattgca atggctcaac   1260
aggagagcta acgcattgct ggccaacggg gttgagctcc gcgataacca gctggtagtt   1320
ccctcagagg gcttgtacct tatctattca caggttctct tcaaaggaca aggatgtcct   1380
agcacacacg tcttgcttac acataccatt agccggatag cagtttctta tcagactaaa   1440
gttaatctcc tctctgccat aaagtcaccc tgtcagcggg aaacacctga gggtgctgaa   1500
gcaaaacctt ggtatgaacc aatatacctc ggtggagttt ttcaactgga gaagggcgac   1560
agactgagcg ctgaaataaa cagacctgac taccttaatt tccgagaatc aggtcaagta   1620
tacttcggga ttatagcctt ggggggtgga ggctccccag tggctcatgt agtcgctaat   1680
ccccaagctg aaggccaact ccaatggctt aacaggaggg ccaacgcact cctcgcaaat   1740
ggagtcgagc ttagggataa tcaattggtg gttccctctg agggcttgta tcttatttat   1800
tcacaggtcc tgtttaaagg ccaaggctgt ccttctacac atgtcctgtt gactcatacc   1860
ataagtagaa tagccgtgag ttaccagaca aaggttaacc tgctttccgc aatcaaatct   1920
ccatgccaac gcgagacccc agaaggggca gaagcaaagc cttggtacga gcccatatat   1980
ctcggtgggg tctttcagct cgagaaaggc gaccggctta gcgctgaaat caaccgccca   2040
gactatttga actttcggga aagtggacaa gtctacttcg gtatcatagc actc         2094
```

<210> SEQ ID NO 140
<211> LENGTH: 2112
<212> TYPE: DNA
<213> ORGANISM: Artificial Sequence
<220> FEATURE:
<223> OTHER INFORMATION: Synthetic: Codon optimized nucleic acid sequence encoding SEQ ID NO 120

<400> SEQUENCE: 140

```
gaatctaagt atggacctcc ttgtccacca tgtccagctc ccgagttcct gggaggccca     60
tccgtgtttt tgttcccccc taagccaaaa gacacactta tgatatcaag aaccccagaa    120
gttacttgtg tagtcgtgga cgtatcccag gaagaccccg aggttcaatt taactggtat    180
gtagacggcg tggaagtcca taatgctaag acaaagcccc gggaggaaca attcaactcc    240
acataccgag tagtatccgt attgaccgtg ctccatcagg attggttgaa tggaaaggaa    300
tacaagtgca aagtttctaa taagggcctg ccttctagca tcgagaagac catcagcaag    360
gctaagggac agcctcgcga accccaagtt tataccctte ctcctagcca agaggagatg    420
actaaaaatc aggtgtcact cacctgcctc gtcaaaggat tctacccatc agatatagca    480
gtggaatggg agtccaacgg gcaacctgag aataactaca aaacaactcc acctgtcctg    540
gactccgacg gctccttctt tctttattcc agacttaccg tggacaaaag cagatggcaa    600
gaggggaatg tgtttagctg cagtgttatg catgaagctt tgcataatca ttacacccaa    660
aaatcacttt cactctctct tggtaagggg ggtgggggat ctggtggggg aggctccgtg    720
cgatcaagct ctaggacacc ctctgataaa cctgttgccc acgtcgtcgc aaatccccag    780
gccgaaggac agttgcagtg gctgaatcga agagctaacg cactgttggc aaacggggtg    840
gagctcaggg ataaccagtt ggtggtgcct tcagaagggc tttatctcat ttactcacaa    900
gtactcttta aagggcaagg gtgcccatct actcacgtgt tgctgactca cactatttct    960
cgaatcgcag ttagctatca aaccaaggta aacttgctca gtgccataaa aagtccttgt   1020
caaagggaga cacccgaagg agcagaagca aagccctggt acgagcccat ttacctcggt   1080
ggtgtcttcc agctggagaa aggagaccgg ctctctgcag agataaacag acctgactat   1140
ctcaacttta gagaatcagg ccaggtttat ttcgggatca tcgcactctc cagccggacc   1200
ccctcagaca agcccgttgc acacgtcgtt gctaacccac aagctgaagg gcagttgcag   1260
tggttgaatc gaagagcaaa cgctctcttg gccaacggtg tagaactccg cgacaaccaa   1320
ctggttgtac cttcagaagg gctctatctg atttactctc aggtgctttt caagggccaa   1380
gggtgcccta gtacacatgt tctgcttacc cacacaattt ctagaattgc agttagctac   1440
cagactaaag tcaacctgtt gagtgctatc aagtcccctt gtcagagaga aaccccagag   1500
ggagctgagg ctaaaccttg gtatgagccc atatacctcg gtggtgtatt ccaattggag   1560
aaaggtgatc gattgtcagc tgaaatcaac agaccagact atctgaattt cagagagtca   1620
ggacaagttt acttcggcat aatcgcattg agtagtcgga caccctccga taaacctgtg   1680
gcacatgttg tagctaaccc tcaagcagag ggcagctcc aatggctgaa ccggcgcgct    1740
aatgccctgt tggctaacgg cgttgagttg cgagataacc agctggttgt gccctctgaa   1800
ggtctgtact tgatctactc ccaagtcctg tttaagggtc aaggctgtcc cagcacacac   1860
gtgttgctca cccacactat cagccggatt gccgtaagct atcaaactaa agtcaatctt   1920
ctgtccgcca tcaaaagtcc atgtcagcgc gaaacccctg agggtgccga agccaagcct   1980
tggtacgagc caatctacct gggtggcgtc tttcagctcg aaaaggggga ccggctctct   2040
gcagagataa atcgccctga ttatcttaac tttcgcgagt ccgggcaggt atactttggg   2100
attatagctc tt                                                       2112
```